US007618977B2

(12) United States Patent
Fukami et al.

(10) Patent No.: US 7,618,977 B2
(45) Date of Patent: *Nov. 17, 2009

(54) METHOD OF TREATING DERMATITIS COMPRISING ADMINISTERING A CHYMASE INHIBITOR

(75) Inventors: Harukazu Fukami, Kyoto (JP);
Yoshiaki Tomimori, Suita (JP);
Yoshiaki Fukuda, Ibaraki (JP); Naohiro Watanabe, Tokyo (JP)

(73) Assignee: Asubio Pharma Co., Ltd., Minato-Ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/959,252

(22) PCT Filed: Feb. 22, 2001

(86) PCT No.: PCT/JP01/01323

§ 371 (c)(1),
(2), (4) Date: Oct. 22, 2001

(87) PCT Pub. No.: WO01/62294

PCT Pub. Date: Aug. 30, 2001

(65) Prior Publication Data

US 2002/0183339 A1   Dec. 5, 2002

(30) Foreign Application Priority Data

Feb. 22, 2000   (JP) .............................. 2000-050504

(51) Int. Cl.
*A61K 31/517* (2006.01)
*A61K 31/535* (2006.01)
(52) U.S. Cl. .............. 514/266.1; 514/266.2; 514/266.3; 514/230.5
(58) Field of Classification Search ................. 514/259, 514/266.3, 266.2, 266.31
See application file for complete search history.

(56) References Cited

U.S. PATENT DOCUMENTS 4,684,654 A   8/1987  Wright, Jr. et al.
4,854,965 A   8/1989  Bracha et al.

FOREIGN PATENT DOCUMENTS

| CA | 2336909 A1 | 1/2000 |
|---|---|---|
| EP | 795548 A1 | 9/1997 |
| EP | 0 936 216 A1 | 8/1999 |
| HU | 218381 | 5/1996 |
| JP | 5-9175 A | 1/1993 |
| JP | 5-294930 A | 11/1993 |
| JP | 10-87493 A | 4/1998 |
| JP | 10-101666 A | 4/1998 |
| JP | 10-245384 A | 9/1998 |
| WO | 93/03625 A1 | 3/1993 |
| WO | 93/25574 A1 | 12/1993 |
| WO | 94/26722 | 11/1994 |
| WO | 96/04248 A1 | 2/1996 |
| WO | 96/33974 A1 | 10/1996 |
| WO | 96/39373 A1 | 12/1996 |
| WO | 97/11941 A1 | 4/1997 |
| WO | 98/18794 A1 | 5/1998 |
| WO | WO98/09949 | 12/1998 |
| WO | 99/41277 A1 | 8/1999 |
| WO | 00/03997 A1 | 1/2000 |
| WO | 00/10982 A1 | 3/2000 |
| WO | 00/51640 | 9/2000 |
| WO | 01/32214 A1 | 5/2001 |
| WO | 01/62292 A1 | 8/2001 |
| WO | 01/62293 A1 | 8/2001 |

OTHER PUBLICATIONS

The Merck Index, 17th edition (1999), pp. 788-789.*
Fukami et al., Current Pharmaceutical Design, (4), (1998), 439-453.*
Teruaki Imada, "Therapeutic potential of specific chymase inhibitor in atopic dermatitis," Abstract, Jan. 2000, Journal of Allergy and Clinical Immunology, vol. 105, No. 1, part 2, p. S267.
Hiroichi Nagai, et al, "An Immunopharmacological Study of the Biphasic Allergic Skin Reaction in Mice," Biol. Pharm. Bull., vol. 18, No. 2, Feb. 1995, pp. 239-245.
Hiroichi Nagai, et al, "FK-506 and Cyclosporin A Potentiate the IgE Antibody Production by Contact Sensitization with Hapten in Mice," The Journal of Pharmacology and Experimental Therapeutics, 1997, vol. 283, No. 1, pp. 321-327.
Hiroichi Nagai, PhD, et al, "Imunoglobulin E production in mice by means of contact sensitization with a simple chemical, hapten," J. Allergy Clin. Immunol., vol. 100, No. 6, part 2, Dec. 1997, pp. S39-S44.
Hideki Kitagaki, et al, "Repeated Elicitation of Contact Hypersensitivity Induces a Shift in Cutaneous Cytokine Milieu from a T Helper Cell Type 1 to a T Helper Cell Type 2 Profile," The Journal of Immunology, vol. 159, No. 5, Sep. 1, 1997, pp. 2484-2491.
Hideki Kitagaki, et al, "Immediate-Type Hypersensitivity Response Followed by a Late Reaction Is Induced by RepeatedEpicutaneous Application of Contact Sensitizing Agents in Mice," The Journal of Investigative Dermatology, vol. 105, No. 6, Dec. 1995, pp. 749-755.
Masaoki Tsudzuki, et al, "Genetic analyses for dermatitis and IgE hyperproduction in the NC/Nga mouse," Immunogenetics, vol. 47, 1997, pp. 88-90.
Hiroshi Matsuda, et al, "Development of atopic dermatitis-like skin lesion with IgE hyperproduction in NC/Nga mice," International Immunology, vol. 9, No. 3, Mar. 1997, pp. 461-466.
Monika Welle, "Development, significance, and heterogeneity of mast cells with particular regard to the mast cell-specific proteases chymase and tryptase," Journal of Leukocyte Biology, vol. 61, Mar. 1997, pp. 233-245.

(Continued)

*Primary Examiner*—Phyllis G. Spivack
(74) *Attorney, Agent, or Firm*—Drinker Biddle & Reath LLP

(57) ABSTRACT

Medicaments for the treatment of dermatitis exhibiting a biphasic inflammation reaction or dermatitis induced by repeated exposure to an antigen, having quinazolidone derivatives of formula I or II that are herein defined, are disclosed.

5 Claims, 25 Drawing Sheets

OTHER PUBLICATIONS

Shaoheng He, et al, "The induction of a prolonged increase in microvascular permeability by human mast cell chymase," European Journal of Pharmacology, vol. 352, 1998, pp. 91-98.

Shaoheng He, et al, "Human mast cell chymase induces the accumulation of neutrophils, eosinophils and other inflammatory cells in vivo," British Journal of Pharmacology, vol. 125, 1998, pp. 1491-1500.

Hitoshi Mizutani, et al, "Rapid and Specific Conversion of Precursor Interleukin 1β (IL-1β) to an Active IL-1 Species by Human Mast Cell Chymase," J. Exp. Med., vol. 174, No. 4, Oct. 1991, pp. 821-825.

B. Jack Longley, et al, "Chymase cleavage of stem cell factor yields a bioactive, soluble product," Proc. Natl. Acad. Sci., vol. 94, Aug. 1997, pp. 9017-9021.

Marilyn C. Ray, et al, "Contact Hypersensitivity Reactions to Dinitrofluorobenzene mediated by Monoclonal IgE Anti-DNP Antibodies," The Journal of Immunology, vol. 131, No. 3, Sep. 1983, pp. 1096-1102.

Takahiro Kunisada, et al, "Murine Cutaneous Mastocytosis and Epidermal Melanocytosis Induced by Keratinocyte Expression of Transgenic Stem Cell Factor," J. Exp. Med., vol. 187, No. 10, May 1998, pp. 1565-1573.

John J. Costa, et al, "Recombinant Human Stem Cell Factor (Kit Ligand) Promotes Human Mast Cell and Melanocyte Hyperplasia and Functional Activation In Vivo," J. Exp. Med., vol. 183, No. 6, Jun. 1996, pp. 2681-2686.

B. Lack Longley, Jr., M.D., et al, "Altered Metabolism of Mast-Cell Growth Factor (*c-kit* Ligand) in Cutaneous Mastocytosis," The New England Journal of Medicine, vol. 328, No. 18, May 6, 1993, pp. 1302-1307.

Tercero et al., "N-Arilsulfonil Ditiocarbamatos de Metilo Como Intermedios en la Sintesis de Heterociclos. Preparacion de Los Sistemas Isomeros 2-Arilsulfonilamino-3-1, 4H-Benzoxazin-4-Onas Y S-Arilsulfonyl-2-4 (1H, 3H)-Quinazolindionas," *Anal. Quimica, Ser. C*, vol. 83, No. 2, pp. 247-250 (1987) (no translation).

Okunishi et al., "Role of mast cell chymase in excessive wound-healing response to vascular injury," *Japan. J. Inflamm.*, vol. 14, pp. 193-197 (1994).

Serruys et al., "Does the New Angiotensis Converting Enzyme Inhibitor Cilazapril Prevent Restenosis After Percutaneous Transluminal Coronary Angioplasty?" *Circulation*, vol. 86, No. 1, pp. 100-110 (1992), Lippincott Williams & Wilkins, Hagerstown, MD.

Urata et al., "Identification of a Highly Specific Chymase As the Major Angiotensis II-Forming Enzyme in the Human Heart," *J. Biol. Chem.*, vol. 265, pp. 22348-22356 (1990), American Society for Biochemistry and Molecular Biology, Baltimore, MD.

Naftilan et al., "Angiotensis II Induces c-fos Expression in Smooth Muscle Via Transcriptional Control," *Hypertension*, vol. 13, pp. 706-711 (1989), American Heart Association, Dallas, Texas.

Okunishi et al., "Different Distribution of Two Types of Angiotensin II-Generating Enzymes in the Aortic Wall," *Biochem. Biophys. Res. Comm.*, vol. 149, pp. 1186-1192 (1987), Biochemical and Biophysical Research Communications.

Okunishi et al., "Evidence for A Putatively New Angiotensin II-Generating Enzyme in the Vascular Wall," *J. Hypertension*, vol. 2, pp. 277-284 (1984), Gower Academic Journals, London, New York.

\* cited by examiner

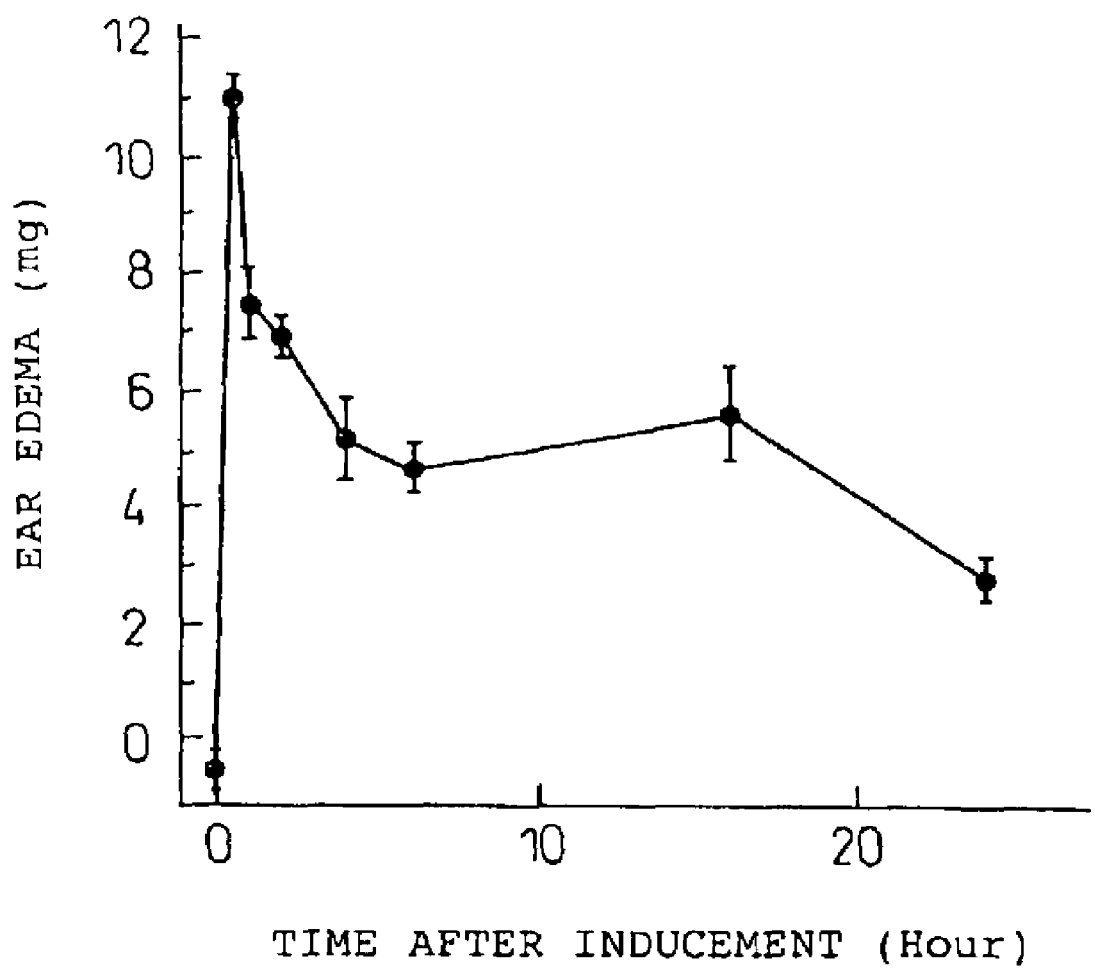

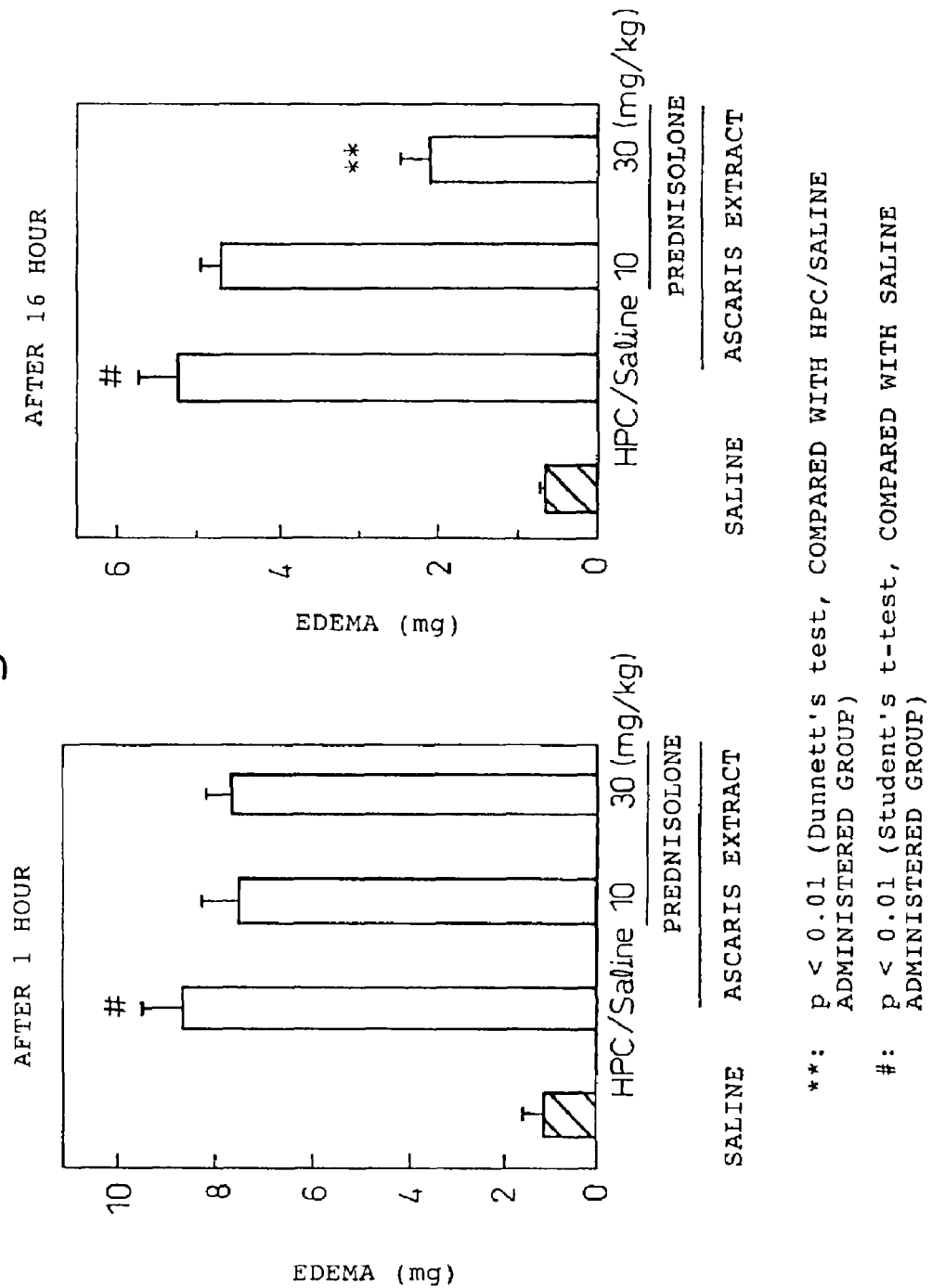

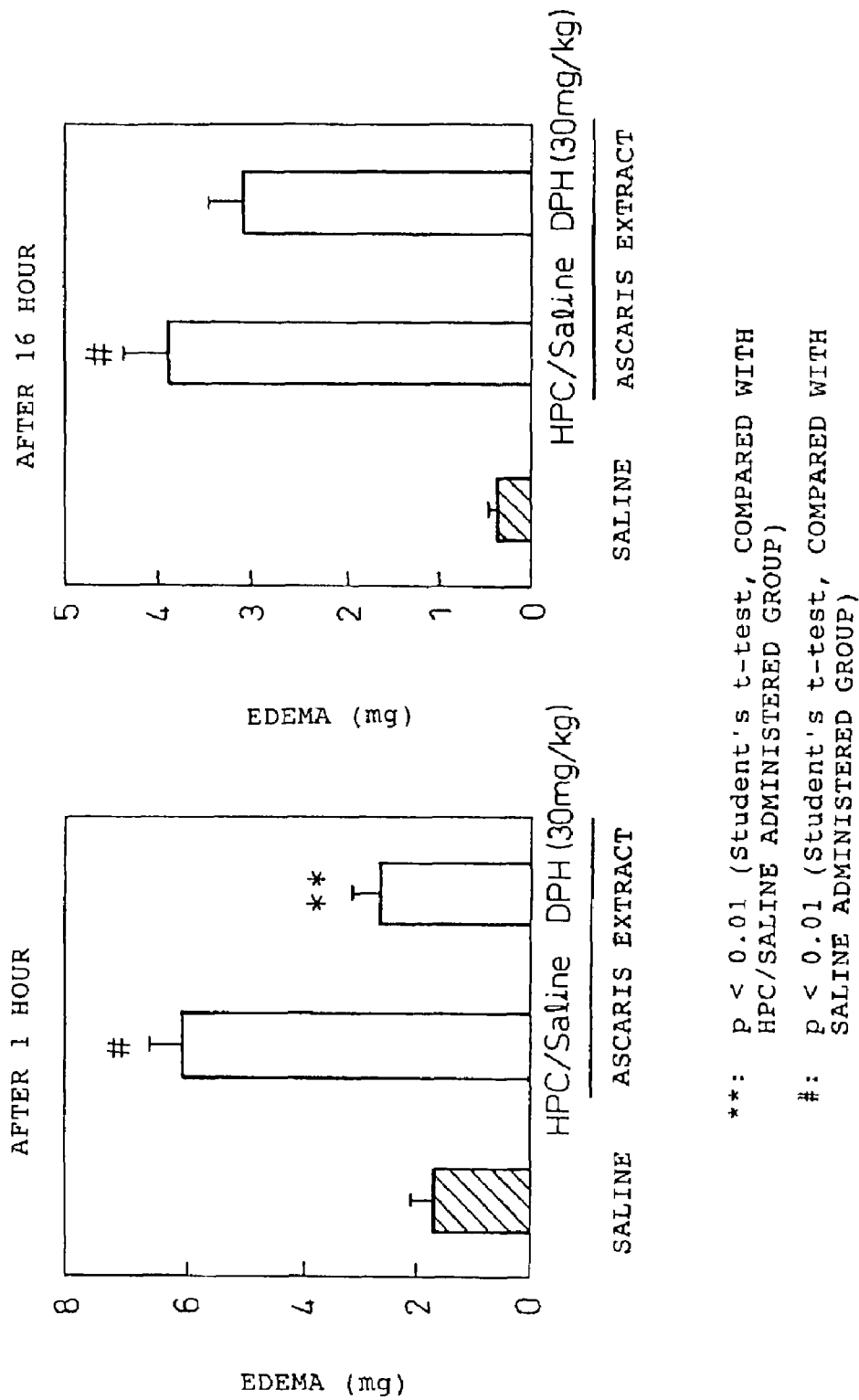

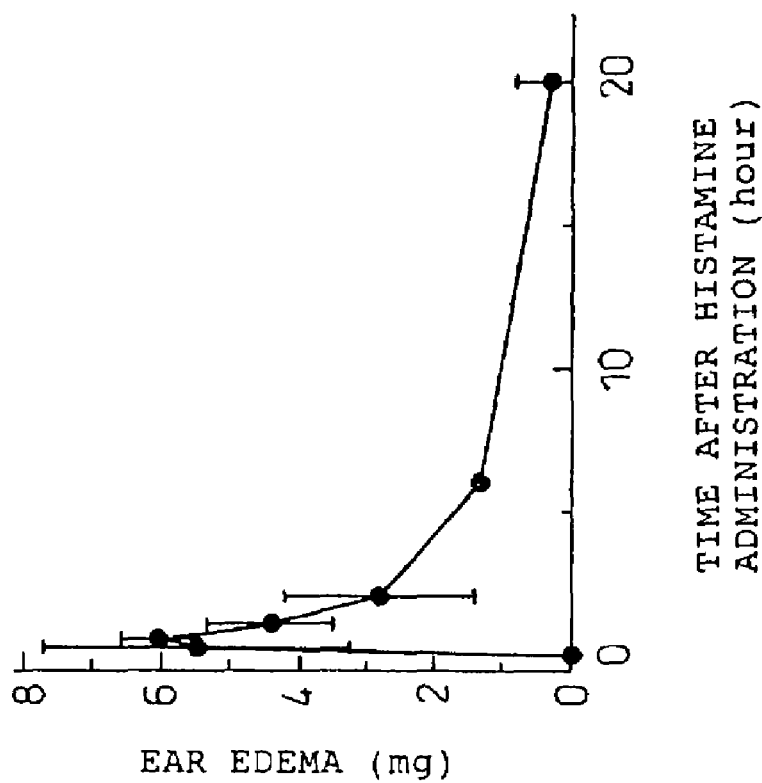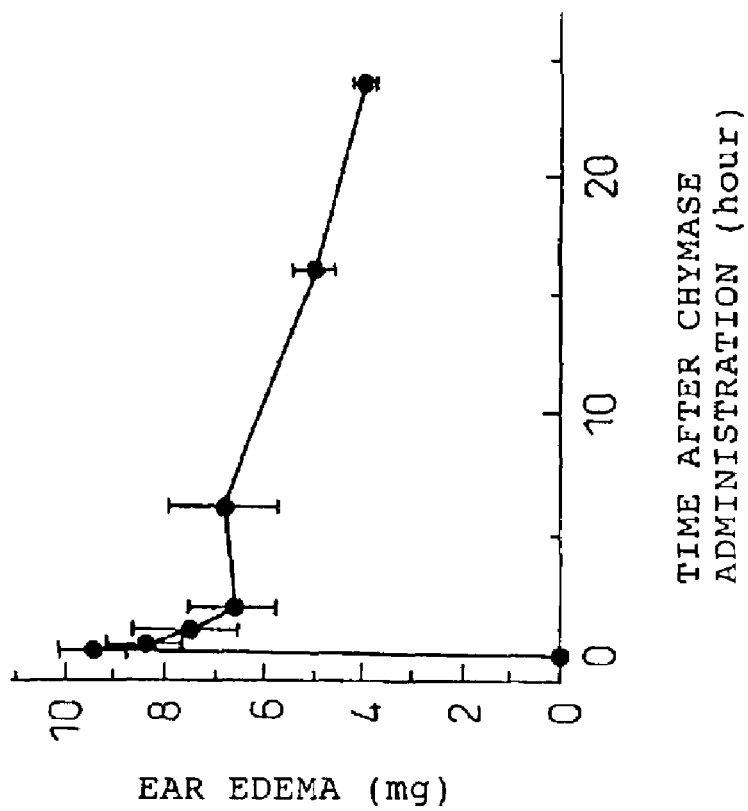

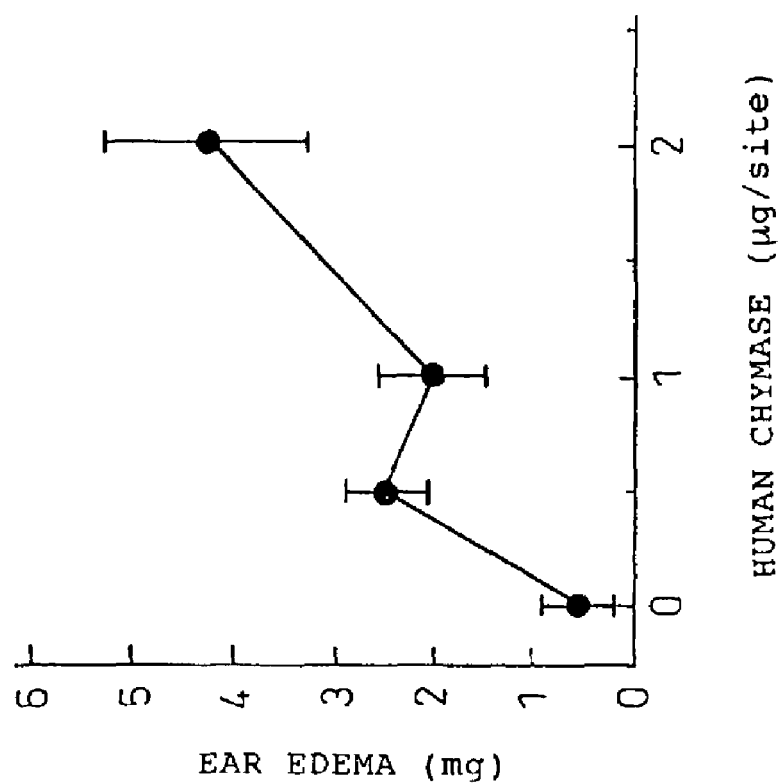
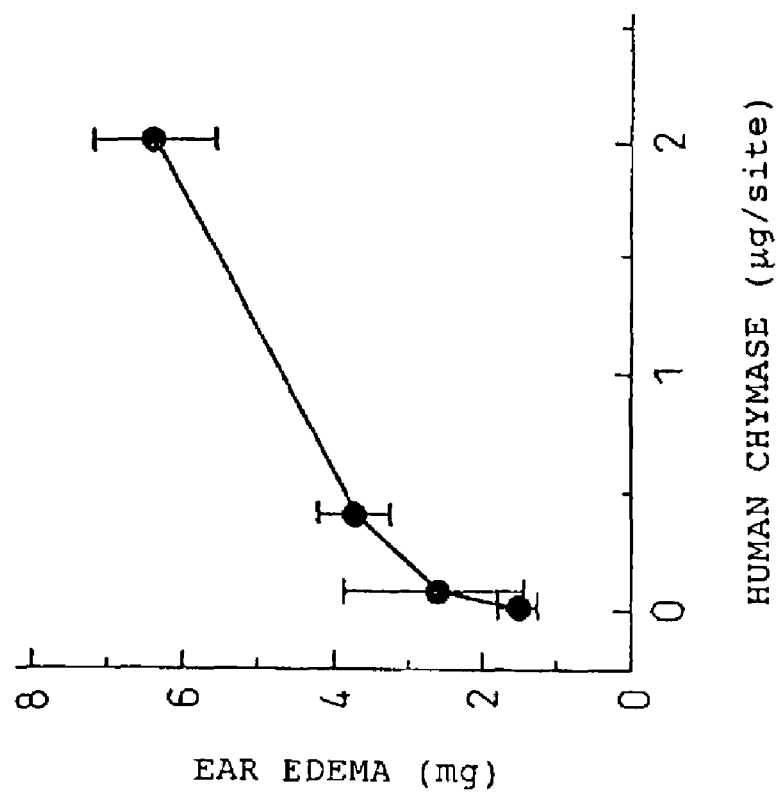

**: p < 0.01 (COMPARED WITH UNTREATED CHYMASE ADMINISTERED GROUP) (Student's t-test)

: p < 0.01 (COMPARED WITH SALINE ADMINISTERED GROUP (Student's t-test)

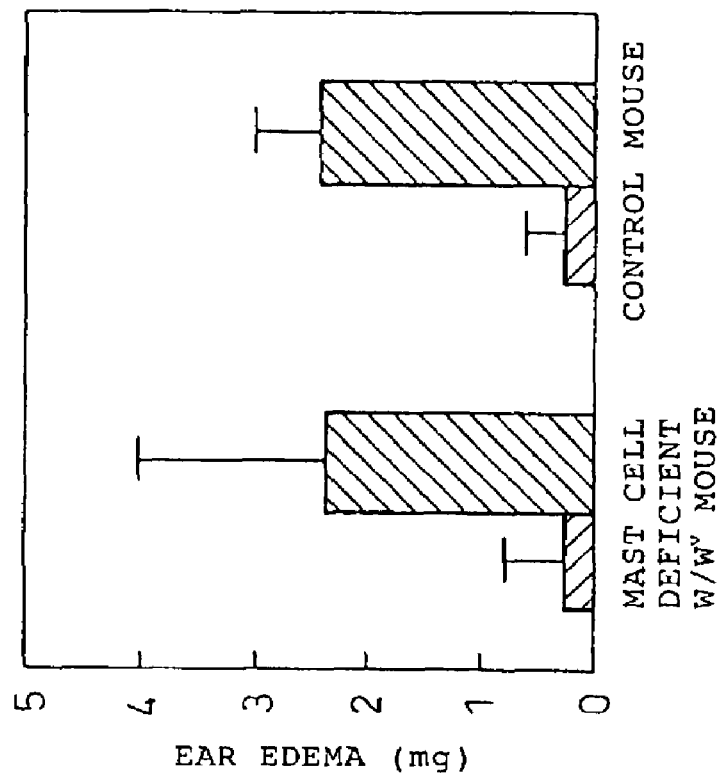
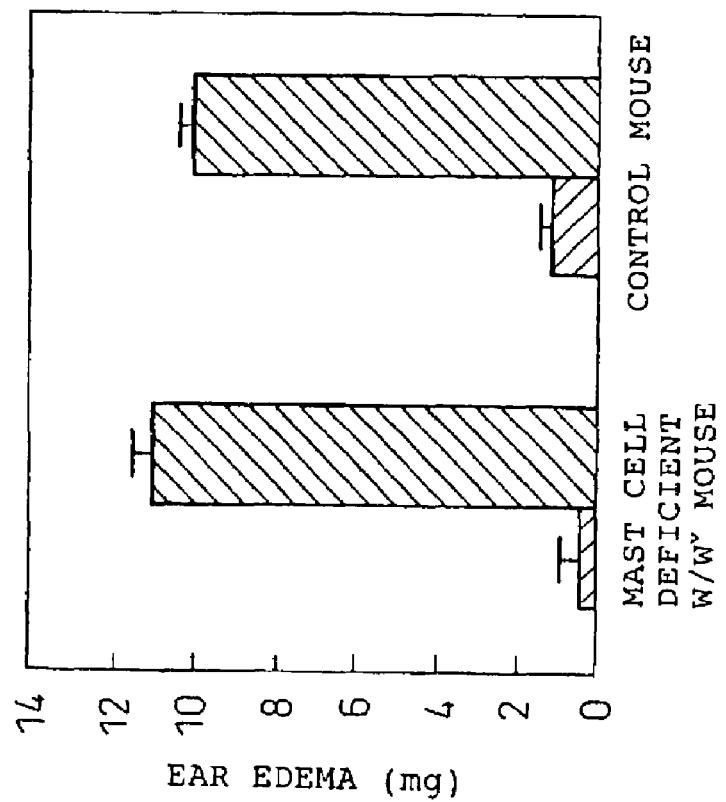

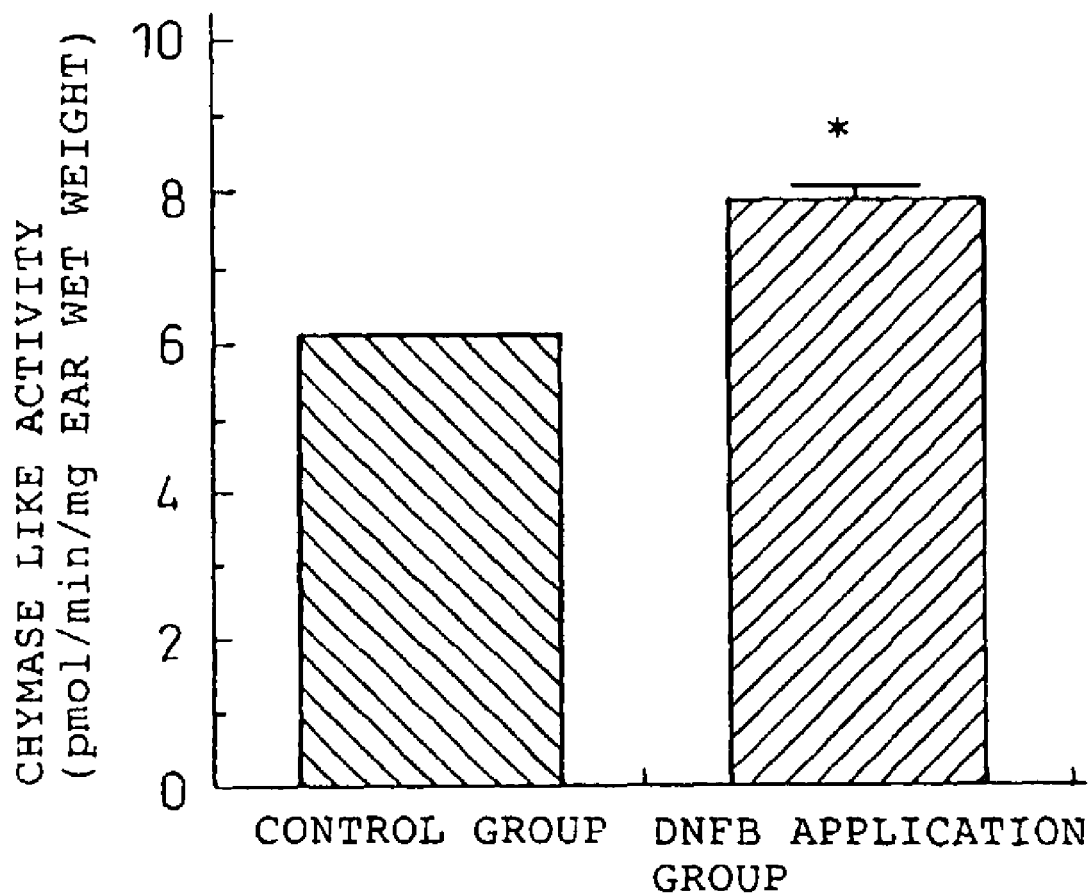

*: p < 0.05, **: p < 0.01 (Dunnett's test, COMPARED WITH CONTROL GROUP)

: p < 0.01 (Student's t-test, COMPARED WITH NON-INDUCED GROUP)

\*\*: p < 0.01 (COMPARED WITH CONTROL GROUP) (Dunnett's test)

\#: p < 0.01 (COMPARED WITH NON-INDUCED GROUP) (Student's t-test)

*: p < 0.05, **: p < 0.01
(COMPARED WITH SALINE GROUP)
(Student's t-test)

**: p < 0.01 (Student's t-test,
COMPARED WITH GROUP SALINE
ADMINISTERED GROUP)

*: p < 0.05 (COMPARED WITH GROUP ADMINISTERED SALINE AT SAME NUMBER OF TIME) (Student's t-test)

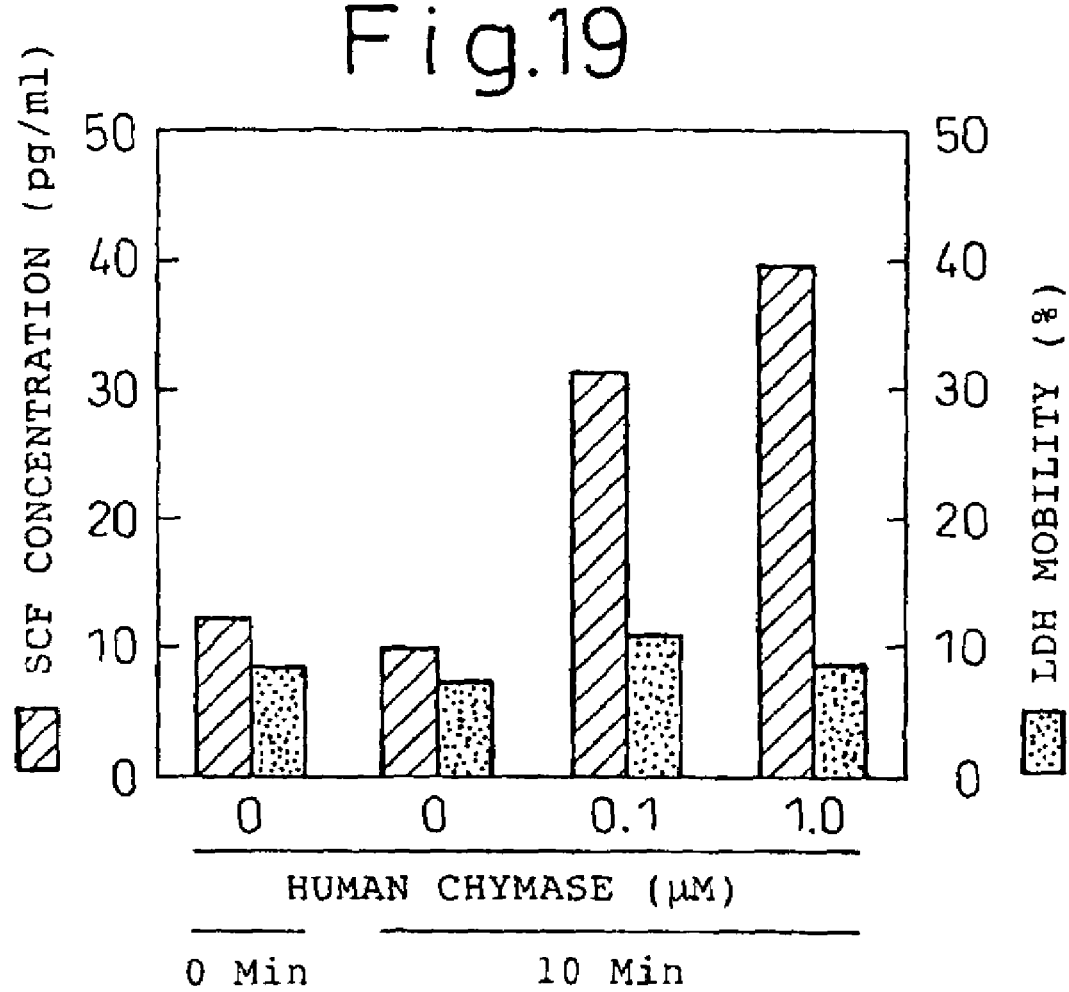

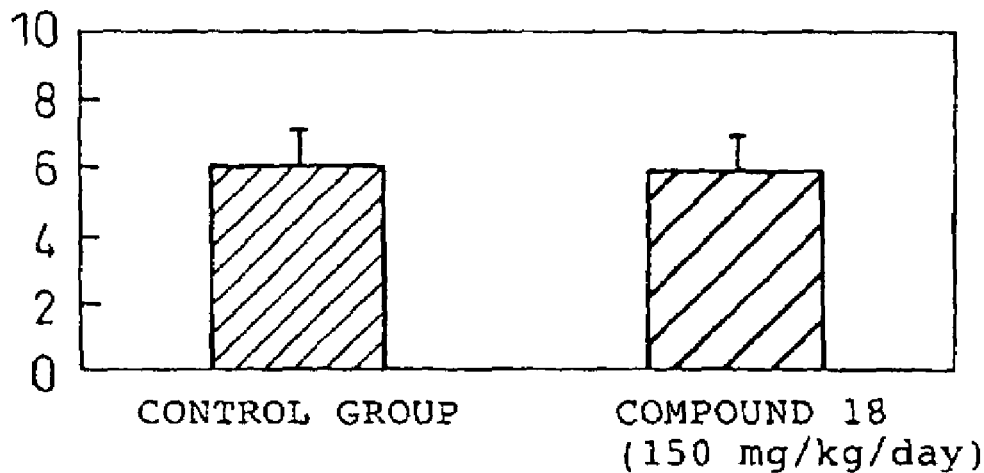
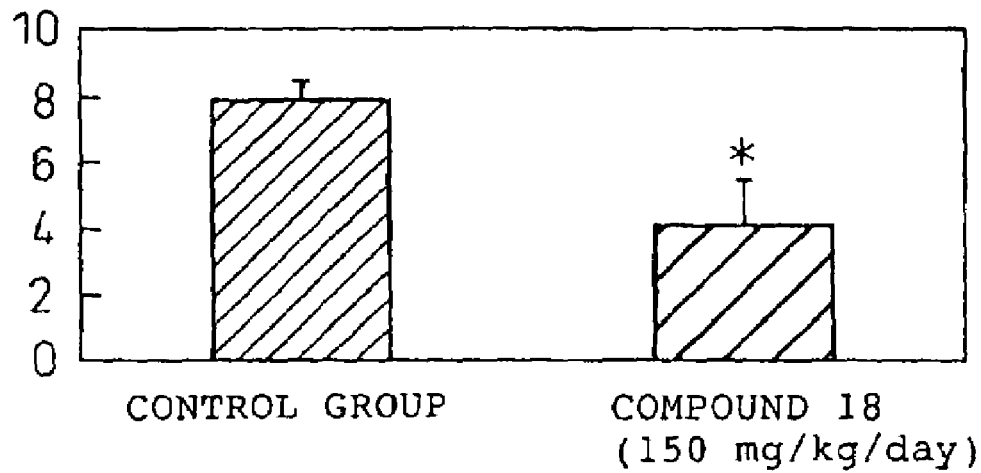
*: p < 0.05 (Mann-Whitney test, COMPARED WITH CONTROL GROUP)

*: p < 0.05 (Mann-Whitney test, COMPARED WITH CONTROL)

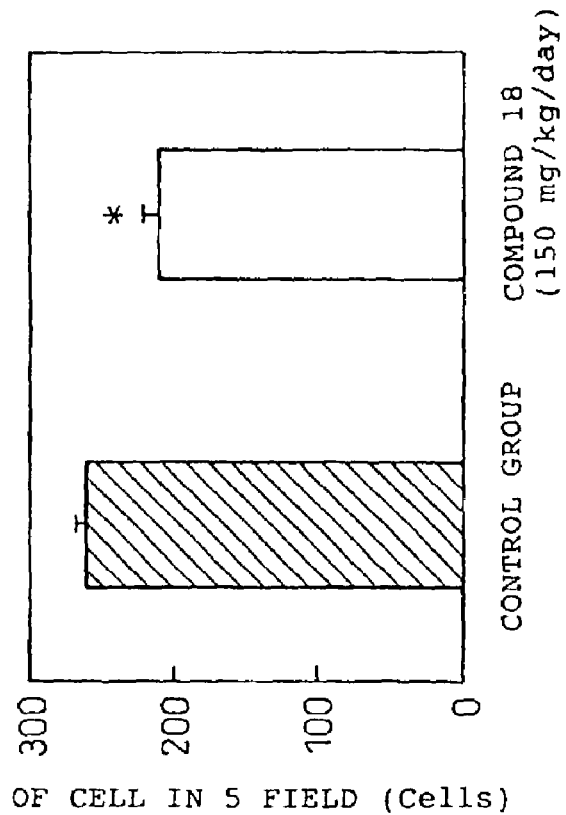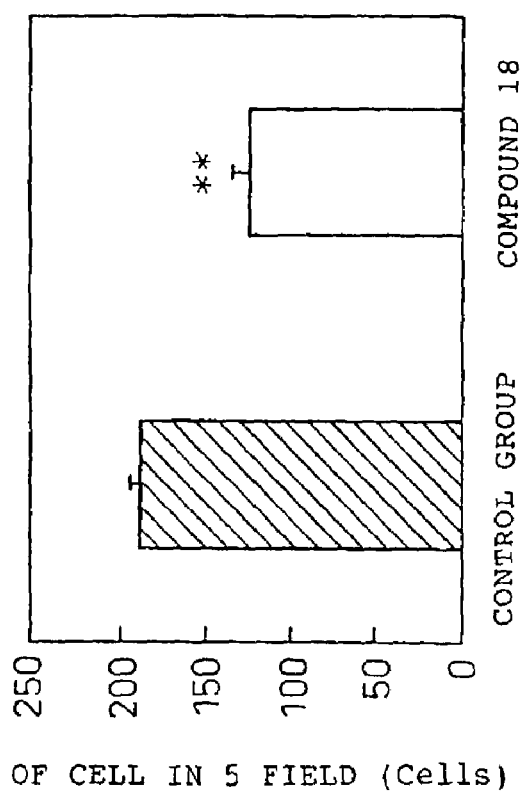

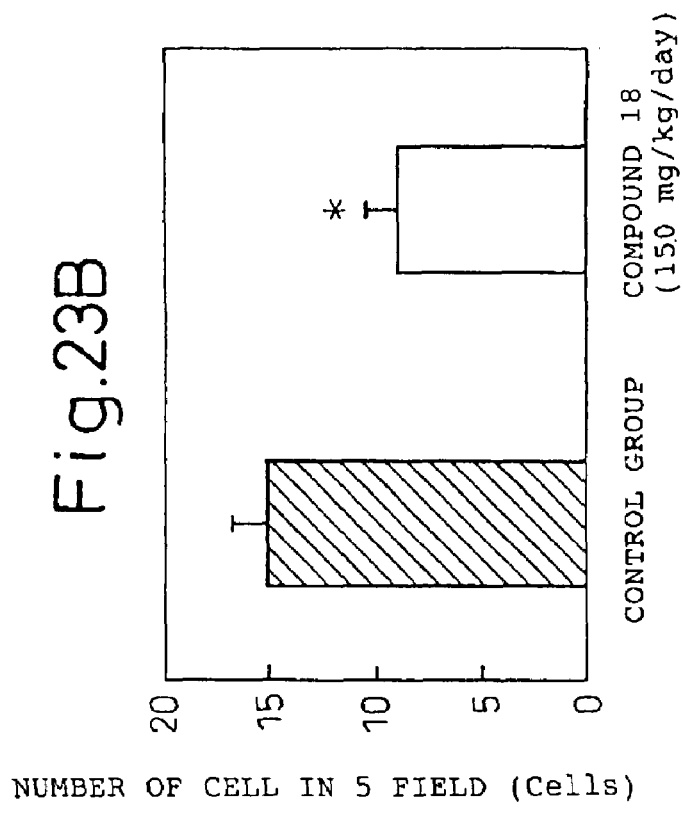
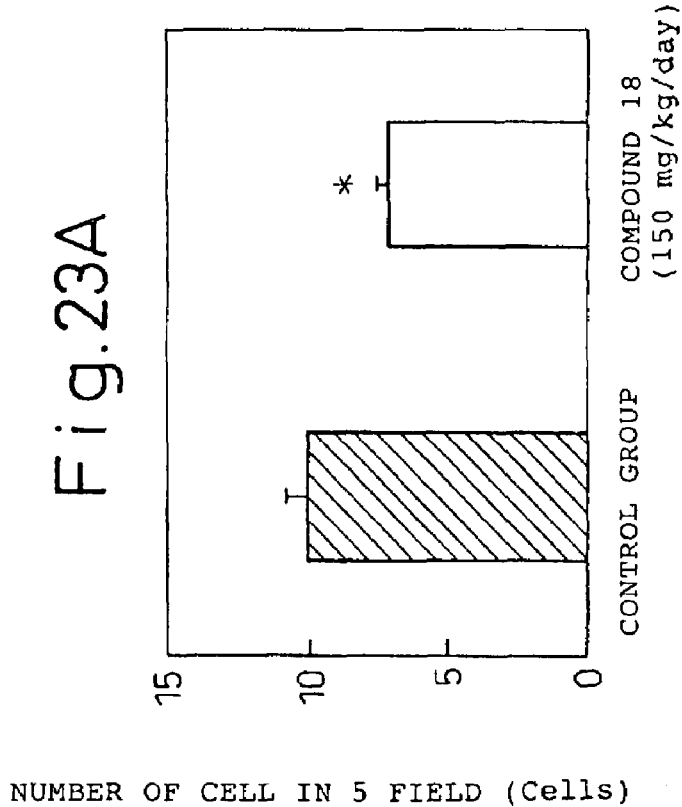

METHOD OF TREATING DERMATITIS COMPRISING ADMINISTERING A CHYMASE INHIBITOR

TECHNICAL FIELD

The present invention relates to medical applications of a chymase inhibitor, more particularly relates to a medicament for the prevention or treatment of dermatitis, which has a chymase inhibitor as an effective ingredient.

BACKGROUND ART

Inflammatory reactions are caused by bacteria, viruses, and other pathogens and by trauma, foreign matter, etc. They are immunoreactions where granulocytes, monocytes, lymphocytes, and other immune cells expel pathogens or injured tissues or foreign materials. Dermatitis is an acute or chronic inflammation of the skin, and in particular, there has been a remarkable rise in atopic dermatitis in recent year, which is becoming a major problem.

Atopic dermatitis is a chronic disease in which eczema with itch is the major condition, with exacerbation and remission observed by turns. In most cases, the patient or his or her family has a history of cnidosis or allergic rhinitis and bronchial asthma and other allergic ailments (*J. Allergy Clin. Immunol.* 104, S123, 1999). The symptoms of atopic dermatitis are diverse and the causes are still unclear, but it is believed that the disease is elicted mainly by various natural substances including ticks, hair, feathers, bacteria and mycetes, or foods including eggs, milk, or synthetic products including chemical fibers and detergents, etc. It is also pointed out that the disorder in the barrier function of the skin due to dry skin plays an important role in atopic dermatitis.

The mechanism of onset of atopic dermatitis is still not clear. It has been thought that the type I allergic reaction (immediate allergic reaction), in which IgE and mast cells are involved, plays an important role in atopic dermatitis, since this disease is one of hypersensitivity reactions to a series of antigens, the patients or their family sometimes have other allergic disorders, and an increase in the serum IgE level is observed in many cases. However, anti-allergic agents that inhibit type I allergic reaction are ineffective or exhibit no therapeutic effect in atopic dermatitis, showing that the involvement of the type I reaction in the pathogenesis of this disease is only partial.

It has been reported, on the other hand, that the patients with atopic dermatitis show biphasic skin reaction, when they are exposed to the allergens (*J. Allergy Clin. Immunol.* 101, 222, 1998). This biphasic skin reaction is, for example, observed in the case of intradermal administration of an antigen such as Ascalis extract to animals sensitized to the same antigen (*J. Immunol.* 131, 1096, 1983). The first reaction, termed early-phase reaction, peaks 1 hr after the antigen challenge. The second reaction, late-phase reaction, is known to show the maximal response after 8 to 24 hours (*Biol. Pharm. Bull.* 18, 239, 1995). Early-phase reaction is suppressed by antagonists to histamine acceptors, suggesting that the reaction is induced by IgE and mast cells. In contrast, the mechanism of late-phase reaction is not necessarily clear, but is characterized by a remarkable infiltration of eosinophils in the skin (*Int. Arch. Allergy Immunol.* 113, 196, 1997), which is the typical histological feature observed in the patients with atopic dermatitis (*J. Am. Acad. Dermatol.* 24, 1101, 1991). Further, the severity of atopic dermatitis patients is known to be correlated with the serum level of ECP (eosinophil cationic proteins), and the number of peripheral eosinophils (*Medicina* 34, 220, 1997). Further, in recent years, it has been pointed out that the clinical symptoms of atopic dermatitis are extremely similar to the symptoms of contact dermatitis classified as a type IV allergic reaction (*Medicina* 34, 220, 1997). These findings suggest the possibility that a type IV allergic reaction is also involved in the mechanism of pathogenesis of the disease.

It is generally known that contact hypersensitivity reaction, the representative type IV allergic reaction, is induced by applying hapten such as DNFB (dinitrofluorobenzene) to the mice that had been sensitized once with the same hapten, but it has been recently reported that a type I allergic reaction is induced in addition to a type IV allergic reaction when repeatedly applying such a hapten to the skin (*J. Invest. Dermatol.* 105, 749, 1995). For example, by repeatedly applying hapten, the IgE level in the blood rises and the time-course of the reaction shifts to that of type I allergic reaction, by repeating the hapten challenge. In such an animal model, not only the transit response to hapten challenge, but also the baseline of skin thickness, the thickness before the hapten challenge, gradually increases, which seems to be a feature of chronic dermatitis. These findings suggest that the dermatitis induced by repeating application of hapten is thought to be useful as an animal model of atopic dermatitis (*Anitex* 10, 23, 1998).

Recently, it has been reported that NC/Nga mice spontaneously develop dermatitis similar to atopic dermatitis (*Int. Immunol.* 9, 461, 1997). NC/Nga mice that are maintained in conventional, non specific pathogen free environment begin to exhibit remarkable scratching behavior and erythema after about seven to eight weeks of age, then exhibit hemorrhaging or sores or ulceration of the skin with aging. Further, they exhibit symptoms resembling the clinical observations of atopic dermatitis in humans such as drying or thickening of the skin. Other strains of mice such as BALB/c do not suffer from similar dermatitis even if made to cohabitate with NC/Nga mice, suggesting that this dermatitis is considered specific to NC/Nga mice (Saishin Igaku (*Latest Medicine*), 53, 2848, 1998). Further, when raising these mice under specific paphogen free (SPF) environment, no skin abnormalities are observed at all, raising the possibility that some sort of environmental factors are involved in the onset of dermatitis in these mice. When NC/Nga mice raised under an SPF environment are repeatedly painted with hapten, only the delayed type hypersensitivity reaction called contact dermatitis is caused in the initial period of sensitization, but with the increase in sensitization, conditions similar to atopic dermatitis are observed (*CRJ Letters* 11, 1, 1998). Therefore, while the natural stimulant for the spontaneous dermatitis in these mice is still not clear, it is clear that repeated exposure to some sort of antigen under the natural environment is an important factor. Thus, these mice are extremely useful as a model for atopic dermatitis spontaneously caused by repeated exposure to an allergen that would be present in the air.

The most effective medicament for the treatment of atopic dermatitis is a steroid ointment (*J. Allergy Clin. Immunol.* 104, S123, 1999). Use of such steroid ointment, however, requires careful selection of the medicament used according to the location of application and timing. If the method of use is not appropriate, no effect will be manifested or the condition will conversely deteriorate. Further, when a steroid ointment is used over a long period, side effects such as atrophy and rosacea occur. Further, if stopping use of this medicament mid way, the phenomenon of rebound, that is, remarkable deterioration of the skin symptoms, is sometimes observed.

In addition to steroid ointment, histamine antagonists and anti-allergic agents have been used for treatment of atopic dermatitis. Histamine antagonists are effective in the sense of eliminating ichiness, but do not lead to a cure of this disease. Anti-allergic agents such as tranilast, ketotifen, oxatomide, and azelastine hydrochloride are ineffective against conditions of atopic dermatitis, or the effect is little, if any. This is believed to be due to the fact that these drugs have a suppressive action on a type I allergic reaction, but exhibit almost no effect on the actions of eosinophils or type IV allergic reaction (*Jap. J. Pharmacol.* 63, 73, 1993, *Jap. J. Pharmacol.* 51, 93, 1989). Recently ointment of tacrolimus, an immunosuppressive, has been developed as a medicament for treatment of atopic dermatitis (*J. Allergy Clin. Immunol.* 104, S126, 1999), but various side effects due to suppression of the immunoreaction by use of this medicament cannot be avoided. Taken together, it is difficult to say that any of the existing medicaments are sufficiently satisfactory in respect to efficacy and side effects, and development of a medicament superior in efficacy and safety is desirable.

On the other hand, chymase is a serine protease stored in mast cell granules, and widely present in tissue such as the skin, heart, vascular walls, intestines, etc. (*Mast Cell Proteases in Immunology and Biology*; Caughey, G. H., Ed; Marcel Dekker, Inc.; New York, 1995). It has been reported long ago that chymase acts on rat peritoneal mast cells and causes degranulation (*J. Immunol.* 136, 3812, 1986) and that a chymase inhibitor suppresses the Ig-E demiated mast cell degranulation (*Biochem. Int.* 10, 863, 1985) and has been pointed out that chymase is involved in the function of mast cells. Recently, it has been reported that administration of human chymase induces infiltration of leukocytes including eosinophils in mice as well as guinea pigs (*Br. J. Pharmacol.* 125, 1491, 1998), that human chymase acts on the precursor of IL-1β (Interleukin 1β) and converts it to active type IL-1β (*J. Exp. Med.* 174, 821, 1991), and that human chymase has the action of partially digesting membrane-bound stem cell factor (SCF) and converting it to soluble SCF (*Proc. Natl. Acad. Sci. U.S.A.* 94, 9017, 1997), etc. These findings suggest the possibility that chymase has some sort of role in allergic diseases such as atopic dermatitis. However, it is difficult to say that the pathophysiological role of chymase has been elucidated by these studies. At the present time, an energetic search is going on for substances which can inhibit the activity of chymase in vivo with the aim of clarifying the role of chymase in various diseases and the possibility of chymase inhibitors as pharmaceuticals.

There are chymase inhibitors such as low molecular weight chymase inhibitors such as shown in textbooks (*Protease Inhibitors*; Barrett et al., Eds; Elssevier Science B.V.; Amsterdam, 1996), α-keto acid derivatives reported as peptide type inhibitors (WO93-25574, *Proc. Natl. Acad. Sci. USA*, 1995, 92, 6738), α,α-difluoro-β-keto acid derivatives (Japanese Unexamined Patent Publication (Kokai) No. 9-124691), tripeptide inhibitors (WO93-03625), phosphoric acid derivatives (Oleksyszyn et al., *Biochemistry* 30, 485, 1991), peptide like inhibitors such as trifluoromethylketone derivatives (WO96-33974, Japanese Unexamined Patent Publication (Kokai) No. 10-53579) and acetoamide derivatives (Japanese Unexamined Patent Publication (Kokai) No. 10-7661, Japanese Unexamined Patent Publication (Kokai) No. 10-53579, Japanese Unexamined Patent Publication (Kokai) No. 11-246437, WO99-41277, WO98-18794, WO96-39373), non-peptide type inhibitors such as triazine derivatives (Japanese Unexamined Patent Publication (Kokai) No. 8-208654 and Japanese Unexamined Patent Publication (Kokai) No. 10-245384), phenol ester derivatives (Japanese Unexamined Patent Publication (Kokai) No. 10-87567), cephem derivatives (Japanese Unexamined Patent Publication (Kokai) No. 10-87493), isoxazole derivatives (Japanese Unexamined Patent Publication (Kokai) No. 11-1479), imidazolidine derivatives (WO96-04248), hydantoin derivatives (Japanese Unexamined Patent Publication (Kokai) No. 9-31061), quinazoline derivatives (WO97-11941), etc. have been reported, but no satisfactory medicament or treatment method using inhibition of the activity of chymase as a strategy for treatment has yet been established.

DISCLOSURE OF THE INVENTION

The object of the present invention is to provide a side effect-free, safe medicament for prevention or treatment of dermatitis such as atopic dermatitis, which exhibits biphasic skin reaction or is induced by repeated exposure to an antigen, which suppresses the progress of the condition and improves the quality of life of the patient.

The present inventors engaged in intensive studies taking note of the fact that atopic dermatitis exhibits biphasic skin reaction and that late-phase reaction plays an important role in the condition. As a result, the present inventors discovered that a chymase inhibitor acts to alleviate the late-phase reaction in the biphasic skin reaction of dermatitis and that it is effective even against dermatitis caused by repeated exposure to an antigen, and thereby completed the present invention.

That is, according to the present invention, there is provided a medicament for prevention or treatment of dermatitis exhibiting biphasic skin reaction containing a chymase inhibitor as its effective ingredient.

According to the present invention, further, there is provided a medicament for alleviation of late-phase reaction of dermatitis exhibiting biphasic skin reaction containing a chymase inhibitor as its effective ingredient.

According to the present invention, further, there is provided a medicament for the prevention or treatment of dermatitis induced by repeated exposure to an antigen containing a chymase inhibitor as its effective ingredient.

According to the present invention, there is provided a pharmaceutical composition for the prevention or treatment of dermatitis exhibiting biphasic skin reaction containing a chymase inhibitor in an amount alleviating the late-phase reaction and a pharmaceutically acceptable vehicle.

BRIEF DESCRIPTION OF THE DRAWINGS

FIG. 1 is a graph showing the time-course of the skin reaction in Ascaris-induced mouse biphasic skin reaction in Example 2.

FIGS. 2A, 2B, and 2C are graphs showing the effects of chymase inhibitor (FIG. 2A) and control drugs, prednisolone (FIG. 2B) and diphenhydramine (FIG. 2C), in Ascaris-induced biphasic skin reaction in Example 3.

FIGS. 3A and 3B are graphs showing the time-course of the skin reaction when the human chymase (FIG. 3A) or histamine (FIG. 3B) was administered intradermally to mice in Example 4.

FIGS. 4A and 4B are graphs showing dose-dependency of chymase in the skin reaction when human chymase was administered intradermally to mice in Example 4 (FIG. 4A, 1 hour after the chymase administration, FIG. 4B after 16 hours after the chymase administration).

FIG. 6B, dermatitis induced by Ascaris extract (after 1 hour); FIG. 6C, dermatitis induced by Ascaris extract (after 24 hours), FIG. 6D, dermatitis induced by human chymase (after 1 hour); FIG. 6E dermatitis induced by human chymase (after 24 hours).

FIGS. 7A and 7B are graphs showing the skin reaction when human chymase administered intradermally to mast cell-deficient mice in Example 7 (FIG. 7A, the reaction after 1 hour; FIG. 7B the reaction after 16 hour).

FIG. 10 is a graph showing the change in chymase-like activity in the ear in the dermatitis induced by repeated application of hapten in Example 9.

FIG. 18B, chymase-injected)

FIG. 19 is a graph showing the effect of human chymase on SCF expression in human keratinocytes in vitro in Example 17.

FIGS. 20A and 20B are graphs showing the effect of a chymase inhibitor on clinical skin scores in NC/Nga mice in Example 18. FIG. 20A, at the start of the experiment; FIG. 20B, 35 days after the start of the chymase administration.

FIGS. 22A and 22B are graphs showing the effect of a chymase inhibitor on the number of skin mast cells in NC/Nga mice in Example 18. FIG. 22A, the ear; FIG. 22B, the back.

FIGS. 23A and 23B are graphs showing the effect of a chymase inhibitor on the number of skin eosinophils in NC/Nga mice in Example 18 FIG. 23A, the ear; FIG. 23B, the back.

BEST MODE FOR CARRYING OUT THE INVENTION

Figure 2A:
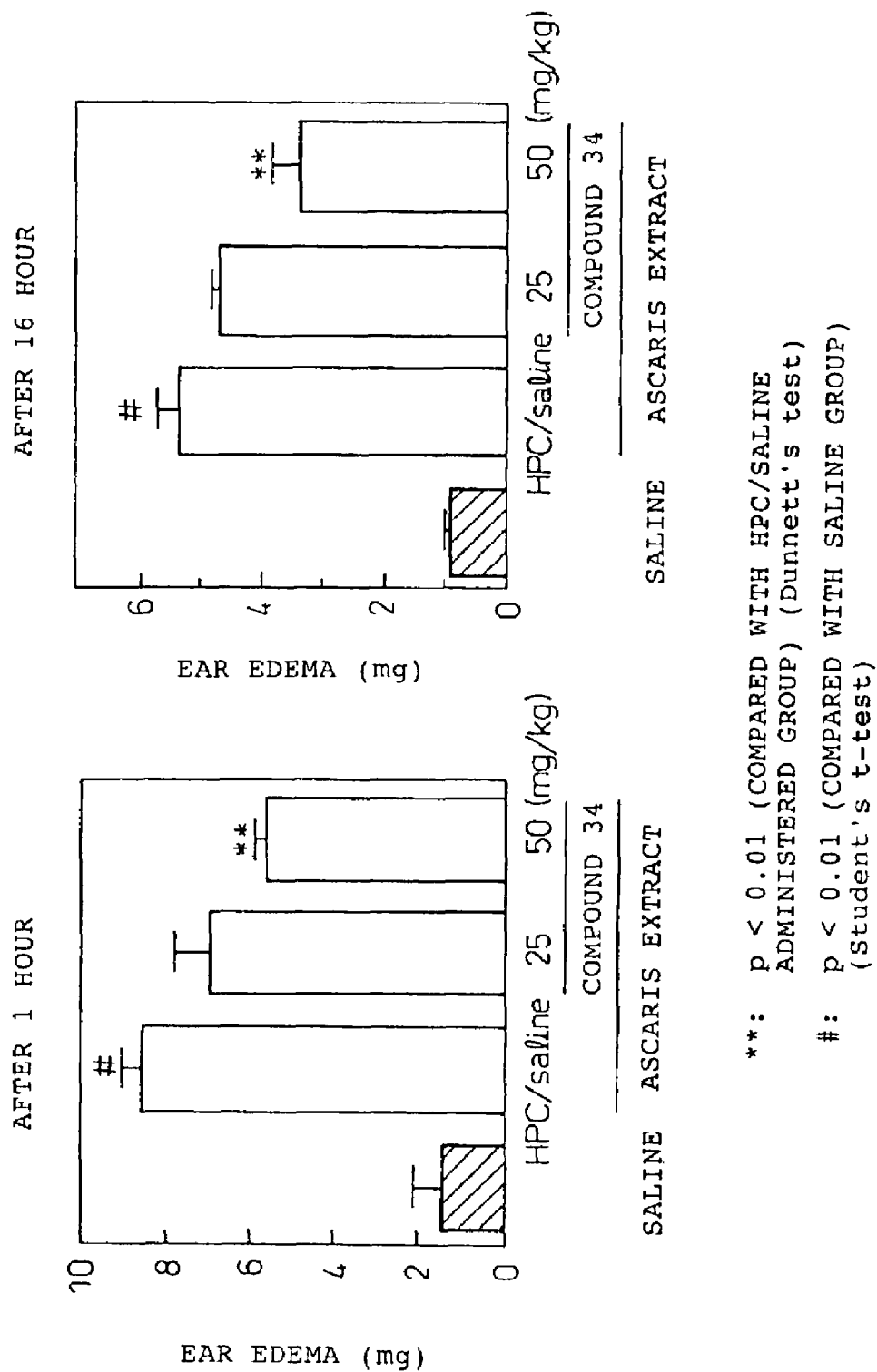

The chymase inhibitor able to be used in the present invention can be selected as a substance able to exhibit an action inhibiting the activity of chymase by the use of methods workable by persons skilled in the art. As the method of selection, for example, the method of the later explained Example 1 may be mentioned. The compounds obtained in this way include known compounds previously reported as chymase inhibitors, for example, the low molecular weight chymase inhibitors such as shown in textbooks (*Protease Inhibitors*; Barrett et al., Eds; Elssevier Science B.V.; Amsterdam, 1996), α-keto acid derivatives reported as peptide type inhibitors (WO93-25574, *Proc. Natl. Acad. Sci. USA*, 1995, 92, 6738), α,α-difluoro-β-keto acid derivatives (Japanese Unexamined Patent Publication (Kokai) No. 9-124691), tripeptide inhibitors (WO93-03625), phosphoric acid derivatives (Oleksyszyn et al., *Biochemistry* 30, 485, 1991), peptide like inhibitors such as trifluoromethylketone derivatives (WO96-33974, Japanese Unexamined Patent Publication (Kokai) No. 10-53579) and acetoamide derivatives (Japanese Unexamined Patent Publication (Kokai) No. 10-7661, Japanese Unexamined Patent Publication (Kokai) No. 10-53579, Japanese Unexamined Patent Publication (Kokai) No. 11-246437, WO99-41277, WO98-18794, WO96-39373), non-peptide type inhibitors such as triazine derivatives (Japanese Unexamined Patent Publication (Kokai) No. 8-208654 and Japanese unexamined Patent Publication (Kokai) No. 10-245384), phenol ester derivatives (Japanese Unexamined Patent Publication (Kokai) No. 10-87567), cephem derivatives (Japanese Unexamined Patent Publication (Kokai) No. 10-87493), isoxazole derivatives (Japanese Unexamined Patent Publication (Kokai) No. 11-1479), imidazolidine derivatives (WO96-04248), hydantoin derivatives (Japanese Unexamined Patent Publication (Kokai) No. 9-31061), quinazoline derivatives (WO97-11941), etc., but as a typical examples of a preferable chymase inhibitor, a compound of the following formula (I) and its pharmaceutically acceptable salts may be mentioned.

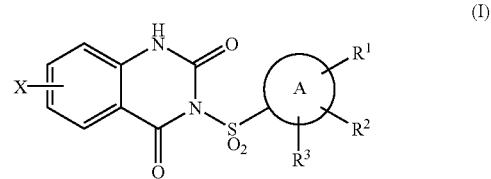

(I)

wherein, the ring A represents an aryl group;

$R^1$ represents a hydroxyl group, an amino group, a $C_1$ to $C_4$ lower alkylamino group which may be substituted with a carboxylic acid group, a $C_7$ to $C_{10}$ lower aralkylamino group which may be substituted with a carboxylic acid group, an amino group acylated with a $C_1$ to $C_4$ lower aliphatic acid which may be substituted with a carboxylic acid group, an amino group acylated with an aromatic ring carboxylic acid which may be substituted with a carboxylic acid group, an amino group acylated with a heteroaromatic ring carboxylic acid which may be substituted with a carboxylic acid group, an amino group sulfonylated with a $C_1$ to $C_4$ lower alkanesulfonic acid which may be substituted with a carboxylic acid group, an amino group sulfonylated with an aromatic ring sulfonic acid which may be substituted with a carboxylic acid group, an amino group sulfonylated with a heteroaromatic ring sulfonic acid which may be substituted with a carboxylic acid group, a $C_1$ to $C_4$ lower alkyl group substituted with a carboxylic acid group, or a $C_2$ to $C_4$ lower alkylene group which may be substituted with a carboxylic acid group;

$R^2$ and $R^3$ may be the same or different and represent a hydrogen atom, an unsubstituted or substituted $C_1$ to $C_4$ lower alkyl group, a halogen atom, a hydroxyl group, a $C_1$ to $C_4$ lower alkoxyl group, an amino group, an unsubstituted or substituted $C_1$ to $C_4$ lower alkylamino group, an unsubstituted or substituted $C_7$ to $C_{10}$ aralkylamino group, an amino group acylated with a $C_1$ to $C_4$ lower aliphatic acid which may be substituted with a carboxylic acid group, an amino group acylated with an aromatic ring carboxylic acid which may be substituted with a carboxylic acid group, an amino group acylated with a heteroaromatic ring carboxylic acid which may be substituted with a carboxylic acid group, an amino group sulfonylated with a $C_1$ to $C_4$ lower alkanesulfonic acid which may be substituted with a carboxylic acid group, an amino group sulfonylated with an aromatic ring sulfonic acid which may be substituted with a carboxylic acid group, an amino group sulfonylated with a heteroaromatic ring sulfonic acid which may be substituted with a carboxylic acid group, or a carboxylic acid group or when the ring A is a benzene ring, $R^1$ and $R^2$ may form, together with the substituting benzene ring, a fused heterocyclic ring which may be substituted with a carboxylic acid and in which the carbon atom in the ring may form a carbonyl group and $R^3$ is the same as defined above; and X represents a hydrogen atom, a $C_1$ to $C_4$ lower alkyl group, a $C_1$ to $C_4$ lower alkoxy group, a halogen atom, a hydroxyl group, an amino group, or a nitro group.

In the general formula (I), preferable examples of the aryl group represented by the ring A are a benzene ring and a naphthalene ring.

Preferable examples of the $C_1$ to $C_4$ lower alkylamino group which may be substituted with the carboxylic acid group and the $C_7$ to $C_{12}$ lower aralkylamino group which may be substituted with a carboxylic acid group represented by $R^1$ are a methylamino group, an ethylamino group, a propylamino group, a butylamino group, a carboxymethylamino group, a carboxyethylamino group, a carboxypropylamino group, a carboxybutylamino group, a benzylamino group, a phenetylamino group, a phenylpropylamino group, a phenylbutylamino group, a carboxybenzylamino group, a carboxyphenetylamino group, a carboxyphenylpropylamino group, a carboxyphenylbutylamino group, etc.

Preferable examples of the amino group acylated with a $C_1$ to $C_4$ lower aliphatic acid which may be substituted with a carboxylic acid group, the amino group acylated with an aromatic ring carboxylic acid which may be substituted with a carboxylic acid group, and the amino group acylated with a heteroaromatic ring carboxylic acid which may be substituted with a carboxylic acid group represented by $R^1$ are a formylamino group, an acetylamino group, a propionylamino group, a butyrylamino group, a benzoylamino group, a naphthoylamino group, a pyridinecarbonylamino group, a pyrrolecarbonylamino group, a carboxyacetylamino group, a carboxypropionylamino group, a carboxybutyrylamino group, a carboxybenzoylamino group, a carboxynaphthoylamino group, a carboxypyridinecarbonylamino group, a carboxypyrrolecarbonylamino group, etc.

Preferable examples of the amino group sulfonylated with a $C_1$ to $C_4$ lower alkanesulfonic acid which may be substituted with a carboxylic acid group, the amino group sulfonylated with an aromatic ring sulfonic acid which may be substituted with a carboxylic acid group, and the amino group sulfonylated with a heteroaromatic ring sulfonic acid which may be substituted with a carboxylic acid group represented by $R^1$ are a methanesulfonylamino group, an ethanesulfonylamino group, a propanesulfonylamino group, a butanesulfonylamino group, a benzenesulfonylamino group, a naphthalenesulfonylamino group, a pyridinesulfonylamino group, a pyrrolesulfonylamino group, a carboxymethanesulfonylamino group, a carboxyethanesulfonylamino group, a carboxypropanesulfonylamino group, a carboxybutane-sulfonylamino group, a carboxybenzenesulfonylamino group, a carboxynaphthalenesulfonylamino group, a carboxypyridinesulfonylamino group, a carboxypyrrolesulfonylamino group, etc.

Preferable examples of the $C_1$ to $C_4$ lower alkyl group substituted with a carboxylic acid group represented by $R^1$ are an acetic acid group, a propionic acid group, a butyric acid group, a valeric acid group, etc.

Preferable examples of the $C_2$ to $C_4$ lower alkylene group substituted with a carboxylic acid group represented by $R^1$ are an acrylic acid group, a crotonic acid group, etc.

Preferable examples of the unsubstituted or substituted $C_1$ to $C_4$ lower alkyl group represented by $R^2$ or $R^3$ are a straight-chain alkyl group such as a methyl group, an ethyl group, a n-propyl group, and a n-butyl group and a branched alkyl group such as an isopropyl group, a sec-butyl group, and a t-butyl group.

Preferable examples of the substituent group of the $C_1$ to $C_4$ lower alkyl group are a carboxylic acid group, a halogen atom such as a fluorine atom and a chlorine atom, a $C_1$ to $C_4$ lower alkoxy group, an amino group, a methylamino group, a dimethylamino group, a carboxymethylamino group, a carboxyethylamino group, etc.

Preferable examples of the halogen atom represented by $R^2$ or $R^3$ are a fluorine atom, a chlorine atom, a bromine atom and an iodine atom.

Preferable examples of the $C_1$ to $C_4$ lower alkoxyl group represented by $R^2$ or $R^3$ are a straight-chain alkyloxy group such as a methoxy group, an ethoxy group, a n-propyloxy group, and a n-butoxy group and a branched alkyloxy group such as an isopropyloxy group, a sec-butoxy group, and a t-butoxy group.

Preferable examples of the unsubstituted or substituted $C_1$ to $C_4$ lower alkylamino group represented by $R^2$ or $R^3$ are a methylamino group, an ethylamino group, a propylamino group, a butylamino group, etc.

Preferable examples of the substituent group of the $C_1$ to $C_4$ lower alkylamino group are a carboxylic acid group, a halogen atom such as a fluorine atom and a chlorine atom, a $C_1$ to $C_4$ lower alkoxyl group, etc.

Preferable examples of the unsubstituted or substituted $C_7$ to $C_{12}$ lower aralkylamino group represented by $R^2$ or $R^3$ are a benzylamino group, a phenetylamino group, a phenylpropylamino group, a phenylbutylamino group, etc.

Preferable examples of the substituent group of the aralkylamino group are a carboxylic acid group, a halogen atom such as a fluorine atom and a chlorine atom, a $C_1$ to $C_4$ lower alkoxyl group, etc.

Preferable examples of the amino group acylated with a $C_1$ to $C_4$ lower aliphatic acid which may be substituted with a carboxylic acid group, the amino group acylated with an aromatic ring carboxylic acid which may be substituted with a carboxylic acid group, and the amino group acylated with a heteroaromatic ring carboxylic acid which may be substituted with a carboxylic acid group represented by $R^2$ or $R^3$ are a formylamino group, an acetylamino group, a propionylamino group, a butyrylamino group, a benzoylamino group, a naphthoylamino group, a pyridinecarbonylamino group, a pyrrolecarbonylamino group, a carboxyacetylamino group, a carboxypropionylamino group, a carboxybutyrylamino group, a carboxybenzoylamino group, a carboxynaphthoylamino group, a carboxypyridinecarbonylamino group, a carboxypyrrolecarbonylamino group, etc.

Preferable examples of the amino group sulfonylated with a $C_1$ to $C_4$ lower alkanesulfonic acid which may be substituted with a carboxylic acid group, the amino group sulfonylated with an aromatic ring sulfonic acid which may be substituted with a carboxylic acid group, and the amino group sulfonylated with a heteroaromatic ring sulfonic acid which may be substituted with a carboxylic acid group represented by $R^2$ or $R^3$ are a methanesulfonylamino group, an ethanesulfonylamino group, a propanesulfonylamino group, a benzenesulfonylamino group, a naphthalenesulfonylamino group, a pyridinesulfonylamino group, a pyrrolesulfonylamino group, a carboxymethanesulfonylamino group, a carboxyethanesulfonylamino group, a carboxypropanesulfonylamino group, a carboxybenzenesulfonylamino group, a carboxynaphthalenesulfonylamino group, a carboxypyridine-sulfonylamino group, a carboxypyrrolesulfonylamino group, etc.

Preferable examples of the fused heterocyclic ring which may be substituted with a carboxylic acid and in which the carbon atom in the ring may form a carbonyl group which $R^1$ and $R^2$ form together with the substituting benzene ring when the ring A is a benzene ring, are a tetrahydroquinoline ring and a benzoxazine ring, for example, a tetrahydroquinoline, a benzoxazine, a quinoxaline, a benzodioxane, a carboxytetrahydroquinoline, a carboxybenzoxazine, a carboxyquinoxaline, a carboxybenzodioxane, etc.

Preferable examples of the $C_1$ to $C_4$ lower alkyl group represented by X are a straight-chain alkyl group such as a methyl group, an ethyl group, a n-propyl group, and a n-butyl group and a branched alkyl group such as an isopropyl group, a sec-butyl group, and a t-butyl group.

Preferable examples of the $C_1$ to $C_4$ lower alkoxyl group represented by x are a straight-chain alkyloxy group such as a methoxy group, an ethoxy group, a n-propyloxy group, and a n-butoxy group and a branched alkyloxy group such as an isopropyloxy group, a sec-butoxy group, and a t-butoxy group.

Preferable examples of the halogen atom represented by x, are a fluorine atom, a chlorine atom, a bromine atom and an iodine atom.

Further, examples of a pharmaceutically acceptable salts are an acid salt such as a hydrochloric acid salt, a methanesulfonic acid salt, and a trifluoroacetic acid salt and an alkali metal salt such as a sodium salt and a potassium salt.

The other typical examples of the preferable chymase inhibitor are a quinazoline derivative having the formula (II) and its pharmaceutically acceptable salts:

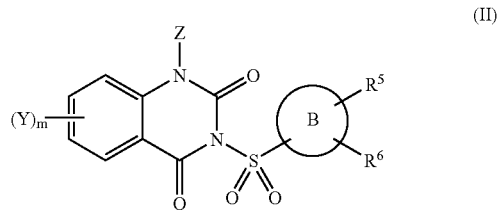

wherein, the ring B represents a benzene ring, a pyridine ring, a pyrrole ring, or a pyrazole ring, m represents 0, 1, or 2, Y represents a hydroxy group, a nitro group, a halogen atom, a $C_1$ to $C_4$ lower alkyl group which may be substituted with a halogen atom, a $C_1$ to $C_4$ lower alkoxy group which may be substituted with a halogen atom, or a $C_7$ to C12 aralkyloxy group, or Y represents a group forming a naphthalene ring or a quinoline ring together with the benzene ring which is shown as substituted with said Y, $R^5$ and $R^6$ are the same or different and represent a hydrogen atom, a halogen atom, a $C_1$ to $C_4$ lower alkyl group which may be substituted with a halogen atom, a nitro group, a cyano group, a pyrazolyl group, a tetrazolyl group, a carboxyl group which may be esterified with a $C_1$ to $C_4$ lower alkyl group or an allyl group, or a $C_1$ to $C_4$ lower alkoxy group which may be substituted with one or more substituent groups selected from the group consisting of a halogen atom, a morpholino group, a phenylpiperazinyl group, and a carboxyl group which may be esterified with a $C_1$ to $C_4$ lower alkyl group or an allyl group, or, when the ring B represents a benzene ring, $R^5$ and $R^6$ represent a group forming a naphthalene ring or a quinoline ring together with the benzene ring which is shown as substituted with said $R^5$ and $R^6$, and Z represents a hydrogen atom, a $C_1$ to $C_4$ lower alkyl group which may be substituted with a halogen atom, a $C_2$ to $C_5$ alkenyl group, an unsubstituted or substituted aralkyl group, an unsubstituted or substituted aromatic heterocyclic alkyl group, a carboxylmethyl group which may be esterified with a $C_1$ to $C_4$ lower alkyl group or an allyl group, a carbonylmethyl group which is amidated with a primary or secondary or cyclic amine, an unsubstituted or substituted arylcarbonylmethyl group, or an unsubstituted or substituted aralkyloxymethyl group.

In the general formula (II), the preferable examples of the halogen atom for Y are fluorine, chlorine, bromine, or iodine. The examples of the lower alkyl group of the $C_1$ to $C_4$ lower alkyl group for Y, which is substituted with a halogen atom, are straight chain alkyl groups such as a methyl group, ethyl group, n-propyl group and n-butyl group, and branched alkyl groups such as an isopropyl group, sec-butyl group and t-butyl group, and, while the examples of the halogen atom of the $C_1$ to $C_4$ lower alkyl group for Y which is substituted with a halogen atom, are fluorine, chlorine, bromine and iodine. The examples of the lower alkoxy group of the $C_1$ to $C_4$ lower alkoxy group for Y, which is substituted with a halogen atom, are straight chain alkoxy groups such as a methoxy group, ethoxy group, n-propoxy group and n-butoxy group, and branched alkoxy groups such as an isopropoxy group, sec-butoxy group and t-butoxy group, while the examples of the halogen atom of the $C_1$ to $C_4$ lower alkoxy group for Y, which is substituted with a halogen atom, are fluorine, chlorine, bromine, and iodine. The examples of the $C_7$ to $C_{12}$ aralkyloxy group for Y are a benzyloxy group, phenethyloxy group, phenylpropoxy group and naphthylethyloxy group, etc, preferably the benzyloxy group.

The preferable examples of the halogen atom for $R^5$ or $R^6$ are fluorine, chlorine, bromine, or iodine. The examples of the lower alkyl group of the $C_1$ to $C_4$ lower alkyl group for $R^5$ or $R^6$, which is substituted with a halogen atom, are straight chain alkyl groups such as a methyl group, ethyl group, n-propyl group and n-butyl group, and branched alkyl groups such as an isopropyl group, sec-butyl group and t-butyl group, while the examples of the halogen atom of the $C_1$ to $C_4$ lower alkyl group for $R^5$ or $R^6$, which is substituted with a halogen atom, are fluorine, chlorine, bromine, or iodine. The preferable examples of the $C_1$ to $C_4$ lower alkyl group of the carboxyl group for $R^5$ or $R^6$, which may be esterified with the $C_1$ to $C_4$ lower alkyl group or an allyl group, are straight chain alkyl groups such as a methyl group, ethyl group, n-propyl group and n-butyl group, and branched alkyl groups such as an isopropyl group, sec-butyl group and t-butyl group. The examples of the alkoxy group of the $C_1$ to $C_4$ lower alkoxy group for $R^1$ or $R^6$, which is substituted with one or more substituent groups 1selected from the group consisting of a halogen atom, a morpholino group, a phenylpiperazinyl group, and a carboxyl group which may be esterified with a $C_1$ to $C_4$ lower alkyl group or an allyl group, are straight chain alkoxy groups such as a methoxy group, ethoxy group, n-propoxy group and n-butoxy group, and branched alkoxy groups such as an isopropoxy group, sec-butoxy group and t-butoxy group. The examples of the halogen atom shown as the above substituent group, are fluorine, chlorine, bromine, or iodine and the preferable examples of the $C_1$ to $C_4$ lower alkyl group of the carboxyl group which is esterified with a $C_1$ to $C_4$ lower alkyl group or an allyl group shown as the above substituent group, are a methyl group, ethyl group, n-propyl group, n-butyl group, and other straight chain alkyl groups and an isopropyl group, sec-butyl group, t-butyl group, and other branched alkyl groups.

The examples of the lower alkyl group of the $C_1$ to $C_4$ lower alkyl group shown as Z which may be substituted with halogen, are straight chain alkyl groups such as a methyl group, ethyl group, n-propyl group and n-butyl group, and branched alkyl groups such as an isopropyl group, sec-butyl group and t-butyl group, while the examples of the halogen atom of the $C_1$ to $C_4$ lower alkyl group which may be substituted with the halogen atom are fluorine, chlorine, bromine, or iodine. The examples of the $C_2$ to $C_5$ alkenyl group for Z are an allyl group, propenyl group, isopropenyl group, butenyl group, etc.

The examples of the aralkyl group of an unsubstituted or substituted aralkyl group shown as Z are a $C_7$ to $C_{12}$ aralkyl group, preferably a benzyl group, phenethyl group, phenylpropyl group, or naphthylethyl group. The preferable examples of the substituent group of an unsubstituted or substituted aralkyl group are a carboxyl group which may be esterified with a $C_1$ to $C_4$ lower alkyl group or an allyl group, a cyano group, a nitro group, a carbonyl group amidized with primary amine, an amine group which may be amidized with a carboxylic acid or an amino acid, and a guanidino group which may be substituted with a lower alkoxycarbonyl group. The examples of the lower alkyl group of the carboxyl group, which may be esterified with a $C_1$ to $C_4$ lower alkyl group or an allyl group are straight alkyl groups such as a methyl group, ethyl group, n-propyl group and n-butyl group, and branched alkyl groups such as an isopropyl group, sec-butyl group and t-butyl group. The examples of the primary amine of the carbonyl group amidized with primary amine are a chain $C_1$ to $C_4$ lower alkylamine or those which may be substituted with carboxyl group, such as, preferably, methylamine, ethylamine, isopropylamine and carboxylmethylamine; amines having monocyclic or polycyclic aromatic hydrocarbon group such as aniline and naphthylamine; amines having aromatic heterocyclic group such as aminopyridine, aminopyrrole, and other. The examples of the carboxylic acid of the amine group which may be amidized with a carboxylic acid or an amino acid are preferably $C_2$ to $C_5$ aliphatic monocarboxylic acids or aliphatic dicarboxylic acids such as pivalic acid and succinic acid, while the examples of the amino acid are amino acids, of which carboxyl group may be esterified or of which amine group may be amidized, such as L-aspartic acid, α-O-t-butyl-N-t-butoxycarbonyl-L-aspartic acid and other. The examples of the guanidino group which may be substituted with a lower alkoxycarbonyl group are preferably a guadinino group which may be substituted with a $C_2$ to $C_5$ lower alkoxycarbonyl group such as a guanidino group and 2, 3-bis-t-butoxycarbonylguanidino group.

The examples of the aromatic heterocyclic alkyl group of an unsubstituted or substituted aromatic heterocyclic alkyl group shown as Z are thienylalkyl groups such as a 2-thenyl group and a 2-thienylethyl group, furylalkyl groups such as a 2-furfuryl group and a 2-furylethyl group, pyridylalkyl groups such as a 2-pyridylmethyl group, 3-pyridylmethyl group, 4-pyridylmethyl group and 4-pyridylethyl group, pyrimidinylalkyl groups such as a 5-pyrimidinylmethyl group, pyrazinylalkyl groups such as a 2-pyrazinylmethyl group, pyridazinylalkyl groups such as a 3-pyridazinylmethyl group tetrazolylalkyl groups such as a 5-tetrazolylmethyl group, isothiazolylalkyl groups such as a 4-isothiazolylmethyl group and a 5-isothiazolylmethyl group, thiazolylalkyl groups such as a 5-thiazolylmethyl group, oxazolylalkyl groups such as a 5-oxazolylmethyl group, and isoxazolylalkyl groups such as a 4-isooxazolylmethyl group and 5-isoxazolylmethyl group. The preferable examples of the substituent group of an unsubstituted or substituted heterocyclic alkyl group, are $C_1$ to $C_4$ lower alkyl groups such as a methyl group and ethyl group, and $C_1$ to $C_4$ carboxyl lower alkyl groups such as a carboxylmethyl group and carboxylethyl group.

The examples of the lower alkyl group of the carboxymethyl group which may be esterified with a $C_1$ to $C_4$ lower alkyl group or an allyl group shown as Z are straight chain alkyl groups such as a methyl group, ethyl group, n-propyl group and n-butyl group, and branched alkyl groups such as an isopropyl group, sec-butyl group and t-butyl group.

The examples of the primary amine of the carbonylmethyl group which may be amidized with primary or secondary or cyclic amine shown as Z are chain $C_1$ to $C_4$ lower alkylamines or those which may be substituted with a carboxyl group such as preferably methylamine, ethylamine, isopropylamine and carboxylmethylamine, and amines having monocyclic saturated hydrocarbon group such as a cyclohexylamine, and amines having monocyclic or polycyclic aromatic hydrocarbon group such as aniline, a benzylamine and a naphthylamine, and amines having aromatic heterocyclic group such as an aminopyridine, an aminomethylpyridine, an aminopyrrole, an aminopyrimidine, an aminoindole and aminoquinoline, wherein the amines having aromatic hydrocarbon group or aromatic heterocyclic group may have on its ring one or more substituent such as 1) hydroxy group,
2) —OPO(OH)$_2$,
3) amino group,
4) oxo group,
5) halogen atom,
6) carboxyl group, which may be esterified with $C_1$ to $C_4$ lower alkyl group such as a methyl group, an ethyl group, an isopropyl group and a t-butyl group, or an allyl group, 7) straight chain or branched $C_1$ to $C_4$ lower alkoxy group such as a methoxy group, an ethoxy group, a n-propoxy group and t-butoxy group, which may be substituted with a carboxyl group, which may be esterified with a C, to $C_4$ lower alkyl group such as a methyl group, an ethyl group, an isopropyl group and a t-butyl group, or an allyl group, 8) straight chain or branched $C_1$ to $C_4$ lower alkyl groups such as a methyl group, an ethyl group, a n-propyl group, a n-butyl group, an isopropyl group, a sec-butyl group, and t-butyl group, which may be substituted.

Further, the preferable examples of the substituent of the $C_1$ to $C_4$ lower alkyl group, which may be substituted, of the above 8), a) a carboxyl group, which may be esterified with $C_1$ to $C_4$ lower alkyl group such as a methyl group, an ethyl group, an isopropyl group and a t-butyl group, or an allyl group, b) piperadinyl group, which may be N-substituted with carboxy group which is esterified with $C_1$ to $C_4$ lower alkyl group such as a methyl group, an ethyl group, an isopropyl group and a t-butyl group, or an allyl group, c) morpholino group, and d) amino group which may be amidized with carboxylic acid or amino acid The examples of the carboxylic acid of amino group of the above d), which may be amidized with carboxylic acid or amino acid, are preferably $C_2$ to $C_5$ aliphatic mono- or di-carboxylic acids such as pivalic acid and succinic acid, while the examples of the amino acid are amino acids of which carboxyl group may be esterified or of which amino group may be amidized, such as a L-aspartic acid, an α-O-t-butyl-N-t-butoxycarbonyl-L-aspartic acid, and a β-O-t-butyl-N-t-butoxycarbonyl-L-aspartic acid. Further, the amine having aromatic heterocyclic group may have the nitrogen atom on its ring, which may be substituted with $C_1$ to $C_4$ lower alkyl group such as a methyl group, and an ethyl group, or carboxy lower alkyl group, which may be esterified, such as a carboxylmethyl group and a t-butoxy carbonylmethyl group.

The examples of the secondary amine of the carbonylmethyl group shown as Z, which is amidized with primary or secondary or cyclic amine are di-lower alkylamines such as a dimethylamine and diethylamine. The examples of the cyclic amine of the carbonylmethyl group shown as Z, which is amidized with primary or secondary or cyclic amine are pyrrolidine and piperidine.

The examples of the arylcarbonylmethyl group of the unsubstituted or substituted arylcarbonylmethyl group shown as Z are a phenylcarbonylmethyl group and a naphthylcarbonylmethyl group, while the preferable examples of the substituent group are a hydroxy group, a nitro group, halogen atoms such as fluorine, chlorine, bromine and iodine, straight or branched $C_1$ to $C_4$ lower alkyl groups, which may be substituted with halogen atom such as methyl group, ethyl group, n-propyl group, n-butyl group, isopropyl group, sec-butyl group and t-butyl group, straight or branched $C_1$ to $C_4$ lower alkoxy groups, which may be substituted with halogen atom, such as methoxy group, ethoxy group, n-propoxy group, n-butoxy group, isopropoxy group, sec-butoxy group and t-butoxy group.

The examples of the aralkyloxymethyl group of the unsubstituted or substituted aralkyloxymethyl group shown as Z, are preferably $C_8$ to $C_{13}$ aralkyloxymethyl groups such as a benzyloxy methyl group, phenethyloxymethyl group and naphthylethyloxymethyl group, while the preferable examples of the substituent group are a hydroxy group, a nitro group, halogen atoms such as fluorine, chlorine, bromine and iodine, straight or branched $C_1$ to $C_4$ lower alkyl groups which may be substituted with halogen atom, such as methyl group, ethyl group, n-propyl group, n-butyl group, isopropyl group, sec-butyl group and t-butyl group, straight or branched $C_1$ to $C_4$ lower alkoxy groups, which may be substituted with halogen atom, such as methoxy group, ethoxy group, n-propoxy group, n-butoxy group, isopropoxy group, sec-butoxy group and t-butoxy group.

Further, the examples of a pharmaceutically acceptable salt are acid salts such as a chlorate and nitrate and alkali metal salts such as a sodium salt, potassium salt.

The quinazoline derivative having the formula (I) according to the present invention may, for example, be synthesized by the following Synthesis Method (A) or (B).

Synthesis Method (A)

A compound having the formula (I-1):

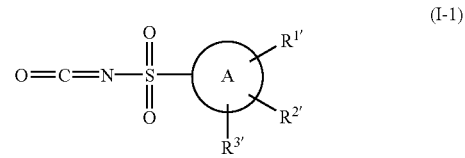

(I-1)

wherein the ring A is the same as defined above and $R^{1'}$, $R^{2'}$ and $R^{3'}$ represent $R^1$, $R^2$ and $R^3$, which may be protected with a protecting group, respectively, and $R^1$, $R^2$ and $R^3$ represent the same as defined above is reacted with an anthranilic acid derivative having the formula (I-2):

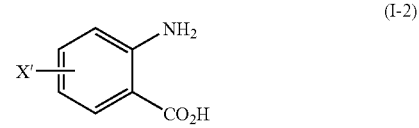

(I-2)

wherein X' represents X, which may be protected with a protecting group, and X represents the same as defined above using the method described, for example, in JP-A-6-199839 to obtain a sulfonylurea derivative having the formula (I-3):

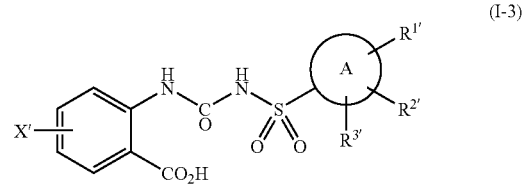

(I-3)

wherein the ring A, $R^{1'}$, $R^{2'}$, $R^{3'}$ and X' represent the same as defined above, then, a condensing agent for example, 1,1'-carbonyldiimidazole (hereinafter referred to as CDI) is used to obtain the quinazoline ring, and if necessary, the protecting groups of $R^1$, $R^2$, $R^3$ and X are deprotected.

In this reaction, when $R^1$, $R^2$ or $R^3$ represents a group containing a hydroxyl group, an amino group, or a carboxylic acid group, $R^1$, $R^2$ or $R^3$ may be optionally protected by a protecting group such as a benzyloxycarbonyl group, a t-butoxycarbonyl group, a benzyl group, an allyl group, a t-butyl group, etc. When X represents a hydroxyl group or an amino group, X may be optionally protected with a protecting group such as a benzyloxycarbonyl group, a t-butoxycarbonyl group, a benzyl group, an allyl group, a t-butyl group, etc.

The compound having the formula (I-1) used in this reaction includes a commercially available or known compound or a compound which can be synthesized by a known method may be used. For example, using the synthesis method described in the specification of European Patent No. 0269141, it is possible to use a compound which can be synthesized from the corresponding sulfonamide derivative using chlorosulfonyl isocyanate. For example, it is possible to use 3-allyloxycarbonyl-methylbenzenesulfonyl isocyanate, 4-allyloxycarbonyl-methylbenzenesulfonyl isocyanate, 4-allyloxybenzenesulfonyl isocyanate, etc.

As the anthranilic acid derivative having the formula (I-2) used for this reaction, a commercially available or known compound or a compound which can be synthesized by a known method may be used. For example, anthranilic acid, 4-chloroanthranilic acid, 4-methoxyanthranilic acid, 5-chloroanthranilic acid, 4-hydroxyanthranilic acid, etc. may be used.

The reaction to obtain the quinazoline ring from the sulfonylurea derivative having the formula (I-3) may be carried out using an aprotonic solvent such as, for example, an ether solvent such as tetrahydrofuran and dioxane, a halogen-containing solvent such as methylene chloride, or dimethylformamide etc. at a temperature of −50° C. to 50° C., preferably −20° C. to room temperature. Further, for the cyclization reaction, it is possible to use an ordinary condensing agent which includes, for example, CDI, dicyclohexylcarbodiimide, and similar carbodiimide compounds, mixed anhydrides, etc. The deprotecting reaction can be carried out by an ordinary method using hydrolysis with an acid or alkali, reduction or oxidation etc.

Synthesis Method (B)

A compound having the formula (I-4):

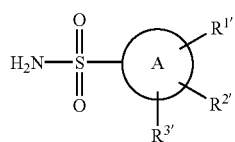

(I-4)

wherein the ring A, $R^{1'}$, $R^{2'}$ and $R^{3'}$ represent the same as defined above
is condensed with an anthranilic acid derivative having the formula (I-5):

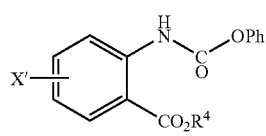

(I-5)

wherein X' represents the same as defined above, Ph represents a phenyl group, and $R^4$ represents a protecting group of the carboxyl group, which is specifically a group capable of being released by hydrolysis or hydrogenolysis, such as, for example, a methyl group, an ethyl group, or a benzyl group
using, for example, 1,8-diazabicyclo[5,4,0]-7-undecene (hereinafter referred to as DBU) to form a sulfonylurea derivative having the formula (I-6):

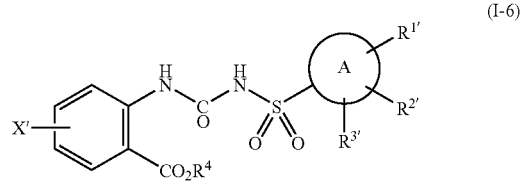

(I-6)

wherein the ring A, $R^{1'}$, $R^{2'}$, $R^{3'}$, $R^4$ and X' are the same as defined above,
which is then hydrolyzed with an alkali or hydrogenolyzed to derive a corresponding carboxylic acid represented by the formula (I-3), then the quinazoline ring is obtained and optionally the protecting groups of $R^1$, $R^2$, $R^3$ and X are deprotected, in the same way as in Synthesis Method (A). In this reaction, when $R^1$, $R^2$ or $R^3$ represents a group containing a hydroxyl group, an amino group, or a carboxylic acid group, $R^1$, $R^2$ or $R^3$ may be optionally protected by a protecting group such as a benzyloxycarbonyl group, a t-butoxycarbonyl group, a benzyl group, an allyl group, a t-butyl group, etc. when x represents a hydroxyl group or an amino group, X may be optionally protected with a protecting group such as a benzyloxycarbonyl group, a t-butoxycarbonyl group, a benzyl group, an allyl group, a t-butyl group, etc.

As the compound having the formula (I-4) used in the reaction, a commercially available or known compound or a compound which can be synthesized by a known method may be used. For example, 3-hydroxybenzenesulfonamide, 2-aminobenzenesulfonamide, 3-aminobenzenesulfonamide, 4-aminobenzenesulfonamide, (±)-2-(4-aminosulfonylphenyl)butyric acid, 3-benzyloxycarbonylamino-4-chlorobenzenesulfonamide, 4-benzyloxycarbonylamino-3-chlorobenzenesulfonamide, 4-amino-3,5-dichlorobenzenesulfonamide, 3-benzyloxycarbonylamino-4-methylbenzenesulfonamide, 4-t-butoxycarbonyl-3-hydroxybenzenesulfonamide, 3-benzyloxycarbonylamino-4-t-butoxycarbonylbenzenesulfonamide, 4-t-butoxycarbonyl-3-hydroxybenzenesulfonamide, 3-t-butoxycarbonyl-4-hydroxybenzenesulfonamide, 3-acetamide-4-methoxybenzenesulfonamide, 3-(3-aminosulfonyl)phenylacrylic acid t-butylester, 3-amino-4-methoxybenzenesulfonamide, 4-methoxy-3-methylsulfonylaminobenzenesulfonamide, 3-carboxy-4-hydroxy-2-naphthalenesulfonamide, 4-benzyloxycarbonylamino-3-t-butoxycarbonylbenzenesulfonamide, (±)-3-t-butoxycarbonyl-2-oxo-1H,3H-quinoline-7-sulfonamide, (±)-2-t-butoxycarbonyl-3-oxo-1,4-benzoxazine-6-sulfonamide, etc. may be used.

As the anthranilic acid derivative having the formula (I-5) used in this reaction, a commercially available or known compound or a compound which can be synthesized by a known method may be used. For example, methyl 4-chloro-2-N-phenoxycarbonylanthranilate, ethyl 4-chloro-2-N-phenoxycarbonylanthranilate, benzyl 4-chloro-2-N-phenoxycarbonylanthranilate, methyl 5-chloro-2-N-phenoxycarbonylanthranilate, ethyl 5-chloro-2-N-phenoxycarbonylanthranilate, benzyl 5-chloro-2-N-phenoxycarbonylanthranilate, methyl 4-methoxy-2-N-phenoxycarbonylanthranilate, ethyl 4-methoxy-2-N-phenoxycarbonylanthranilate, benzyl 4-methoxy-2-N-phenoxycarbonylanthranilate, methyl 4-hydroxy-2-N-phenoxycarbonylanthranilate, ethyl 4-hydroxy-2-N-phenoxycarbonylanthranilate, benzyl 4-hydroxy-2-N-phenoxycarbonylanthranilate, etc. may be used.

The reaction for obtaining the compound having the formula (I-4) and the anthranilic acid derivative having the formula (I-5) condense to obtain a sulfonylurea derivative having the formula (I-6), may be carried out using an aprotic solvent, for example, an ether solvent such as tetrahydrofuran or dioxane, a halogen-containing solvent such as methylene chloride, or dimethylformamide etc. at a temperature of −50° C. to 50° C., preferably −20° C. to room temperature. Further, as the usable for the condensation reaction, an organic strong base such as DBU, inorganic bases such as potassium carbonate, sodium carbonate, potassium hydroxide, and sodium hydroxide, or metal bases such as sodium hydride may be used.

In the reaction for alkali hydrolysis or hydrogenolysis of the sulfonylurea derivative having the formula (I-6) thus obtained to obtain the sulfonylurea derivative having the formula (I-3), ordinary hydrolysis conditions or hydrogenolysis conditions for esters may be used.

Note that the above reaction may be carried out while protecting the functional groups not involved in the reaction. According to the type of the protecting group, the protection is removed by chemical reduction or other ordinary protection-removing reactions. For example, when the protecting group is a t-butyl group or t-butoxycarbonyl group, trifluoroacetic acid may be used, while when it is an allyl group, palladium catalysts such as tetrakis(triphenylphosphine)palladium (0) may be used.

The compound having the formula (I), wherein $R^1$ represents an amino group acylated with a $C_1$ to $C_4$ lower aliphatic acid which may be substituted with a carboxylic acid, an amino group acylated with an aromatic ring carboxylic acid which may be substituted with a carboxylic acid and an amino group acylated with an heteroaromatic ring carboxylic acid which may be substituted with a carboxylic acid, can be obtained from the compound having the formula (I), wherein $R^1$ represents an amino group, by acylating the same with carboxylic acid, carboxylic acid chloride, carboxylic acid anhydride using an ordinary method.

The compound having the formula (I), wherein $R^1$ represents an amino group sulfonylated with a $C_1$ to $C_4$ lower alkane sulfonic acid which may be substituted with a carboxylic acid, an amino group sulfonylated with an aromatic ring sulfonic acid which may be substituted with a carboxylic acid and an amino group sulfonylated with an heteroaromatic ring sulfonic acid which may be substituted with a carboxylic acid, can be obtained from the compound having the formula (I), wherein $R^1$ represents an amino group, by sulfonylating the same with sulfonic acid or sulfonic acid chloride using an ordinary method.

A compound of formula (II) of the present invention may be obtained by a similar method to the above and further is as described in more detail in International Publication WO97/11941.

A compound of the formula (I) or (II) obtained may be purified by a conventional method such as recrystallization or column chromatography.

Further, as necessary, the compound of the formula (I) or (II) obtained by the above process may be converted into a salt by causing it to react with various types of acids or bases. As the acid able to be used to convert the compound of formula (I) or (II) to a salt, an inorganic acid such as hydrochloric acid, hydrobromic acid, nitric acid, sulfuric acid, or phosphoric acid and an organic acid such as methanesulfonic acid, benzenesulfonic acid, p-toluene sulfonic acid, trifluoroacetic acid, citric acid, lactic acid, maleic acid, fumaric acid, tartaric acid, acetic acid, adipic acid, palmitic acid, and tannic acid may be mentioned.

As the base able to be used for converting the compound of formula (I) or (II) into a salt, sodium hydroxide, lithium hydroxide, and potassium hydroxide may be mentioned.

The compounds having the formula (I) or (II) include ones containing asymmetric centers. It is possible to isolate a single optically active substance from the racemic mixture by one or more methods. For example, (1) the method of using an optically active column (2) the method of conversion to a salt by an optically active acid or base and then recrystallization (3) the method combining the above (1) and (2) may be used.

These compounds may be evaluated for action in preventing or alleviating conditions of dermatitis exhibiting biphasic skin reaction and dermatitis induced, by repeated exposure to an antigen by the later explained methods of Examples 3, 8, 10, 11, 12, and 18.

When using a compound according to the present invention as a medicament for the prevention or treatment of dermatitis exhibiting biphasic skin reaction, a medicament for the alleviation of the late-phase reaction of dermatitis exhibiting biphasic skin reaction, or a medicament for prevention or treatment of dermatitis induced by repeated exposure to an antigen, for example it is possible to use one type or a mixture of two or more types of the compound of the present invention to make a preparation of a form suitable for the method of administration according to an ordinary method. For example, examples of preparation forms for oral administration include capsules, tablets, granules, fine granules, syrups, dry syrups, and other preparations, while examples of preparation forms for non-oral administration include injections and also suppositories such as rectal suppositories and vaginal suppositories, transnasal preparations such as sprays and ointments, and transdermal preparations such as tapes for transdermal absorption.

The clinical dose of the compound according to the present invention varies according to the symptoms, severity, age, presence of complications, etc. and also varies according to the form of preparation. In the case of oral administration, however, it may be dosed usually, in terms of effective ingredients, as 1 to 1000 mg per adult per day. In the case of non-oral administration, it is sufficient to administer $\frac{1}{10}$ to $\frac{1}{2}$ the amount of the case of oral administration. These dosages can be suitably adjusted according to the age, symptoms, etc. of the patient.

In the present invention, the chymase inhibitor can be administered alone as it is without being mixed with another effective ingredient, but considering the disease in question, the symptoms, complications, etc., it may also administered as a medicinal preparation containing other effective ingredients. Further, it may also be combined with these other effective ingredients. The amounts of the other effective ingredients used are not particularly limited, but are determined considering the minimum amounts for expression of their effects alone, the occurrence of side effects, etc.

In treatment, the form of preparation and the method of combined treatment including preparations containing the chymase inhibitor alone as an effective ingredient and preparations also containing other effective ingredients are suitably selected by a physician in accordance with the age of the patient, the symptoms, etc.

The toxicity of the compound according to the present invention is low. The acute toxicity value $LD_{50}$ at 24 hours after oral administration to 5-week old male mice was 1 g/kg or more. This value is more than 50 times the anticipated clinical dosage. The compound is therefore judged to be high in safety.

EXAMPLES

The present invention will now be further explained by, but is by no means limited to, the following Examples, but the scope of the invention is not limited to these Examples needless to say.

In Example 2 and Example 3, a mouse model of dermatitis exhibiting biphasic skin reaction was used to show the usefulness of a chymase inhibitor by showing the effect of suppression of the chymase inhibitor. Further, in Example 4 to Example 6, as further proof supporting the involvement of chymase in dermatitis exhibiting biphasic skin reaction, the fact that dermatitis exhibiting biphasic skin reaction is induced by intradermal inoculation of human chymase into the ear of mice is presented. In Example 7 and Example 8, the results of analysis of the mechanism of action of chymase in such biphasic skin reaction are shown.

On the other hand, in Example 9 to Example 12, the usefulness of a chymase inhibitor is demonstrated by using dermatitis induced by repeated application of hapten as a model for dermatitis induced by repeated exposure to an antigen and analyzing the model and showing the effect of a chymase inhibitor in this model. Further, since it is conceivable that mast cells undergo repeated degranulation reactions due to repeated exposure to allergens in patients suffering from atopic dermatitis etc., in Example 13 to Example 15, dermatitis induced by repeated inoculation of human chymase into the ears was analyzed for the purpose of studying the effects of a repeated degranulation reaction on the skin. Further, in Examples 16 to 17, the effects of chymase on the expression of SCF, the major cytokine for mast cells, are shown as one of the mechanisms of chymase-induced dermatitis. Further, in Example 18, the effects of chymase inhibitor on dermatitis was examined using NC/Nga mice as the second model induced by repeated exposure to antigen.

Preparation Example 1

Synthesis of 7-chloro-3-(3-hydroxybenzenesulfonyl)-2,4 (1H,3H)-quinazolinedione (Compound 1)

Following the Synthesis Method (B), 938 mg (5.42 mmol) of 3-hydroxybenzenesulfonamide was dissolved in 40 ml of tetrahydrofuran, then 892 μl (5.96 mmol) of 1,8-diazabicyclo [5,4,0]-7-undecene (hereinafter referred to as DBU) was added dropwise. The reaction solution was stirred at room temperature for 15 minutes, then 1.66 g (5.42 mmol) of methyl 4-chloro-2-N-phenoxycarbonylanthranilate was added and the mixture was stirred at room temperature overnight. An excess amount of water was poured into the reaction solution, then the mixture was made acidic with hydrochloric acid and extracted with ethyl acetate. The organic layer was washed with water and saturated saline, dried over anhydrous magnesium sulfate, and concentrated. The crude product thus obtained was purified by silica gel column chromatography (0% to 5% methanol/dichloromethane) to obtain 1.23 g (yield 59%) of methyl 4-chloro-2-{[(3-hydroxybenzenesulfonylamino)carbonyl]amino} benzoate. Properties: colorless amorphous, PMR (δ ppm, DMSO-$d_6$): 3.91 (3H, s), 7.02 (1H, m), 7.09 (1H, m), 7.34 (1H, t), 7.57 (2H, m), 7.89 (1H, d), 8.38 (1H, d), 10.94 (1H, s). Next, the 1.23 g (3.2 mmol) of the compound thus obtained was dissolved in 20 ml of methanol, then 10 ml of 2N sodium hydroxide aqueous solution was added dropwise. The reaction solution was stirred at room temperature for 15 minutes, then an excess amount of water was added and the mixture was made acidic with hydrochloric acid. This was then stirred to cause crystals to precipitate which were then obtained by filtration and dried to obtain carboxylic acid. The product thus obtained was dissolved in 50 ml of tetrahydrofuran (hereinafter referred to as THF), then 434 mg (2.68 mmol) of CDI was added under ice cooling and the mixture was stirred for 30 minutes. The reaction solution was diluted with ethyl acetate, washed with water and saturated saline, and dried over anhydrous magnesium sulfate, then concentrated to obtain a crude product. The crude product was purified by silica gel column chromatography (ethyl acetate:n-hexane=1:2) to obtain 230 mg (yield 20%: 2 steps) of the above-identified compound. Properties: colorless crystal, Melting point: >200° C. (decomposition), PMR (δ ppm, DMSO-$d_6$): 7.12 (2H, s), 7.24 (1H, d), 7.48 (1H, t), 7.58 (2H, s), 7.85 (1H, d), 10.28 (1H, s), 11.63 (1H, s).

Preparation Example 2

Synthesis of 3-(2-aminobenzenesulfonyl)-7-chloro-2,4(1H,3H)-quinazolinedione (Compound 2)

2.7 g (15.7 mmol) of 2-aminobenzenesulfonamide and 4.8 g (15.7 mmol) of methyl 4-chloro-2-N-phenoxycarbonylanthranilate were treated in the same way as Preparation Example 1 to obtain 3.2 g (yield 58%: 3 steps) of the above-identified compound. Properties: colorless crystal, Melting point: >200° C. (decomposition), PMR (δ ppm, DMSO-$d_6$): 6.46 (2H, s), 6.65 (1H, t), 6.81 (1H, d), 7.12 (1H, s), 7.23 (1H, d), 7.34 (1H, t), 7.76 (1H, d), 7.86 (1H, d).

Preparation Example 3

Synthesis of 7-chloro-3-(2-methylsulfonylaminobenzenesulfonyl)-2,4(1H 3H)-quinazolinedione (Compound 3)

22 mg (0.06 mmol) of Compound 2 was dissolved in 200 μl of pyridine, 11.6 μl (0.15 mmol) of methanesulfonyl chloride was added dropwise, then the resultant mixture was stirred at room temperature overnight. An excess amount of water was added to the reaction solution and the mixture was extracted with ethyl acetate. The organic layer was washed with 1N aqueous hydrochloric acid solution and saturated saline, then dried over anhydrous magnesium sulfate and concentrated to obtain a crude product. The crude product was crystallized from diethyl ether to obtain 16 mg (0.04 mmol) of the above-identified compound. Properties: colorless crystal, Melting point: >2000C (decomposition), PMR (δ ppm, DMSO-$d_6$): 3.61 (3H, s), 7.10 (1H, d), 7.20 (1H, d), 7.74 (1H, d), 7.82-7.90 (4H, m), 8.34 (1H, d), 11.70 (1H, s).

Preparation Example 4

Synthesis of 3-(4-aminobenzenesulfonyl)-7-chloro-2,4 (1H,3H)-quinazolinedione (Compound 4)

2.7 g (15.7 mmol) of 4-aminobenzenesulfonamide and 4.8 g (15.7 mmol) of methyl 4-chloro-2-N-phenoxycarbonylanthranilate were treated in the same way as Preparation Example 1 to obtain 7.9 g (yield 94%) of methyl 2-{[(4-aminobenzenesulfonylamino)carbonyl]amino}-4-chlorobenzoate. Properties: colorless amorphous, PMR (δ ppm, DMSO-$d_6$): 3.59 (3H, s), 5.37 (2H, s), 6.45 (2H, d), 6.83 (1H, dd), 7.41 (2H, d), 7.81 (1H, d), 8.66 (1H, d), 9.64 (1H, s).

Then, from the resultant 7.9 g (14.8 mmol) of sulfonylurea product, in the same way, 4.3 g (yield 83%: 2 steps) of the above-identified compound was obtained. Properties: colorless crystal, Melting point: >200° C. (decomposition), PMR (δ ppm, DMSO-d₆): 6.39 (2H, s), 6.63 (2H, d), 7.09 (1H, s), 7.22 (1H, d), 7.76 (2H, d), 7.83 (1H, d), 11.51 (1H, S).

Preparation Example 5

Synthesis of 3-(3-carboxymethyl-benzenesulfonyl)-7-chloro-2,4 (1H.3H)-quinazolinedione (Compound 5)

Following the Synthesis Method (A), 3.27 g (11.6 mmol) of 3-allyloxycarbonylmethylbenzenesulfonyl isocyanate was dissolved in 100 ml of anhydrous THF, then 1.98 g (11.5 mmol) of 4-chloroanthranilic acid was added and the mixture was stirred at room temperature for 2 hours. The reaction solution was cooled with ice water, then 1.87 g (11.5 mmol) of CDI was added and the resultant mixture was stirred under ice cooling for 30 minutes. An excess amount of water was poured into the reaction solution, then the mixture was extracted with ethyl acetate. The organic layer was washed, dried, and concentrated to obtain a crude product. This was crystallized with a small amount of ethyl acetate to obtain 2.0 g (yield 40%) of 3-(3-allyloxy-carbonylmethylbenzenesulfonyl)-7-chloro-2,4 (1H,3H)-quinazolinedione. The allyl product thus obtained was dissolved in 100 ml of a formic acid-THF (1:9) mixture and 700 mg of triphenylphosphine was added. The reactor was shaded from light and under nitrogen atmosphere, then 700 mg of tetrakis(triphenylphosphine)palladium (0) was added and the resultant mixture was stirred while shaded at room temperature overnight. The reaction solution was concentrated in vacuo and the solid obtained was washed with methylene chloride to obtain 1.47 g (yield 81%) of the above-identified compound. Properties: colorless crystal, Melting point: >200° C. (decomposition), PMR (δ ppm, DMSO-d₆): 3.76 (2H, s), 7.13 (1H, s), 7.24 (1H, d), 7.61-7.69 (2H, m), 7.86 (1H, d), 8.05 (2H, s), 12.50 (1H, br).

Preparation Example 6

Synthesis of 3-4-carboxymethyl-benzenesulfonyl)-7-chloro-2,4 (1H,3H)-quinazolinedione (Compound 6)

1.10 g (3.95 mmol) of 4-allyloxycarbonylmethyl-benzenesulfonyl isocyanate and 678 mg (3.95 mmol) of 4-chloroanthranilic acid were treated in the same way as in Preparation Example 5 to obtain 657 mg (yield 38%) of 3-(4-allyloxycarbonylbenzenesulfonyl)-7-chloro-2,4 (1H,3H)-quinazolinedione. 538 mg (1.24 mmol) thereof was treated in the same way to obtain 342 mg of the above-identified compound (yield 70%). Properties: colorless crystal, Melting point: >200° C. (decomposition), PMR (δ ppm, DMSO-d₆): 3.75 (2H, s), 7.13 (1H, s), 7.23 (1H, d), 7.61-7.69 (2H, m), 7.86 (1H, d), 8.05 (2H, s), 12.07 (2H, br).

Preparation Example 7

Synthesis of (±)-2-{4-[(7-chloro-2,4 (1H,3H)-quinazolin-3-yl)sulfonyl]phenyl}butyric Acid (Compound 7)

1.02 g (3.41 mmol) of t-butyl (±)-2-(4-amino-sulfonylphenyl)butyrate acid and 1.04 g (3.41 mmol) of methyl 4-chloro-2-N-phenoxycarbonylanthranilate were treated in the same way as Preparation Example 1 to obtain 1.46 g (yield 84%) of methyl 2-[({4-[1-(t-butoxycarbonyl)propyl]benzenesulfonylamino}carbonyl)amino]-4-chlorobenzoate. Properties: colorless amorphous, PMR (δ ppm, CDCl₃): 0.89 (3H, t), 1.38 (9H, s), 1.69-1.76 (1H, m), 2.03-2.10 (1H, m), 3.42 (1H, t), 3.94 (3H, s), 7.04 (1H, d), 7.47 (2H, d), 7.93 (1H, d), 8.01 (2H, d), 8.45 (1H, br), 11.04 (1H, br).

Next, 4.3 ml (8.6 mmol) of 2N sodium hydroxide aqueous solution was used to similarly form carboxylic acid in an amount of 1.43 g and 463 mg (2.86 mmol) of CDI was used to obtain 970 mg (yield 71%: 2 steps) of t-butyl (±)-2-{4-[(7-chloro-2,4 (1H,3H)-quinazolin-3-yl)sulfonyl]phenyl}butyrate.

Further, the t-butylester thus obtained was dissolved in 5 ml of dichloromethane, then 5 ml of trifluoroacetic acid was added and the resultant mixture was stirred at room temperature for 40 minutes. The reaction solution was concentrated in vacuo and the resultant crude product was washed with a small amount of diethyl ether to obtain 820 mg of the above-identified compound (yield 96%). Properties: colorless crystal, Melting point: >200° C. (decomposition), PMR (δ ppm, DMSO-d₆): 0.84 (3H, t), 1.67-1.75 (1H, m), 1.98-2.05 (1H, m), 3.62 (1H, t), 7.11 (1H, s), 7.24 (1H, d), 7.61 (2H, d), 7.86 (1H, d), 8.13 (2H, d), 11.62 (1H, s).

Preparation Example 8

Synthesis of 3-(3-amino-4-chlorobenzenesulfonyl)-7-chloro-2,4 (1H,3H)-quinazolinedione (Compound 8)

1.0 g (2.93 mmol) of 3-benzyloxycarbonylamino-4-chlorobenzenesulfonamide and 1.18 g (2.93 mmol) of benzyl 4-chloro-2-N-phenoxycarbonylanthranilate were treated in the same way as Preparation Example 1 to obtain 1.43 g (yield 78%) of benzyl 2-{[(3-benzyloxycarbonylamino-4-chlorobenzene sulfonylamino)carbonyl]amino}-4-chlorobenzoate. Properties: colorless amorphous, PMR (δ ppm, DMSO-d₆): 5.19 (2H, s), 5.36 (2H, s), 7.21 (1H, dd), 7.34-7.48 (10H, m), 7.72-7.76 (2H, m), 7.97 (1H, d), 8.25 (1H, d), 8.30 (1H, d), 9.53 (1H, s), 10.30 (1H, s). 1.38 g (2.20 mmol) thereof was dissolved in 50 ml of THF, then 200 mg of palladium-carbon (10%) was added and the mixture was stirred under a hydrogen flow for 2 hours. The reaction mixture was filtered with Celite to remove the palladium-carbon, then the filtrate was concentrated in vacuo to obtain a carboxylic acid. The product obtained was suspended in 50 ml of THF, then 356 mg (2.20 mmol) of CDI was added under ice cooling and the resultant mixture was treated in the same way as Preparation Example 1 to obtain 560 mg (yield 66%: 2 steps) of the above-identified compound. Properties: colorless crystal, Melting point: >200° C. (decomposition), PMR (δ ppm, DMSO-d₆): 6.00 (2H, s), 7.12 (1H, s), 7.26 (2H, t), 7.48 (1H, d), 7.66 (1H, s), 7.86 (1H, d), 11.76 (1H, br).

Preparation Example 9

Synthesis of 3-(4-amino-3,5-dichlorobenzenesulfonyl)-7-chloro-2,4 (1H,3H)-quinazolinedione (Compound 9)

1.06 g (4.40 mmol) of 4-amino-3,5-dichloro-benzenesulfonamide and 1.34 g (4.40 mmol) of methyl 4-chloro-2-N-phenoxycarbonylanthranilate were treated in the same way as Preparation Example 1 to obtain 905 mg (yield 44%) of methyl 2-{[(4-amino-3,5-dichlorobenzenesulfonylamino)carbonyl]amino}-4-chlorobenzoate. Properties: colorless amorphous, PMR (δ ppm, DMSO-d₆): 3.87 (3H, s), 6.59 (2H, br), 7.22 (1H, dd), 7.72 (2H, s), 7.93 (1H, d), 8.24 (1H, d), 10.17 (1H, s).

Then, from 905 mg (2.0 mmol) of the resultant sulfonylurea product, in the same way, 660 mg (yield 82%: 2 steps) of the above-identified compound was obtained. Properties: colorless crystal, Melting point: >200° C. (decomposition), PMR (δ ppm, DMSO-$d_6$): 6.80 (2H, s), 7.12 (1H, s), 7.24 (1H, d), 7.86 (1H, d), 7.92 (2H, s), 11.63 (1H, br).

Preparation Example 10

Synthesis of 3-(3-amino-4-methylbenzenesulfonyl)-7-chloro-2,4(1H,3H)-quinazolinedione (Compound 10)

960 mg (3.00 mmol) of 3-benzyloxycarbonylamino-4-methylbenzenesulfonamide and 1.14 g (3.00 mmol) of benzyl 4-chloro-2-N-phenoxycarbonylanthranilate were treated in the same way as in Preparation Example 8 to obtain 1.14 g (yield 62% of benzyl 2-{[(3-benzyloxycarbonylamino-4-methylbenzenesulfonylamino)carbonyl]amino}-4-chlorobenzoate. Properties: colorless amorphous, PMR (δ ppm, DMSO-$d_6$): 2.30 (3H, s), 5.17 (2H, s), 5.36 (2H, s), 7.20 (1H, dd), 7.33-7.48 (1H, m), 7.63 (1H, d), 7.97 (1H, d), 8.11 (1H, s), 8.25 (1H, s), 9.27 (1H, s), 10.30 (1H, s), 12.20 (1H, br).

Then, from 1.14 g (1.87 mmol) of the resultant sulfonylurea product, in the same way, 190 mg (yield 27%: 2 steps) of the above-identified compound was obtained. Properties: colorless crystal, Melting point: >200° C. (decomposition), PMR (δ ppm, DMSO-$d_6$): 2.12 (3H, s), 5.47 (2H, s), 7.12 (1H, s), 7.16-7.25 (3H, m), 7.38 (1H, s), 7.85 (1H, d), 11.58 (1H, s).

Preparation Example 11

Synthesis of 3-[(3-carboxymethylaminophenyl)sulfonyl]-7-chloro-2,4 (1H,3H)-quinazolinedione (Compound 11)

1.62 g (5.65 mmol) of 3-t-butoxycarbonyl-methylaminobenzenesulfonamide and 1.73 g (5.65 mmol) of methyl 4-chloro-2-N-phenoxycarbonylanthranilate were treated in the same way as in Preparation Example 7 to obtain 209 mg (yield 9%: 4 steps) of the above-identified compound. Properties: colorless crystal, Melting point: >200° C. (decomposition), PMR (δ ppm, DMSO-$d_6$): 3.86 (2H, s), 6.88 (1H, s), 7.12 (1H, s), 7.24 (1H, d), 7.30-7.38 (3H, m), 7.86 (1H, d), 11.61 (1H, br).

Preparation Example 12

Synthesis of 3-(3-aminobenzenesulfonyl)-7-chloro-2,4 (1H,3H)-quinazolinedione (Compound 12)

3.5 g (12.9 mmol) of 3-t-butoxycarbonylamino-benzenesulfonamide and 3.9 g (12.8 mmol) of methyl 4-chloro-2-N-phenoxycarbonylanthranilate were treated in the same way as in Preparation Example 7 to obtain 2.2 g (yield 49%: 4 steps) of the above-identified compound. Properties: colorless crystal, Melting point: >200° C. (decomposition), PMR (δ ppm, DMSO-$d_6$): 5.72 (2H, s), 6.87 (1H, d), 7.12 (1H, s), 7.23-7.27 (2H, m), 7.33 (1H, S), 7.86 (1H, d), 11.61 (1H, s).

Preparation Example 13

Synthesis of 2-{3-[(7-chloro-2,4(1H, 3H) -quinazolinedion-3-yl)sulfonyl] phenylaminocarbonyl}propionic Acid (Compound 13)

100 mg (0.28 mmol) of Compound 12 was dissolved in 5 ml of THF, 100 mg (1.0 mmol) of succinic anhydride was added, and the resultant mixture was heated and refluxed for 3 hours. The reaction solution was concentrated in vacuo and the crude product thus obtained was crystallized with ethyl acetate-diethyl ether to obtain 120 mg (yield 96%) of the above-identified compound. Properties: colorless crystal, Melting point: 187-188° C., PMR (δ ppm, DMSO-$d_6$): 2.54 (2H, d), 2.59 (2H, d), 7.12 (1H, s), 7.24 (1H, d), 7.59 (1H, t), 7.80 (1H, d), 7.86 (1H, d), 7.96 (1H, d), 8.41 (1H, s), 10.40 (1H, s), 11.63 μL (1H, br), 12.10 (1H, br).

Preparation Example 14

Synthesis of 3-{3-[(7-chloro-2,4 (1H,3H)-auinazolinedion-3-yl)sulfonyl]phenyl}acrylic Acid (Compound 14)

1.54 g (5.44 mmol) of t-butyl 3-(3-aminosulfonyl)phenylacrylate and 1.66 g (5.44 mmol) of methyl 4-chloro-2-N-phenoxycarbonylanthranilate were treated in the same way as in Preparation Example 7 to obtain 2.18 g (yield 81%) of methyl 2-({[3-(3-t-butoxy-3-oxo-1-propenyl)benzenesulfonylamino]carbonyl}amino)-4-chlorobenzoate. Properties: colorless amorphous, PMR (δ ppm, CDCl$_3$): 1.53 (9H, s), 3.95 (3H, s), 6.46 (1H, d), 7.05 (1H, d), 7.55 (1H, m), 7.57 (1H, d), 7.72 (1H, m), 7.93 (1H, m), 8.04 (1H, m), 8.27 (1H, s), 8.46 (1H, d), 11.05 (1H, br).

Then, from 2.18 g (4.4 mmol) of the resultant sulfonylurea product, in the same way, 698 mg (yield 37%: 3 steps) of the above-identified compound was obtained. Properties: colorless crystal, Melting point: >200° C. (decomposition), PMR (δ ppm, DMSO-$d_6$): 6.65 (1H, d), 7.12 (1H, s), 7.25 (1H, d), 7.69 (1H, d), 7.72 (1H, t), 7.87 (1H, d), 8.12 (2H, q), 8.37 (1H, s), 11.64 (1H, s).

Preparation Example 15

Synthesis of 4-[(7-chloro-2,4 (1H,3H)-quinazolinedion-3-yl)sulfonyl]salicylic Acid (Compound 15)

1.0 g (3.66 mmol) of 4-t-butoxycarbonyl-3-hydroxybenzenesulfonamide and 1.12 g (3.66 mmol) of methyl 4-chloro-2-N-phenoxycarbonylanthranilate were treated in the same way as in Preparation Example 7 to obtain 1.79 g (yield 100%) of methyl 2-{[(4-t-butoxycarbonyl-3-hydroxybenzenesulfonylamino)carbonyl]amino}-4-chlorobenzoate. Properties: colorless amorphous, PMR (δ ppm, DMSO-$d_6$): 1.57 (9H, s), 3.87 (3H, s), 7.14 (1H, d), 7.40-7.45 (2H, m), 7.85 (1H, d), 7.92 (1H, d), 8.32 (1H, d), 10.13 (1H, s), 10.82 (1H, s).

Then, from 1.78 g (3.66 mmol) of the resultant sulfonylurea product, in the same way, 370 mg (yield 25%: 3 steps) of the above-identified compound was obtained. Properties: colorless crystal, Melting point: >200° C. (decomposition), PMR (δ ppm, DMSO-$d_6$): 7.13 (1H, s), 7.26 (1H, d), 7.69 (1H, d), 7.87 (1H, d), 8.01 (1H, d), 11.67 (1H, S).

Preparation Example 16

Synthesis of 4-[(7-chloro-2,4 (1H,3H)-quinazolinedion-3-yl)sulfonyl]salicylic Acid Monosodium Salt (Compound 16)

50 mg (0.13 mmol) of Compound 15 was suspended in approximately 1 ml of THF, then 126 μl of 1N sodium hydroxide aqueous solution was added dropwise. The solution was confirmed to have become uniform, then 30 ml of water was added and the mixture freeze-dried to quantitatively obtain the above-identified compound in an amorphous state in an amount of 52 mg. Properties: colorless amorphous, PMR (δ ppm, CD$_3$OD): 7.11 (1H, s), 7.19 (1H, d), 7.58 (1H, d), 7.63 (1H, s), 7.92 (1H, d), 8.03 (1H, d).

Preparation Example 17

Synthesis of 4-[(7-chloro-2,4 (1H,3H)-quinazolinedion-3-yl)sulfonyl]anthranilic Acid (Compound 17)

2.84 g (6.99 mmol) of 3-benzyloxycarbonylamino-4-t-butoxycarbonylbenzenesulfonamide and 2.67 g (6.99 mmol) of benzyl 4-chloro-2-N-phenoxycarbonylanthranilate were treated in the same way as in Preparation Example 8 to obtain 3.74 g (yield 77%) of benzyl 2-{[(3-benzyloxycarbonylamino-4-t-butoxycarbonylbenzenesulfonylamino)carbonyl]amino}-4-chlorobenzoate. Properties: colorless amorphous, PMR (δ ppm, DMSO-d$_6$): 1.54 (9H, s), 5.19 (2H, s), 5.34 (2H, s), 7.05 (1H, m), 7.34-7.58 (10H, m), 7.60 (1H, d), 7.90 (1H, d), 7.98 (1H, d), 8.50 (1H, br), 8.62 (1H, s), 10.00 (1H, br), 10.41 (1H, s).

Then, from 3.74 g (5.39 mmol) of the resultant sulfonylurea, in the same way, 690 mg (yield 30%: 2 steps) of t-butyl 4-[(7-chloro-2,4 (1H,3H)-quinazolinedion-3-yl)sulfonyl]anthranilate was obtained, then this was subjected to a similar debutylation reaction to obtain 503 mg (yield 84%) of the above-identified compound. Properties: colorless crystal, Melting point: >200° C. (decomposition), PMR (δ ppm, DMSO-d$_6$): 7.14 (1H, s), 7.18 (1H, d), 7.25 (1H, d), 7.59 (1H, s), 7.87 (1H, d), 7.89 (1H, d), 11.62 (1H, S).

Preparation Example 18

Synthesis of 4-[(7-chloro-2,4 (1H,3H)-quinazolinedion-3-yl)sulfonyl]anthranilic Acid Monosodium Salt (Compound 18)

50 mg (0.13 mmol) of Compound 17 was suspended in approximately 1 ml of THF, then 126 μl of 1N sodium hydroxide aqueous solution was added dropwise. The solution was confirmed to have become uniform, then 30 ml of water was added and the mixture was freeze-dried to quantitatively obtain the above-identified compound in an amorphous state in an amount of 52 mg. Properties: colorless amorphous, PMR (δ ppm, DMSO-d$_6$): 7.11-7.22 (3H, m), 7.37 (1H, s), 7.83 (1H, d), 7.91 (1H, d).

Preparation Example 19

Synthesis of 3-(4-hydroxybenzenesulfonyl)-7-chloro-2,4 (1H,3H)-quinazolinedione (Compound 19)

1.50 g (7.03 mmol) of 4-allyloxybenzenesulfonyl isocyanate and 1.2 g (7.03 mmol) of 4-chloroanthranilic acid were treated in the same way as in Preparation Example 5 to obtain 1.5 g (yield 53%) of 3-(4-allyloxybenzenesulfonyl)-7-chloro-2,4 (1H,3H)-quinazolinedione. 500 mg (1.27 mmol) thereof was similarly treated to obtain 405 mg of the above-identified compound (yield 90%). Properties: colorless crystal, Melting point: >200° C. (decomposition), PMR (δ ppm, DMSO-d$_6$): 6.98 (2H, d), 7.11 (1H, s), 7.23 (1H, d), 7.85 (1H, d), 8.00 (2H, d), 11.25 (1H, br).

Preparation Example 20

Synthesis of 4-[(2,4 (1H,3H)-quinazolinedion-3-yl)sulfonyl]salicylic Acid (Compound 20)

618 mg (2.26 mmol) of 4-t-butoxycarbonyl-3-hydroxybenzenesulfonamide and 613 mg (2.26 mmol) of methyl 2-N-phenoxycarbonylanthranilate were treated in the same way as in Preparation Example 17 to obtain 792 mg (yield 78%) of methyl 2-{[(4-t-butoxycarbonyl-3-hydroxybenzene-sulfonylamino)carbonyl]amino}benzoate. Properties: colorless amorphous, PMR (δ ppm, CDCl$_3$): 1.60 (9H, s), 3.97 (3H, s), 7.09 (1H, t), 7.49-7.52 (2H, m), 7.65 (1H, d), 7.90 (1H, d), 8.01 (1H, dd), 8.33 (1H, d), 10.98 (1H, s), 11.18 (1H, s).

Then, from 790 mg (1.75 mmol) of the resultant sulfonylurea product, in the same way, 100 mg (yield 8%: 3 steps) of the above-identified compound was obtained. Properties: colorless crystal, Melting point: >200° C. (decomposition), PMR (δ ppm, DMSO-d$_6$): 7.13 (1H, d), 7.22 (1H, t), 7.63-7.69 (3H, m), 7.87 (1H, d), 8.01 (1H, d), 11.57 (1H, s).

Preparation Example 21

Synthesis of 5-[(7-chloro-2,4 (1H,3H)-quinazolinedion-3-yl)sulfonyl]salicylic Acid (Compound 21)

320 mg (1.17 mmol) of 3-t-butoxycarbonyl-4-hydroxybenzenesulfonamide and 447 mg (1.17 mmol) of benzyl 4-chloro-2-N-phenoxycarbonylanthranilate were treated in the same way as in Preparation Example 17 to obtain 611 mg (yield 93%) of benzyl 2-{[(3-t-butoxycarbonyl-4-hydroxybenzenesulfonylamino)carbonyl]amino}-4-chlorobenzoate. Properties: colorless amorphous, PMR (δ ppm, CDCl$_3$): 1.62 (9H, s), 5.35 (2H, s), 7.01-7.05 (2H, m), 7.37-7.41 (5H, m), 7.96 (1H, d), 8.10 (1H, dd), 8.46-8.48 (2H, m), 10.99 (1H, s), 11.66 (1H, s).

Then, from 611 mg (1.09 mmol) of the resultant sulfonylurea product, in the same way, 114 mg (yield 33%: 3 steps) of the above-identified compound was obtained. Properties: colorless crystal, Melting point: >200° C. (decomposition), PMR (δ ppm, DMSO-d$_6$): 7.11 (1H, s), 7.19 (1H, d), 7.24 (1H, d), 7.86 (1H, d), 8.20 (1H, d), 8.56 (1H, s), 11.57 (1H, s).

Preparation Example 22

Synthesis of 3-(3-acetamide-4-methoxybenzenesulfonyl)-7-chloro-2,4 (1H,3H)-quinazolinedione (Compound 22)

500 mg (2.19 mmol) of 3-acetamide-4-methoxybenzenesulfonamide and 836 mg (2.19 mmol) of benzyl 4-chloro-2-N-phenoxycarbonylanthranilate were treated in the same way as in Preparation Example 8 to obtain 812 mg (yield 70%) of benzyl 2-{[(3-acetylamino-4-methoxybenzenesulfonylamino)carbonyl]amino}-4-chlorobenzoate. Properties: colorless amorphous, PmR (δ ppm, DMSO-d$_6$): 2.12 (3H, s), 3.93 (3H, s), 5.36 (2H, s), 7.20 (1H, d), 7.24 (1H, d), 7.36-7.48 (5H, m), 7.69 (1H, d), 7.96 (1H, d), 8.24 (1H, s), 8.67 (1H, s), 9.39 (1H, s), 10.25 (1H, s), 12.11 (1H, br).

Then, from 611 mg (1.09 mmol) of the resultant sulfonylurea product, in the same way, 250 mg (yield 39%: 2 steps) of the above-identified compound was obtained. Properties: colorless crystal, Melting point: >200° C. (decomposition), PMR (δ ppm, DMSO-d$_6$): 2.12 (3H, s), 3.95 (3H, s), 7.12 (1H, s), 7.23 (1H, d), 7.30 (1H, d), 7.85 (1H, d), 7.89 (1H, d), 8.80 (1H, s), 9.42 (1H, s), 11.59 (1H, br).

Preparation Example 23

Synthesis of 3-(3-amino-4-methoxybenzenesulfonyl)-7-chloro-2,4 (1H,3H)-quinazolinedione (Compound 23)

400 mg (1.40 mmol) of 3-t-butoxycarbonylamino-4-methoxybenzenesulfonamide and 533 mg (1.40 mmol) of benzyl 4-chloro-2-N-phenoxycarbonylanthranilate were treated in the same way as in Preparation Example 17 to obtain 86 mg (yield 16%: 4 steps) of the above-identified compound. Properties: colorless crystal, Melting point: >200° C. (decomposition), PMR (δ ppm, DMSO-d$_6$): 3.81 (3H, s), 7.26-7.37 (5H, m), 7.77 (1H, s), 7.90 (1H, d), 7.94 (1H, d), 11.73 (1H, s).

Preparation Example 24

Synthesis of 7-chloro-3-(4-methoxy-3-methylsulfonylaminobenzenesulfonyl)-2,4 (1H,3H)-quinazolinedione (Compound 24)

500 mg (1.89 mmol) of 4-methoxy-3-methylsulfonylaminobenzenesulfonamide and 722 mg (1.89 mmol) of benzyl 4-chloro-2-N-phenoxycarbonylanthranilate were treated in the same way as in Preparation Example 8 to obtain 888 mg (yield 83%) of benzyl 2-({[(4-methoxy-3-methylsulfonylamino)benzene sulfonylamino]carbonyl}amino)-4-chlorobenzoate. Properties: colorless amorphous, PMR (δ ppm, DMSO-d$_6$): 2.12 (3H, s), 3.93 (3H, s), 5.36 (2H, s), 7.20 (1H, d), 7.24 (1H, d), 7.36-7.48 (5H, m), 7.69 (1H, d), 7.96 (1H, d), 8.24 (1H, s), 8.67 (1H, s), 9.39 (1H, s), 10.25 (1H, s), 12.11 (1H, br).

Then, from 880 mg (1.55 mmol) of the resultant sulfonylurea product, in the same way, 620 mg (yield 85%: 2 steps) of the above-identified compound was obtained. Properties: colorless crystal, Melting point: >200° C. (decomposition), PMR (δ ppm, DMSO-d$_6$): 3.04 (3H, s), 3.94 (3H, s), 7.11 (1H, s), 7.23 (1H, d), 7.34 (1H, d), 7.86 (1H, d), 7.99 (1H, d), 8.10 (1H, s).

Preparation Example 25

Synthesis of 4-[(7-chloro-2,4 (1H,3H)-quinazolinedion-3-yl)sulfonyl]-1-hydroxy-nanhthalene-2-carboxylic acid (Compound 25)

323 mg (1.00 mmol) of 3-t-butoxycarbonyl-4-hydroxy-1-naphthalenesulfonamide and 381 mg (1.00 mmol) of benzyl 4-chloro-2-N-phenoxycarbonylanthranilate were treated in the same way as in Preparation Example 17 to obtain 447 mg (yield 73%) of 4-({[(2-benzyloxycarbonyl-5-chloroanilino)carbonyl]amino}sulfonyl)-1-hydroxy-2-naphthalenecarboxylic acid t-butyl ester. Properties: colorless amorphous, PMR (δ ppm, DMSO-d$_6$): 1.66 (9H, s), 5.34 (3H, s), 6.98 (1H, d), 7.35-7.48 (5H, m), 7.66 (1H, m), 7.81 (1H, m), 7.89 (1H, d), 8.37 (2H, m), 8.44 (1H, s), 8.71 (1H, d), 10.02 (1H, br), 12.52 (1H, br).

Then, from 445 mg (0.72 mmol) of the resultant sulfonylurea product, in the same way, 56 mg (yield 18%: 3 steps) of the above-identified compound was obtained. Properties: colorless crystal, Melting point: >200° C. (decomposition), PMR (δ ppm, DMSO-d$_6$): 7.08 (1H, s), 7.20 (1H, d), 7.63 (1H, t), 7.77 (1H, t), 7.84 (1H, d), 8.42 (1H, d), 8.51 (1H, d), 8.75 (1H, s), 11.57 (1H, s).

Preparation Example 26

Synthesis of 5-[(7-chloro-2,4(1H,3H)-quinazolinedion-3-yl)sulfonyl]anthranilic Acid (Compound 26)

834 mg (2.05 mmol) of 4-benzyloxycarbonylamino-3-t-butoxycarbonylbenzenesulfonamide and 783 mg (2.05 mmol) of benzyl 4-chloro-2-N-phenoxycarbonylanthranilate were treated in the same way as in Preparation Example 17 to obtain 1.18 g (yield 83%) of benzyl 2-{[(4-benzyloxycarbonylamino-3-t-butoxycarbonylbenzenesulfonylamino)carbonyl]amino}-4-chlorobenzoate. Properties: colorless amorphous, PMR (δ ppm, CDCl$_3$): 1.56 (9H, s), 5.22 (2H, s), 5.37 (2H, s), 7.04 (1H, dd), 7.33-7.42 (10H, m), 7.97 (1H, d), 8.14 (1H, d), 8.45 (1H, d), 8.60 (1H, d), 8.65 (1H, d), 11.01 (1H, s), 11.11 (1H, s).

Then, from 1.17 g (1.69 mmol) of the resultant sulfonylurea product, in the same way, 404 mg (yield 60%: 3 steps) of the above-identified compound was obtained. Properties: colorless crystal, Melting point: >200° C. (decomposition), PMR (δ ppm, DMSO-d$_6$): 6.89 (1H, d), 7.11 (1H, s), 7.23 (1H, d), 7.85 (1H, d), 7.98 (1H, d), 8.51 (1H, s), 11.51 (1H, s).

Preparation Example 27

Synthesis of 4-[(7-methoxy-2,4 (1H,3H)-quinazolinedion-3-yl)sulfonyl]anthranilic Acid (Compound 27)

500 mg (1.23 mmol) of 3-benzyloxycarbonylamino-4-t-butoxycarbonylbenzenesulfonamide and 460 mg (1.22 mmol) of benzyl 4-methoxy-2-N-phenoxycarbonylanthranilate were treated in the same way as in Preparation Example 17 to obtain 15 mg (yield 3.1%: 4 steps) of the above-identified compound. Properties: colorless crystal, Melting point: >200° C. (decomposition), PMR (δ ppm, DMSO-d$_6$): 3.82 (3H, s), 6.58 (1H, s), 6.80 (1H, d), 7.16 (1H, d), 7.56 (1H, s), 7.80 (1H, d), 7.90 (1H, d), 11.49 (1H, s).

Preparation Example 28

Synthesis of (±)-7-[(7-chloro-2,4(1H,3H)-quinazolinedion-3-yl)sulfonyl]-2-oxo-1H,3H-quinoline-3-carboxylic acid (Compound 28)

400 mg (1.23 mmol) of (±)-3-t-butoxycarbonyl-2-oxo-1H,3H-quinoline-7-sulfonamide and 468 mg (1.23 mmol) of benzyl 4-chloro-2-N-phenoxycarbonylanthranilate were treated in the same way as in Preparation Example 17 to obtain 649 mg (yield 86%) of 8-({[(2-benzyloxycarbonyl-5-chloroanilino)carbonyl]amino}sulfonyl)-2-oxo-1,2,3,4 tetrahydro-3-quinoline carboxylic acid t-butyl ester. Properties: colorless amorphous, PMR (δ ppm, CDCl$_3$): 1.32 (9H, s), 3.18-3.30 (2H, m), 3.54 (1H, m), 5.35 (2H, s), 6.85 (1H, m), 7.00 (1H, m), 7.35-7.39 (5H, m), 7.87-7.96 (3H, m), 8.47 (1H, m), 8.78 (1H, br), 10.92 (1H, br).

Then, from 640 mg (1.04 mmol) of the resultant sulfonylurea product, in the same way, 258 mg (yield 55%: 3 steps) of the above-identified compound was obtained. Properties: colorless crystal, Melting point: >200° C. (decomposition), PMR (δ ppm, DMSO-d$_6$): 3.23-3.31 (2H, m), 3.59 (1H, t), 7.07 (1H, d), 7.12 (1H, S), 7.25 (1H, d), 7.86 (1H, d), 7.96 (1H, d), 7.98 (1H, d), 10.84 (1H, s), 11.60 (1H, s).

Preparation Example 29

Synthesis of (±)-6-[(7-chloro-2,4 (1H,3H)-quinazolinedion-3-yl)sulfonyl]-3-oxo-1,4-benzoxazine-2-carboxylic Acid (Compound 29)

300 mg (0.91 mmol) of (±)-2-t-butoxycarbonyl-3-oxo-1,4-benzoxazin-6-sulfonamide and 349 mg (0.91 mmol) of benzyl 4-chloro-2-N-phenoxycarbonylanthranilate were treated in the same way as in Preparation Example 17 to obtain 417 mg (yield 74%) of 5-({[(2-benzyloxycarbonyl-5-chloroanilino)carbonyl]amino}sulfonyl)-3-oxo-3,4-dihydro-2H-1,4-benzoxazine-2-carboxylic acid t-butyl ester. Properties: colorless amorphous, PMR (δ ppm, DMSO-$d_6$): 1.29 (9H, s), 5.37 (2H, s), 5.42 (2H, s), 7.19-7.26 (2H, m), 7.37-7.57 (7H, m), 7.97 (1H, d), 8.25 (1H, d), 10.27 (1H, s), 11.25 (1H, s), 12.22 (1H, br).

Then, from 417 mg (0.68 mmol) of the resultant sulfonylurea product, in the same way, 100 mg (yield 32%: 3 steps) of the above-identified compound was obtained. Properties: colorless crystal, Melting point: >200° C. (decomposition), PMR (δ ppm, DMSO-$d_6$): 5.47 (1H, s), 7.11 (1H, s), 7.24 (1H, d), 7.29 (1H, d), 7.76 (1H, s), 7.78 (1H, d), 7.86 (1H, d), 11.25 (1H, S), 11.62 (1H, s).

Preparation Example 30

Synthesis of 4-[(7-hydroxy-2,4 (1H,3H)-quinazolinedion-3-yl)sulfonyl]anthranilic Acid (Compound 30)

620 mg (1.53 mmol) of 3-benzyloxycarbonylamino-4-t-butoxycarbonylbenzenesulfonamide and 550 mg (1.51 mmol) of benzyl 4-hydroxy-2-N-phenoxycarbonylanthranilate were treated in the same way as in Preparation Example 17 to obtain 25 mg (yield 4%: 4 steps) of the above-identified compound. Properties: colorless crystal, Melting point: >200° C. (decomposition), PMR (δ ppm, DMSO-$d_6$): 6.48 (1H, s), 6.61 (1H, d), 7.14 (1H, d), 7.51 (1H, s), 7.70 (1H, d), 7.90 (1H, d), 10.80 (1H, s), 11.39 (1H, s).

Preparation Example 31

Synthesis of 4-[(7-chloro-2,4 (1H,3H)-quinazolinedion-3-yl)sulfonyl]-2-N-propionylanthranilic Acid (Compound 31)

840 mg (1.86 mmol) of Compound 17 was dissolved in 8 ml of 1,4-dioxane, 240 l (2.79 mmol) of propionyl chloride was added dropwise, then the resultant mixture was stirred overnight at 60° C. An excess of water was added to the reaction solution and the mixture was extracted with ethyl acetate. The organic layer thus obtained was washed, dried, and concentrated to obtain a crude product of t-butyl 4-[(7-chloro-2,4 (1H,3H)-quinazolinedion-3-yl)sulfonyl]-2-N-propionylanthranilate. The obtained crude product was stirred at room temperature in 3 ml of trifluoroacetic acid for 1 hour, then the reaction solution was concentrated in vacuo to obtain a crude product. This was washed by diethyl ether to obtain 400 mg (yield 48%: 2 steps) of the above-identified compound. Properties: colorless crystal, Melting point: >200° C. (decomposition), PMR (δ ppm, DMSO-$d_6$): 1.10 (3H, t), 2.45 (2H, dd), 7.11 (1H, s), 7.24 (1H, d), 7.85 (1H, d), 7.88 (1H, d), 8.17 (1H, d), 9.18 (1H, s), 11.07 (1H, s), 11.63 (1H, s).

Preparation Example 32

Synthesis of 4-[(6-chloro-2,4 (1H,3H)-quinazolinedion-3-yl)sulfonyl]anthranilic Acid (Compound 32)

300 mg (0.74 mmol) of 3-benzyloxycarbonylamino-4-t-butoxycarbonylbenzenesulfonamide and 310 mg (0.81 mmol) of benzyl 5-chloro-2-N-phenoxycarbonylanthranilate were treated in the same way as in Preparation Example 17 to obtain 75 mg (yield 26%: 4 steps) of the above-identified compound. Properties: colorless crystal, Melting point: >200° C. (decomposition), PMR (δ ppm, DMSO-$d_6$): 7.13-7.20 (2H, m), 7.56 (1H, s), 7.72 (1H, d), 7.82 (1H, s), 7.90 (1H, d), 11.68 (1H, s).

Preparation Example 33

Synthesis of 4-[(7-chloro-2,4 (1H,3H)-quinazolinedion-3-yl)sulfonyl]-2-N-methanesulfonylanthranilic Acid (Compound 33)

200 mg (0.44 mmol) of Compound 17 was treated in the same way as in Preparation Example 3 to obtain 81 mg of t-butyl 4-[(7-chloro-2,4 (1H,3H)-quinazolinedion-3-yl)sulfonyl]-2-N-methanesulfonylanthranilate. This was used to perform the same debutylation reaction to obtain 53 mg (yield 25%: 2 steps) of the above-identified compound. Properties: colorless crystal, Melting point: >200° C. (decomposition), PMR (δ ppm, DMSO-$d_6$): 3.24 (3H, s), 7.11 (1H, s), 7.25 (1H, d), 7.85-7.91 (2H, m), 8.23 (1H, d), 8.39 (1H, S), 11.05 (1H, br), 11.70 (1H, s).

Preparation Example 34

Synthesis of 3-(3-aminobenzenesulfonyl)-7-chloro-2,4-(1H,3H)quinazolinedion Methanesulfonic Acid Salt (Compound 34)

2.15 g (6.10 mmol) of compound 12 was dissolved in 65 ml of THF and 0.4 ml of methanesulfonic acid was added dropwise. To this solution, 200 ml of ether was added and the resultant precipate was filtered to obtain 2.59 g (yield 95%) of the above-identified compound. Properties: colorless amorphous, PMR (δ ppm, DMSO-$d_6$): 2.35 (3H, s), 6.98 (1H, d), 7.12 (1H, m), 7.25 (1H, m), 7.34 (2H, s), 7.43 (1H, m), 7.86 (1H, s), 11.64 (1H, s).

Preparation Example 35

Synthesis of 7-chloro-3-[4-(pyrazol-3-yl)benzenesulfonyl]-2,4(1H,3H)-quinazolinedione Hydrochloride (Compound 35)

Following the Synthesis Method (B), 5.65 g (25.34 mmol) of 4-(pyrazol-3-yl)beneznesulfonamide was dissolved in 60 ml of THF, then 7.8 ml (52.16 mmol) of DBU was added dropwise. The reaction solution was stirred at room temperature for 10 minutes, then added with 8.5 g (27.86 mmol) of methyl 4-chloro-2-phenoxycarbonyl-aminobenzoate and stirred at room temperature for 3 hours. The reaction solution was further added with 400 mg (0.131 mmol) of methyl 4-chloro-2-phenoxycarbonylaminobenzoate and then stirred at room temperature for 2 hours. An excess of an aqueous solution of citric acid was added to the reaction solution, then extraction was performed using ethyl acetate. The organic layer was washed by water and saturated saline, then dried over anhydrous sodium sulfate and condensed. Methanol was added to the condensed residue, then the mixture was stirred and the resultant crystals were obtained by filtration to obtain 10.49 g of a crude product.

10.49 g of the crude product obtained was suspended in 45 ml of methanol, then 90 ml of a 1N sodium hydroxide aqueous solution was added. The reaction solution was stirred at 60° C. for 40 minutes, then the precipitate was removed by filtration. The filtrate was concentrated in vacuo and the methanol distilled off, then the obtained aqueous mixture was washed by ethyl acetate. The aqueous layer was made acidic by hydrochloric acid to cause the precipitation of crystals. These were then obtained by filtration. The filtrate was extracted by ethyl acetate, the organic layer was washed by saturated saline, and the result was dried and condensed over anhydrous sodium sulfate. The condensed residue and the crystals obtained by filtration above were combined and recrystallized from THF-ethyl acetate-hexane to obtain 7.70 g (yield of 72% in two steps) of N-[4-(pyrazol-3-yl)benzenesulfonyl]-N'-(2-carboxyl-5-chlorophenyl)urea (properties: colorless crystal, melting point: 129 to 132° C., PMR ($\delta$ ppm, DMSO-$d_6$): 6.81 (1H, d), 7.02 (1H, dd), 7.78 (1H, s), 7.89-7.92 (3H, m), 7.96 (2H, d), 8.24 (1H, s), 10.57 (1H, br).

3.0 g (7.14 mmol) of the urea derivative obtained above was dissolved in 60 ml of THF. 1.2 g (7.40 mmol) of CDI was then added under ice cooling and the result stirred for 2 hours. The reaction solution was diluted by ethyl acetate, then successively washed by a citric acid aqueous solution, saturated saline, a 0.5M sodium hydrogencarbonate aqueous solution, and saturated saline. The organic layer was dried over anhydrous sodium sulfate, then condensed to obtain a crude product. The crude product was recrystallized from ethyl acetate to obtain 1.93 g (yield: 67%) of 7-chloro-3-[4-(pyrazol-3-yl)benzenesulfonyl]-2,4 (1H,3H)-quinazolinedione (properties: colorless crystal, melting point: 124 to 126° C. (decomposition), PMR ($\delta$ ppm, $CDCl_3$-$CD_3OD$): 6.73 (1H, s), 7.09 (1H, s), 7.16 (2H, d), 7.48 (1H, s), 7.66 (1H, s), 7.9-8.1 (3H, m), 8.32 (2H, d).

545 mg (1.35 mmol) of the quinazoline derivative obtained above was dissolved in 35 ml of THF, then 0.4 ml of a 1,4-dioxane solution of 4M hydrochloric acid was added dropwise. 20 ml of ether was added to this solution, then the precipitated crystal was obtained by filtration to obtain 572 mg (yield: 96%) of the above-referenced compound. Properties: colorless crystal, melting point: >200° C. (decomposition), PMR ($\delta$ ppm, DMSO-$d_6$): 6.91 (1H, d), 7.15 (1H, d), 7.24 (1H, dd), 7.84 (1H, d), 7.86 (1H, d), 8.01 (2H, d), 8.17 (2H, d), 11.7 (1H, s).

Example 1

Measurement of Chymase Inhibitory Activity

Human heart chymase was purified according to the method of Urata et al. (*J. Biol. Chem.*, 1990, 265, 22348). The inhibitory activity of the quinazoline derivatives of the present invention with respect to chymase was measured in the following manner. That is, the purified enzyme solution was diluted to a suitable concentration with 0.1M tris-hydrochloride buffer (pH=7.5), 1M sodium chloride, and 0.01% TritonX-100 to obtain an enzyme solution. A 10 mM dimethyl sulfoxide (hereinafter referred to as DMSO) solution of Suc-Ala-Ala-Pro-Phe-MCA (Peptide Institute) was diluted 20-fold at the time of use by 0.1M tris-hydrochlorate, 1M sodium chloride, and 0.01% TritonX-100 to obtain the substrate solution.

75 µl of the enzyme solution warmed to 30° C. was mixed with 5 µl of DMSO solution of the test sample. The mixture was preincubated at 30° C. for 10 minutes. Next, 20 µl of a substrate solution warmed to 30° C. was mixed with the test sample-enzyme mixture and incubated at 30° C. After 10 minutes, 50 µl of 30% acetic acid was added to stop the enzymatic reaction. The amount of the AMC produced was quantified using a fluorescent photometer. At the same time, a blind test was carried out by adding, instead of the test sample solution, 5 µl of DMSO and performing the same reaction. The chymase inhibitory activity was expressed by a rate of inhibition, that is, the 50% inhibition concentration ($IC_{50}$), based on the blind test value.

The quinazoline derivatives of the present invention all strongly inhibited human chymase at concentrations of 100 µM. The $IC_{50}$ values for typical compounds are shown in Table I.

TABLE 1

| Example No. | $IC_{50}$ value (µM) |
|---|---|
| 1 | 0.36 |
| 2 | 0.14 |
| 8 | 0.035 |
| 10 | 0.17 |
| 12 | 0.44 |
| 13 | 0.3 |
| 16 | 0.84 |
| 17 | 0.14 |
| 18 | 0.14 |
| 21 | 0.34 |
| 22 | 0.3 |
| 24 | 0.32 |
| 27 | 4.0 |
| 29 | 1.7 |
| 32 | 1.5 |
| 34 | 0.36 |

Example 2

Time-Course of Skin Reaction in Ascaris-Induced Mouse Biphasic Dermatitis Model

Ascaris-induced biphasic dermatitis was induced according to the method described previously (*Folia Pharmacol. Jap.* 112, 221, 1998). That is, 8-week old BALB/c mice (Charles River Japan) were sensitized by intraperitoneal injection of 0.5 ml of a 1:1 mixture of ascaris extract (800 µg/ml, Cosmo Bio Co., Ltd.) and an alum saline suspension (16 mg/ml in saline). Two weeks after the sensitization, 10 µl of ascaris extract (1 mg/ml) was injected intradermally to the right ear of mice. The edema induced at the ear were evaluated immediately before intradermal injection of the ascaris extract (n=3) and 1 hour after (n=4), 2 hours after (n=4), 4 hours after (n=4), 6 hours after (n=4), 16 hours after (n=4), and 24 hours after injection (n=4), by weighing ear biopsy prepared with a punch (a diameter of 6 mm, Fukui Kiko Shokai) and measuring their weights. The edema (mg) was expressed as the difference in the weight of the ear punch biopsy between the right and the left ears of the same mouse.

Biphasic dermatitis was induced by intradermal administration of ascaris extract to the ears of mice sensitized by the same antigen (FIG. 1). The first reaction reached its peak after 1 hour, while the second reaction reached its peak after 16 hours.

Example 3

Effects of Chymase Inhibitor in Ascaris-Induced Mouse Biphasic Dermatitis Model

Dermatitis was induced in accordance with the method described in Example 2 and the ear edema was measured in the same way as in Example 2, 1 hour (n=6) and 16 hours (n=8) after the intradermal administration of ascaris extract to the ears to investigate the effects of the test substance on dermatitis. As the chymase inhibitor, Compound 34 was used. As the control drug, diphenhydrazine (antihistamine, Sigma) and prednisolone (steroid, Nakarai Tesc Co.) were used. Each drug under study was suspended in saline containing 0.5% hydroxypropyl cellulose and administered intraperiotoneally 60 minutes before intradermal administration of ascaris extract. A group of mice sensitized with ascaris extract and challenged by intradermal injection of saline was used as a control (n=3).

Results

As a result of the intraperiotoneal administration of the chymase inhibitor (Compound 34), the reaction after 1 hour (early-phase reaction) and reaction after 16 hours (late-phase reaction) of the biphasic dermatitis induced by ascaris extract were both suppressed in a dose-dependent manner. A statistically significant difference was observed in the dosage of 50 mg/kg (FIG. 2A). The rate of suppression at 50 mg/kg was about 41% for the early-phase reaction and about 45% for the late-phase reaction (both $p<0.01$, Dunnett's test). Prednisolone, which is effective against atopic dermatitis, was substantially ineffective against the early-phase reaction, but strongly inhibited the late-phase reaction in a dosage of 30 mg/kg (rate of suppression: 67%) (FIG. 2B). On the other hand, diphenhydrazine significantly suppressed the early-phase reaction (rate of suppression: 79%), but exhibited almost no effect against the late-phase reaction (FIG. 2C).

The fact that a chymase inhibitor exhibits a suppressive action in an allergic dermatitis model exhibiting biphasic skin reaction shows the involvement of chymase in allergic biphasic dermatitis and usefulness of a chymase inhibitor for such dermatitis. In particular, the finding that a chymase inhibitor, like a steroid, significantly suppresses late-phase reaction, in which antihistamines and anti-allergic agents exhibit little effect, shows the usefulness of a chymase inhibitor in atopic dermatitis. In the following Examples 4 to 6, the skin conditions induced by inoculation of human chymase into the ears of mice were analyzed for the purpose of further confirming the importance of chymase in a biphasic skin reaction.

Example 4

Ability of Single Administration of Human Chymase to Induce Dermatitis

Recombinant human chymase was used in this Example. Recombinant human chymase was obtained by expression and purification in accordance with the already reported method of production of serine protease (*Biochem. Biophys. Acta* 1350, 11, 1997). That is, first, cDNA (79-756) encoding mature human chymase (*J. Biol. Chem.* 266, 17173, 1991) was amplified by the PCR method. The PCR product was cloned to the pDE vector along with the signal sequence of human trypsin II and the region including the cleaved site of enterokinase (23 amino acid). The constructed human chymase expression plasmid was transfected to CHodhfr⁻ cells, and the transfectants were selected by an already reported method (*Arch. Biochem. Biophys.* 307, 133, 1993). The fused protein of the human chymase and trypsin secreted in the culture supernatent of the obtained cells was concentrated using a HiTrap Heparin column (Amersham Pharmacia Biotech), then cleaved with enterokinase (Invitrogen) to produce human mature chymase. The human mature chymase was purified using a heparin 5PW column (Tosoh Corp.) In SDS-polyacrylamide gel electrophoresis analysis, the purified chymase showed a 33-36 kDa broad band. Further, chymase activity was measured in a 0.1M Tris/HCl buffer (pH 8.0) by using 1 mM Suc-Ala-Ala-Pro-Phe-MCA (Peplide Institute) as a substrate and measuring the intensity of fluoresense of the free MCA. As a result, it was confirmed that the purified chymase certainly has the enzymatic activity.

Next, 20 µl of the above recombinant human chymase (hereinafter called human chymase) (0.1 mg/ml) was administered intradermally to an ear of BALB/c mice (Japan Charles River) and the time-course of the edematous reaction of the ears measured by the method described in Example 2 for the purpose of investigating the role of chymase in dermatitis (n=3 to 4). Further, histamine, an inflammation mediator of mast cells, was similarly administered intradermally and the time-couse was compared with the case of administration of human chymase. The histamine (Sigma-Aldrich) was injected by dissolving in saline (0.25 mg/ml).

As shown in FIG. 3A, by administering human chymase (2.0 µg/ear) to the ears of mice, a biphasic edematous reaction resembling the allergic skin reaction shown in the case of Example 2 was induced. That is, the first skin reaction was immediately induced after administration of chymase and reached a peak after 30 minutes to 1 hour. Further, the second skin reaction peaked after 6 hours and continued for at least 24 hours. On the other hand, an immediate edematous reaction was induced even when inoculating histamine, but this skin reaction completely disappeared 20 hours after the inoculation in contrast to the case of inoculation of chymase (FIG. 3B). The analysis of the dose-dependency in the chymase-induced dermatitis revealed that early-phase reaction (after 1 hour) is dose-dependent and that the maximum reaction is observed at 2.0 µg/ear amount the dose used in the experiment (FIG. 4A). On the other hand, in the second (after 16 hours) reaction, while the reactions at 0.5 µg/ear and 1.0 ag/ear were about the same in level, the maximum response was obtained at 2.0 µg/ear in the same way as in the first reaction (FIG. 4B).

As shown above, it was shown that intradermal administration of human chymase in mice induces dermatitis, and that its time-course resembles that of antigen-induced biphasic dermatitis, an acute model of dermatitis, showing the involvement of chymase in biphasic dermatitis.

Example 5

Involvement of Chymase Activity in Dermatitis Induced by Single Administration of Chymase The ability of heat-treated human chymase to induced dermatitis was investigated for the purpose of studying whether the enzymatic activity of chymase is involved in dermatitis induced by human chymase shown. The human chymase was inactivated by incubating a 0.1 mg/ml human chymase solution at 50° C. for 2 hours, then boiling it at 100° C. for 5 minutes. This inactivated human chymase (2.0 µg/ear) was administered to the ears of mice by the method described in Example 4, and the dermatitis was evaluated 1 hour after the administration.

Figure 5:
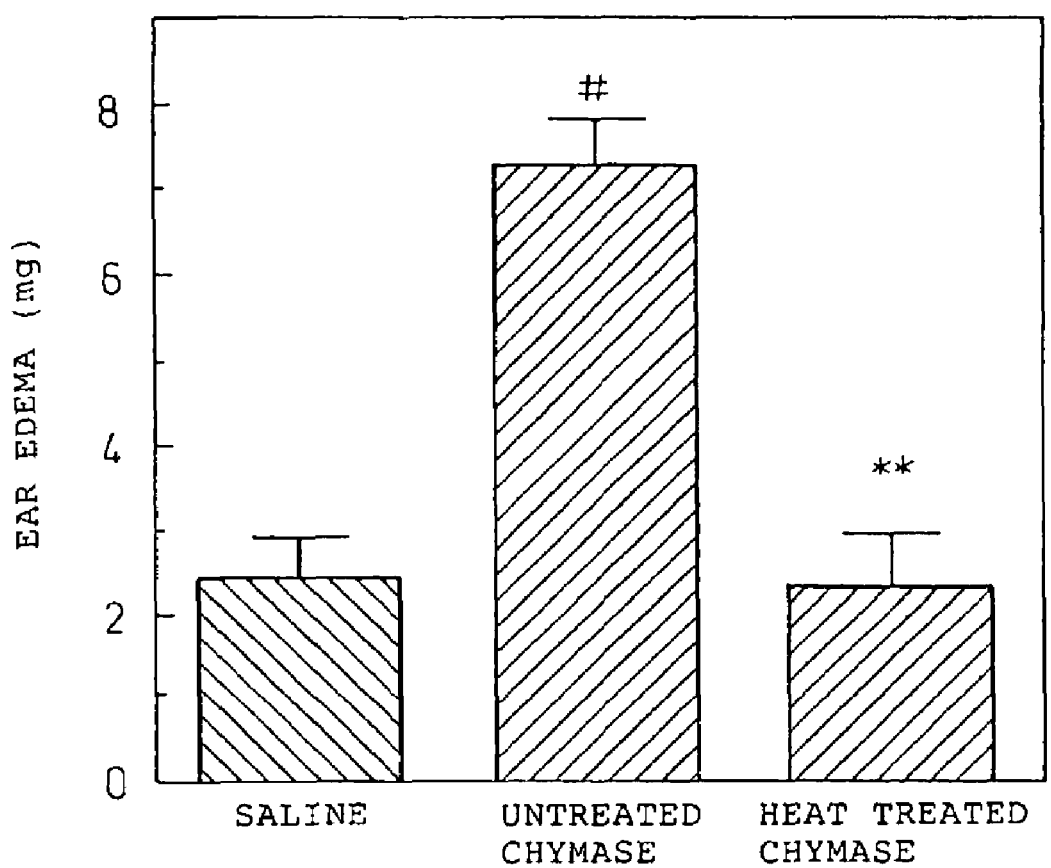
FIG. 5 is a graph showing the effect of heat treatment on the action of human chymase on inducing dermatitis in Example 5.

As a result of the heat treatment of the human chymase, the edema reaction induced by the human chymase completely disappeared (p<0.01 vs. untreated chymase administration group, Student's t-test, N=4) (FIG. 5). This result shows that chymase activity is essential for inducing dermatitis.

Example 6

Histological Analysis of Dermatitis Induced by Single Administration of Chymase

A pathohistological analysis of dermatitis induced by chymase was conducted and a comparison was performed with the biphasic dermatitis shown in Example 2 for the purpose of investigating in further detail the involvement of chymase in biphasic dermatitis. These types of dermatitis were induced in accordance with the methods described in Example 2 and Example 4 (dosage of human chymase was 2.0 µg/ear). The ears were fixed in formalin and paraffin sections were prepared in accordance with an ordinary method 1 hour and 24 hours after administration in both models. The sections were stained with hematoxylin and eosin, then observed under microscope and photographed. Further, sections of ears of normal BALB/c mice were used as negative controls.

Figure 6A:
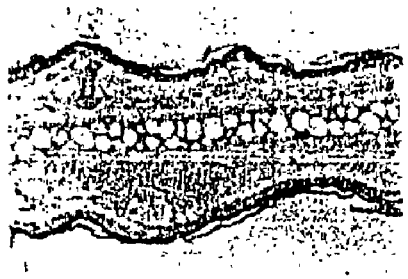
FIGS. 6A to 6E are photos showing the histologically analyzing the dermatitis induced by intradermal injection of human chymase in Example 6, wherein FIG. 6A, normal mice.
Figure 6B:
Figure 6D:
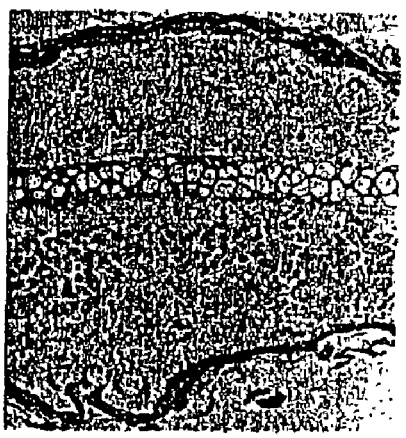
Figure 6C:
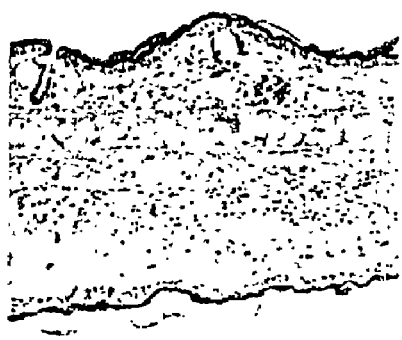
Figure 6E:

In the section 1 hour after elicitation of chymase dermatitis (FIG. 6D), remarkable thickening was observed compared with the sections of ears of normal mice (FIG. 6A), but no difference could be observed between the two in respect to infiltration of leukocytes. As shown in FIG. 6E, however, remarkable cellular infiltration was observed in sections 24 hours after chymase injection. The pattern of the histological change shown by chymase dermatitis resembled that of the ascaris-induced biphasic dermatitis model (FIGS. 6B and 6C). That is, there was remarkable thickening of the tissue at 1 hour, but cellular infiltration was observed only in sections after 24 hours. In summary, it was shown that the dermatitis induced by chymase resembles the biphasic dermatitis induced by an antigen even in a pathohistological analysis.

In the following Example 7 and Example 8, an analysis was conducted on the mechanism of dermatitis induced by chymase to investigate the role of chymase in biphasic dermatitis.

Example 7

Ability of Human Chymase to Induce Dermatitis in Mast Cell-Deficient Mice

Since it has been reported that chymase induces a degranulation in rat peritoneal mast cells (*J. Immunol.* 136, 3812, 1986), it was considered possible that dermatitis induced by chymase is induced through the release of the inflammation mediator from the mast cells. Thus, next the involvement of mast cells in chymase-induced dermatitis was studied using mast-cell deficient mice (*Blood* 52, 447-425, 1978). Mast cell-deficient (WBB6F1-W/W$^v$) mice and their control mice (WBB6F1-+/+) were obtained from SLC Japan. Chymase dermatitis was induced by intradermal administration of human chymase (2.0 µg/ear) and the edema reaction was evaluated after 1 hour and 16 hours using the method described in Example 4.

As shown in FIGS. 7A and 7B, a skin reaction of a similar extent as the control mice (WBB6F1-+/+) was observed even in mast cell deficient (WBB6F1-W/W$^v$) mice after 1 hour (FIG. 7A) and after 16 hours (FIG. 7B). This result indicates that chymase induces a biphasic phase skin reaction regardless of the existence of mast cells.

Example 8

Ability of Human Chymase to Promote Migration of Polymorphonuclear Leukocytes

In Example 6, it was shown that a remarkable infiltration of leukocytes is observed in late-phase reaction of human chymase-induced dermatitis. The effect of human chymase on the migration of polymorphonuclear leukocytes (PMN) in vitro was investigated for the purpose of investigating the mechanism of chymase-induced leukocyte infiltration. PMN was isolated by adding a ⅕th volume of 6% dextran solution to heparinized whole blood from normal healthy subject and allowing it to stand at 37° C. for 1 hour, then layering the supernatent on Ficoll-Paque (Amersham Pharmacia Biotech) and centrifuging it. Further, the migration of PMN was measured by using a 48-well chemotaxis chamber (NeuroProbe Co.) by the textbook method (*Seibutsu Yakkagaku Jikken Koza* (*Biopharmacology Experiment Lectures*) 12, 315, Hirokawa Shoten). That is, a medium containing human chymase (200 to 800 nM) or fMLP (N-formyl-L-methionyl-L-leucyl-L-phenylalanine, Sigma-Aldrich Co.) (10 nM) was placed in the lower well of the chamber. The upper well and the lower well were separated by a polycarbonate filter (pore size 5 µm) (NeuroProbe Co.) PMN ($1 \times 10^6$/ml) was added to the upper well and cultured at 37° C. for 1 hour, then the filter was fixed, stained and the number of cells in the membrane were counted under a microscope (400×) (*Seibutsu Yakkagaku Jikken Koza* (*Biopharmacology Experiment Lectures*) 12, 315). For the cell staining, a hemacolor solution (Merck) was used. In this test, when investigating the effect of the chymase inhibitor, a chymase inhibitor (Compound 18 or Compound 34) was dissolved in dimethyl sulfoxide and added to the lower well of the chamber just before the addition of the human chymase. The concentration of the compound was adjusted so that the final concentration of the dimethyl sulfoxide became 1%.

Figure 8B:
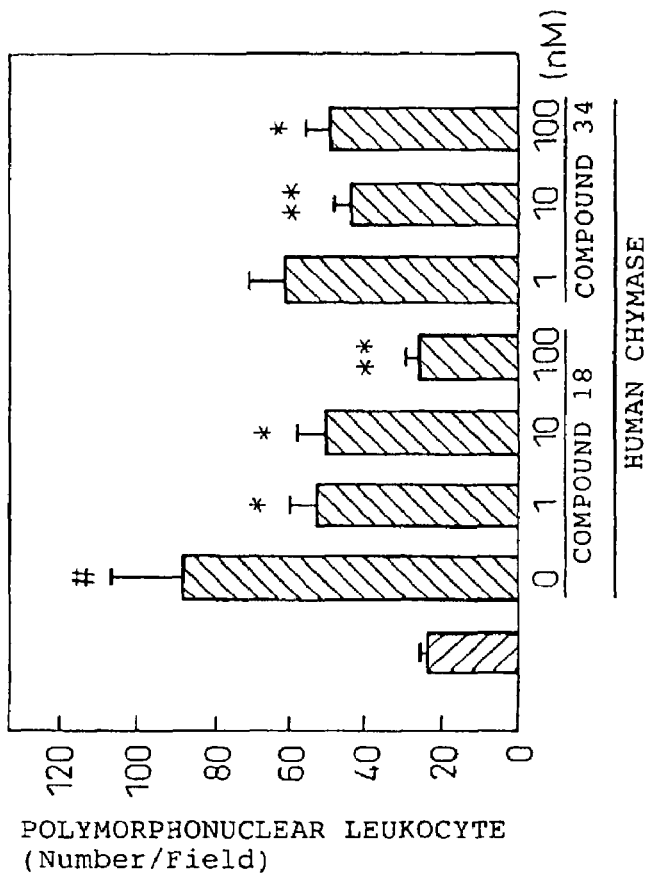
FIG. 8B is a graph showing the effect of a chymase inhibitor on the chymase-induced PMN migration in Example 8.
Figure 8A:
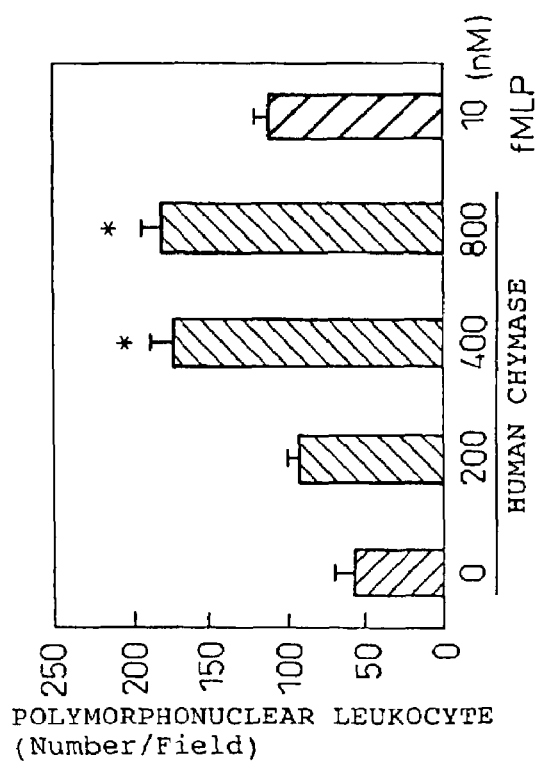
FIG. 8A is a view showing the concentration dependency of the effect of human chymase on migration of human polymorphonuclear leukocytes (PMN) in vitro in Example 8.

As shown in FIG. 8A, human chymase exhibited an activity promoting migration of human PMN in a concentration-dependent manner, with a statistical significance observed at ≧400 nM (p<0.05, Dunnett's test). From the fact that human chymase exhibits activity promoting migration to the same extent as 10 nM fMLP in a concentration of 200 to 400 nM, it is deduced to have an activity of about ⅓₀th that of fMLP. The action of human chymase in promoting the migration of human PMN was significantly suppressed by chymase inhibitors, Compound 18 and Compound 34 (FIG. 8B). These results suggest that chymase acts directly on polymorphonuclear leukocytes to promote their migration, and show the involvement of enzymatic activity of chymase in that action.

Taken together, since chymase released by mast cells upon antigen stimuli induces biphasic skin reaction when injected intradermally to mice ear (Example 4 to 6), it is clear that chymase plays an important role in a skin reaction exhibiting biphasic reaction. The data of Examples 7 and 8 suggest a mechanism of involvement of chymase in biphasic skin reaction. In addition, it was also shown that a chymase inhibitor suppresses ascaris-induced dermatitis, a biphasic skin reaction (Example 2 and Example 3).

Next, a mouse dermatitis model induced by repeated application of hapten was analyzed as a model of dermatitis induced by repeated exposure to an antigen and the effects of a chymase inhibitor in this model is shown.

Example 9

Time-Course of Increase in Ear Thickness in Mouse Dermatitis Model Induced by Repeated Application of Hanten Dermatitis was induced in accordance with an already reported method (*J. Pharmacol. Exp. Ther.* 283, 321, 1997) using dinitrofluorobenzene (DNFB) as hapten. That is, the right ears of eight-week old female C3H/HeN mice (Nippon Clare) (n=7) were painted with 0.15% DNFB (25 µl) dissolved in an acetone/olive oil (3:1) every seven days six times. When applying the hapten each time, the ear thickness was measured by a micrometer (Digimatic Indicator, Mitsutoyo Co.) immediately before the application and 1 hour, 6 hours, 24 hours, and 48 hours after the application so as to find the amount of increase from the ear thickness before the first application of hapten. Further, a group similarly treated with an acetone/olive oil solution (3:1) not containing DNFB was used as a control. Further, in a test separate from the above, the ears were cut off immediately before the third application of hapten, the chymase-like activity of the skin was measured in accordance with an already reported method (n=3), and this was compared with the activity of mice treated with an acetone/olive oil solution (3:1) not containing DNFB (n=2).

Figure 9:
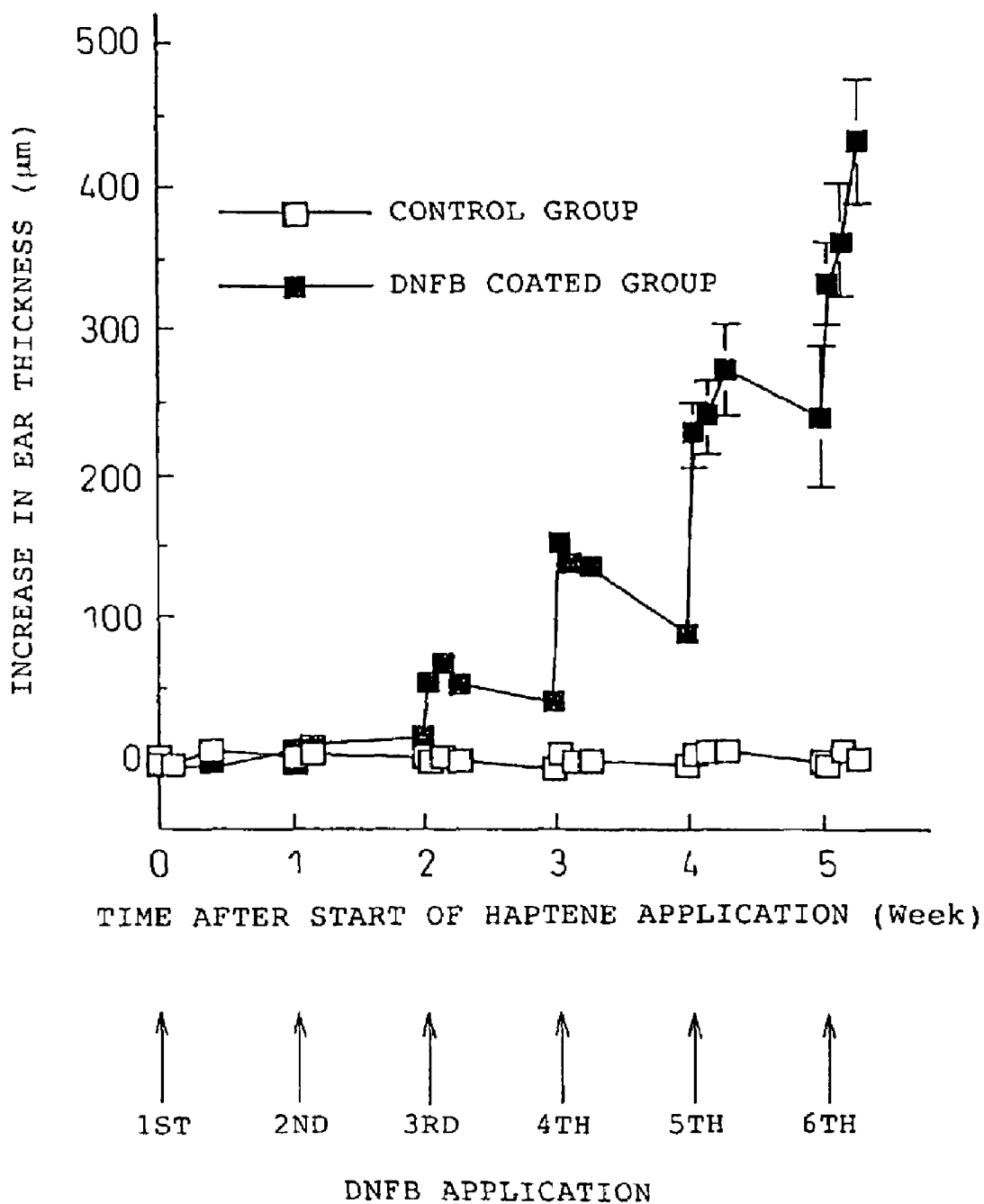
FIG. 9 is a graph showing the time-course of the increase in ear thickness in the dermatitis induced by repeated application of hapten in Example 9.

A transient skin reaction was induced by the application of DNFB. This transient skin reaction gradually became larger with each instance of application (FIG. 9). By the repeated application of DNFB, in addition to an increase in the response to DNFB, the ear thickness before application (baseline value) gradually increased. For example, at the fifth week after the start of application, the thickness of the ear immediately before application increased by about 240 µm compared with the ear before the first application (FIG. 9). In the control group treated with only a solvent not containing DNFB, almost no thickening of the ear was detected at any point of time. The chymase activity of the ear immediately before the third application was significantly higher as compared with the control group treated with only a solvent not containing DNFB (p<0.05, Student's t-test) (FIG. 10). In sammary, it was shown that repeated application of hapten DNFB to the ears of mice induces a sustained ear thickness, in addition to an increase in the chymase activity and a remarkable transient skin reaction.

Example 10

Effect of Chymase Inhibitor in Mouse Dermatitis Model Induced by Repeated Application of Hanten The effect of a test substance on dermatitis was investigated by inducing dermatitis in accordance with the method described in Example 9 (n=7) and measuring the ear thickness in the same way as in Example 9. As the test substance, three chymase inhibitors (Compound 18, Compound 34, and Compound 35) were used, while as the control, the steroid prednisolone (Nakarai Tesc Inc.) was used. Further, the test substance was suspended in saline containing 0.5% hydroxypropyl cellulose in the same way as in Example 3 (HPC/saline) and intraperitoneally administered in dosages of 10 mg/kg or 50 mg/kg once a day for five consecutive days a week until the end of the test; the first administration was performed immediately before the start of the hapten application. Further, a group similarly treated with DNFB and administered HPC/saline instead of the test substance was used as a control group.

Figure 11A:
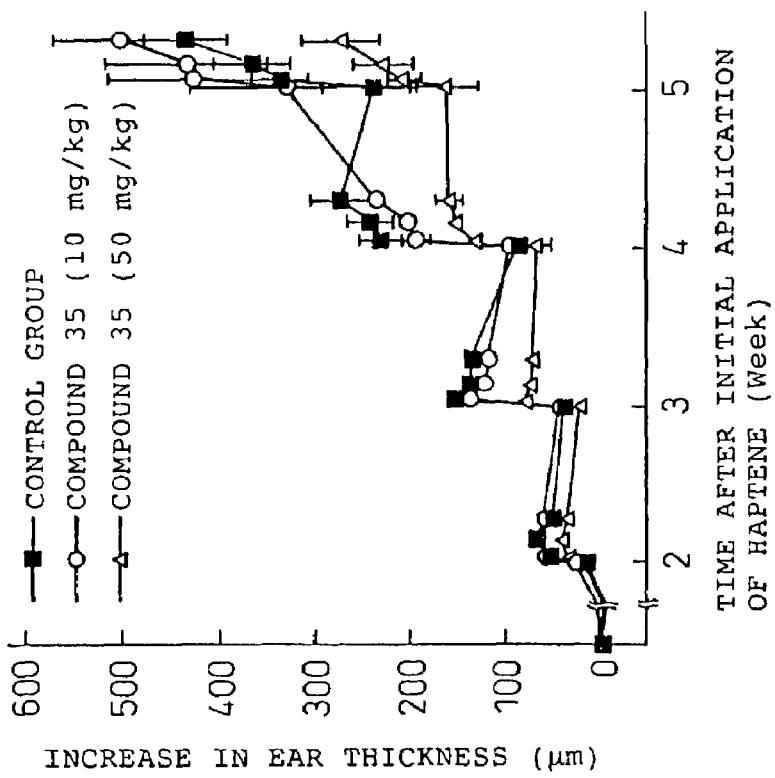
FIGS. 11A to 11D are views showing the effects of chymase inhibitor in the dermatitis induced by repeated application of hapten in Example 10 (FIG. 11A, control drug, prednisolone, FIG. 11B to FIG. 11D, Compound 35, Compound 34, and Compound 18, respectively).
Figure 11B:
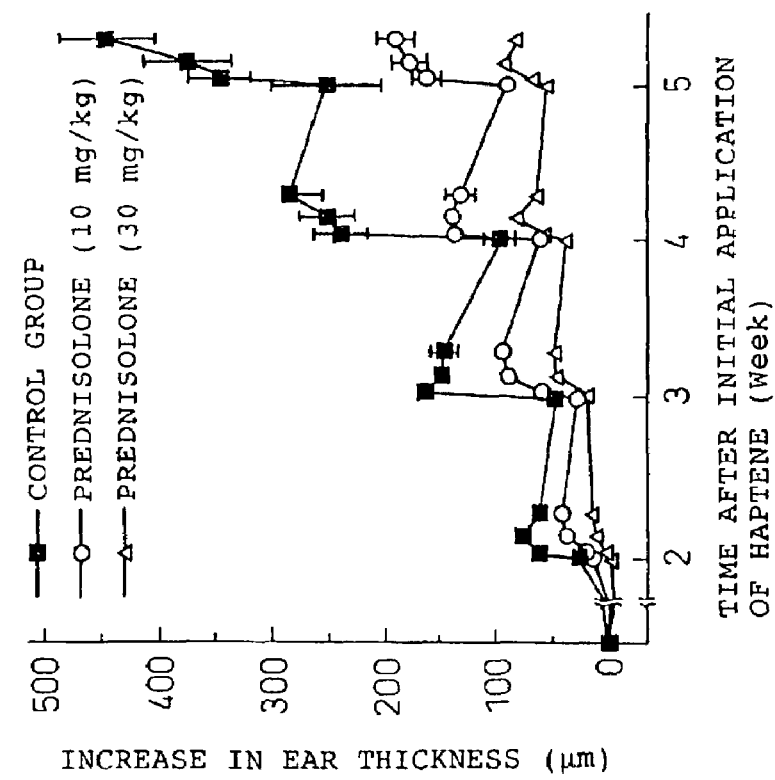
Figure 11D:
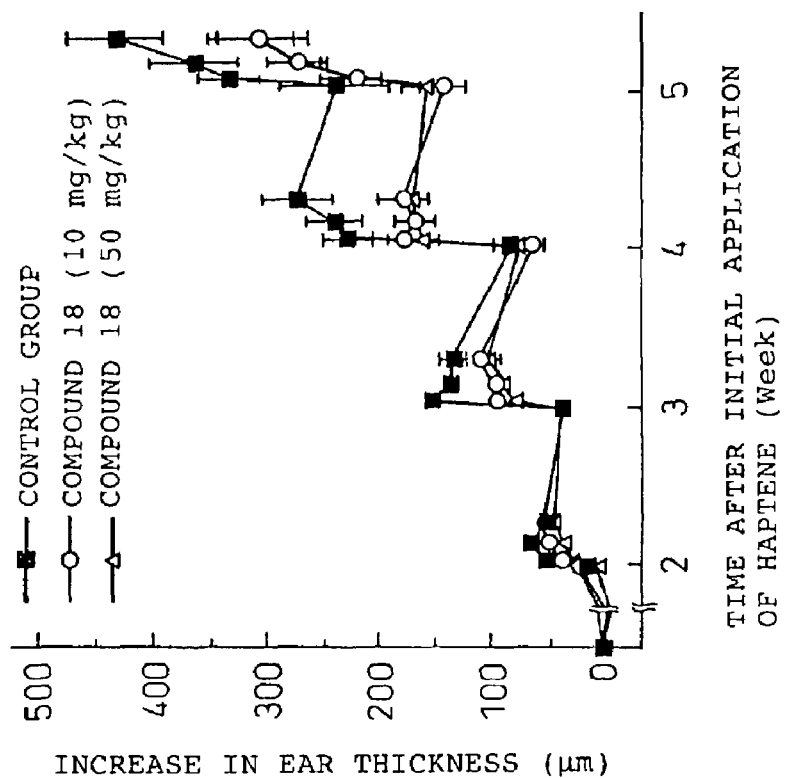
Figure 11C:
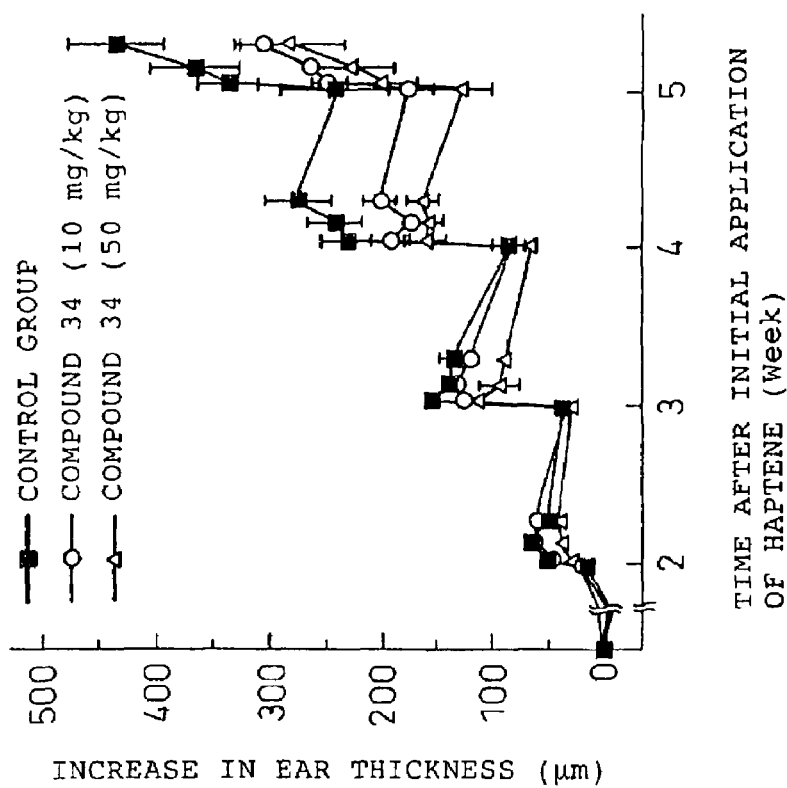

Prednisolone suppressed dermatitis in this model in a dose-dependent manner (FIG. 11A). On the other hand, a chymase inhibitor also remarkably suppressed the transient skin reaction induced by the application of hapten, particularly after the fourth week (3 weeks after initial application of hapten) (FIG. 11B-D). For example, Compound 35 significantly suppressed the increase in ear thickness in the fourth to sixth weeks (3 weeks initial application of hapten, and thereafter) at 50 mg/kg 1 hour, 6 hours, 24 hours, and 48 hours after hapten application (p<0.05, Dunnett's test). Compound 34 also significantly suppressed the skin reaction 1 to 48 hours after the application after the fifth week (4 weeks after initial application of hapten, and threafter) at 50 mg/kg and exhibited a significant suppressive effect 1, 24, and 48 hours after the fifth week (after the fifth application of hapten) and 1 hour after the sixth week (after sixth application of hapten) in an amount of 10 mg/kg. Further, Compound 18 significantly suppressed the reaction 1 to 24 hours after the application in the fourth and fifth weeks (after fourth application and fifth application of hapten) and the reaction 1 to 48 hours in the sixth week (after sixth application of hapten) at 50 mg/kg and exhibited a significant effect 1 to 48 hours after the application in the sixth week (after sixth application of hapten) even at 10 mg/kg.

These results show that chymase inhibitor suppresses edema in mouse dermatitis model induced by repeated application of hapten.

Example 11

Effect of Chymase Inhibitor on Increase in Eosinophils of Skin in Mouse Dermatitis Model Induced by Repeated Application of Hapten The effect of a chymase inhibitor on the infiltration of eosinophils of the skin in the test of Example 10 was studied. That is, 48 hours after the sixth application of hapten, the ears of the mice were fixed with formalin and paraffin sections prepared in accordance with an ordinary method. The sections were stained with Fast Green (Fluka), known to specifically stain eosinophils (*Current Protocol in Immunology*, Wiley Interscience). That is, the deparaffined sections were fixed with 100% methanol for 1 minute, then stained for 30 minutes by 0.2% Fast Green dissolved in 70% ethanol. The eosinophils were measured by randomly selecting 10 fields (×400) under a microscope and counting the number of cells per area using an ocular grid. As the chymase inhibitor, the Compound 18 and Compound 34 were used and =administered by the method described in Example 10. Further, a group treated with an acetone/olive oil solution (3:1) not containing DNFB was used as the non-induced control group, while a group treated with DNFB and administered HPC/saline instead of the test substance was used as the control for the group administered the chymase inhibitor.

Figure 12:
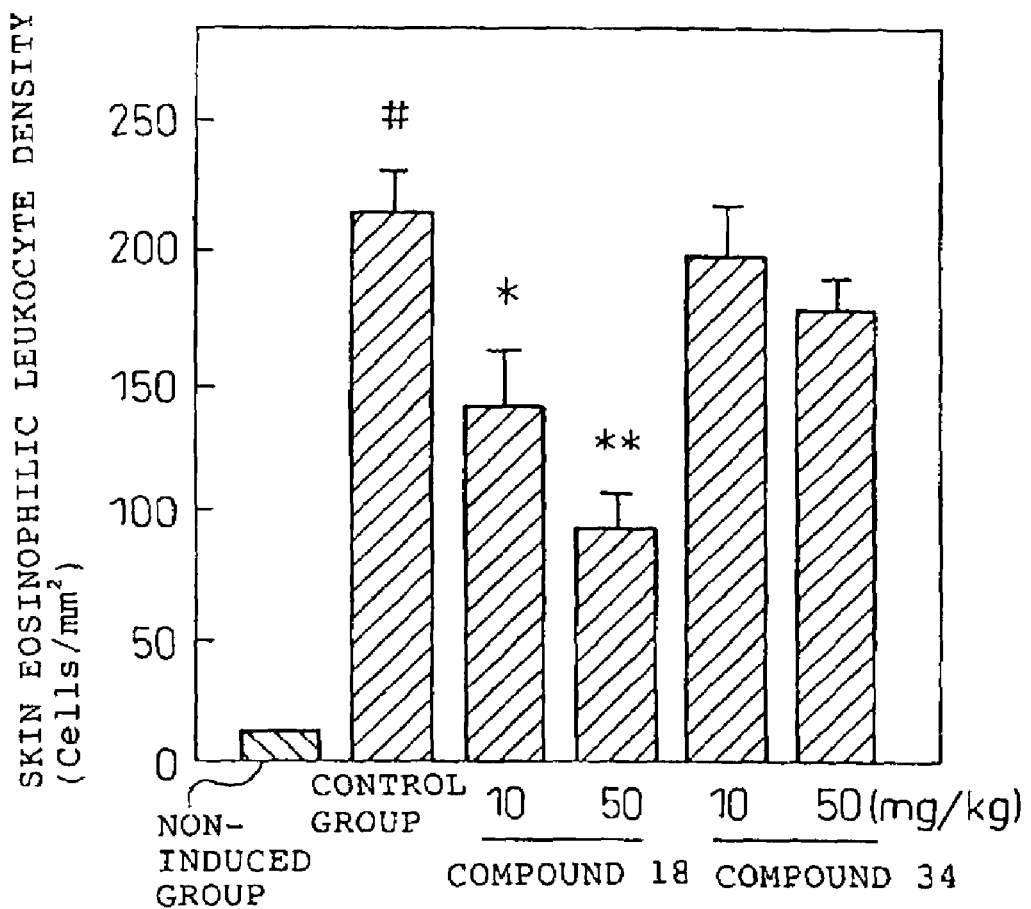
FIG. 12 is a graph showing the effect of a chymase inhibitor on the increase in the number of eosinophils in the dermatitis induced by repeated application of hapten in Example 11.

As shown in FIG. 12, the number of eosinophils remarkably increased by the repeated application of hapten (about 22 times that of the control group, p<0.01, Student's t-test). As a result of administration of a chymase inhibitor (Compound 18), the increase in the eosinophils was significantly suppressed in a dose-dependent manner. That is, the rates of suppression at 10 mg/kg and 50 mg/kg were 37.1% and 60.5%, respectively. For the Compound 34 as well, while no statistically significant difference was recognized, a trend toward suppression dependent on the dosage was shown.

These results suggest that chymase inhibitor suppresses the increase in eosinophils of the skin in mouse dermatitis model induced by repeated application of hapten.

Example 12

Effect of Chymase Inhibitor on Increase in Number of Mast Cells of Skin in Mouse Dermatitis Model Induced by Repeated Application of Hapten The effect of a chymase inhibitor on the increase in mast cells of skin in the test of Example 10 was studied. In the same way as Example 11, the ears of the mice were fixed with formalin and paraffin sections prepared by an ordinary method 48 hours after the sixth application of hapten. The mast cells of the sections were stained by the Toluidine Blue method, then the number of mast cells were counted under a microscope (×400) for 10 fields per section. The density of mast cells of the skin was measured in accordance with the method of Kitagaki et al. (*J. Invest. Dermatol.* 105, 749, 1995). As the chymase inhibitor, use was made of Compound 18 and Compound 34. These were administered by the method described in Example 10. Further, a group treated with an acetone/olive oil solution (3:1) not containing DNFB was used as the non-induced control group, while a group treated with DNFB and administered HPC/saline instead of the test substance was used as the control for the group administered the chymase inhibitor.

Figure 13:
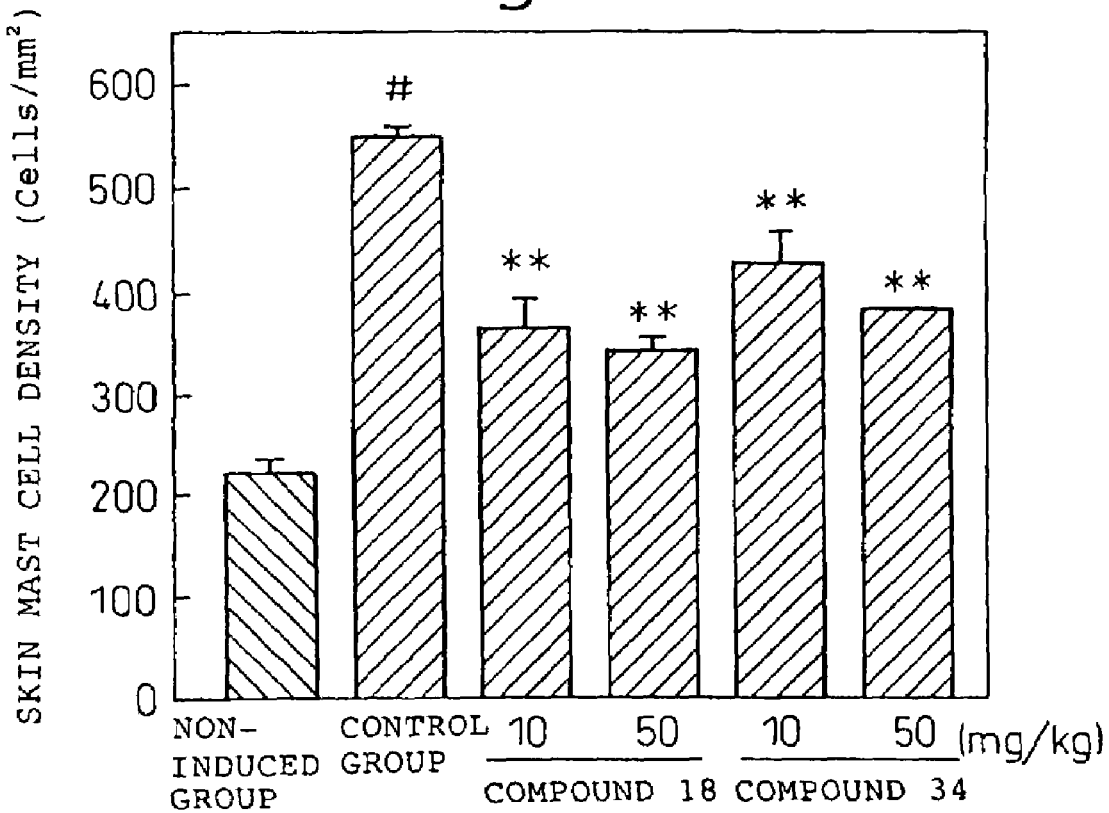
FIG. 13 is a graph showing the effect of a chymase inhibitor on the increase in the number of mast cells in the dermatitis induced by repeated application of hapten in Example 12.
Figure 14:
FIGS. 14A, 14B, and 14C are representative photos showing the effect of a chymase inhibitor on the increase in the number of eosinophils in the dermatitis induced by repeated application of hapten in Example 12.

As shown in FIG. 13, the density of mast cells of the skin significantly increased by the application of hapten (about 2.5 times that of the non-induced group), but as a result of administration of a chymase inhibitor (Compound 18 and Compound 34), the increase in the density of mast cells was significantly suppressed by both the compounds in all dosages. The rate of suppression by Compound 18 was about 57% at 10 mg/kg and about 64% at 50 mg/kg, while the rate of suppression by Compound 34 was about 37% at 10 mg/kg and about 51% at 50 mg/kg. FIG. 14 shows representative micrographs. FIG. 14A shows the ear of a non-induced mouse, FIG. 14B shows the ear of a mouse treated with DNFB and administered HPC/saline (48 hours after the sixth application of DNFB), and FIG. 14C shows the ear a mouse treated with DNFB and administered Compound 34 (48 hours after the sixth application of DNFB). These results suggest that chymase inhibitor suppresses the increase in the number of mast cells of the skin in mouse dermatitis model induced by repeated application of hapten.

Example 13

Ability of Repeated Administration of Human Chymase to Induce Dermatitis

The role of chymase in dermatitis induced by repeated exposure to an allergen was investigated by repeatedly administering intradermally human chymase to the ear of mice. The human chymase was administered once a week (2.0 μg/ear/shot) in accordance with the method described in Example 4. The thickness of the ear was measured by a micrometer (Digimatic Indicator, Mitsutoyo Co.) immediately before each administration of chymase and 1 hour, 6 hours, 24 hours, and 48 hours after the administration to find the increase from the ear thickness before the first administration of chymase. Further, heat-treated chymase was prepared by the method described in Example 5, and its effect was also studied at the same time.

Figure 15:
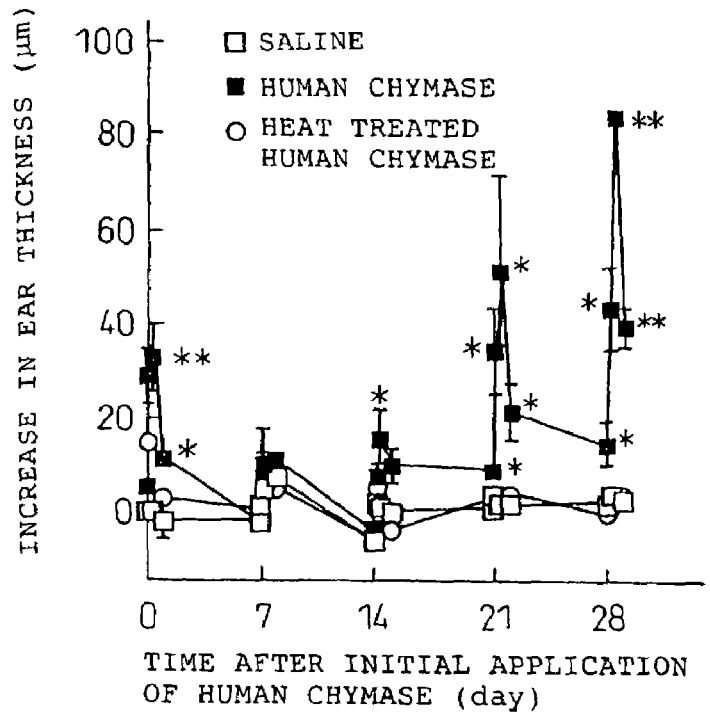
FIG. 15 is a graph showing the time-course of skin thickness when human chymase was repeatedly injected intradermally to mice in Example 13.

A transient skin reaction was induced by intradermal administration of human chymase to the ears of the mice. The reactivity with respect to chymase was about the same among the first to third administrations of chymase, but was amplified by the fourth to fifth administrations (FIG. 15). No transient reaction was observed when the inactivated chymase was administered repeatedly. Further, no skin reaction at all was observed when repeatedly administering this inactivated chymase (FIG. 15). This shows that the skin reaction observed was due to the enzymatic activity of chymase and that the amplification of the skin reaction seen when administering chymase four to five times is not due to the administration of foreign protein to the mice.

Example 14

Effect of Repeated Administration of Human Chymase on Number of Eosinophils of Skin Human chymase was repeatedly administered to the ears of mice to investigate the change in the number of eosinophils of the skin. Human chymase was repeatedly administered to the ears of mice in accordance with the method described in Example 13. The number of eosinophils of the skin was measured by the method described in Example 11. Further, as a control, ear tissue repeatedly administered saline was used.

Figure 16:
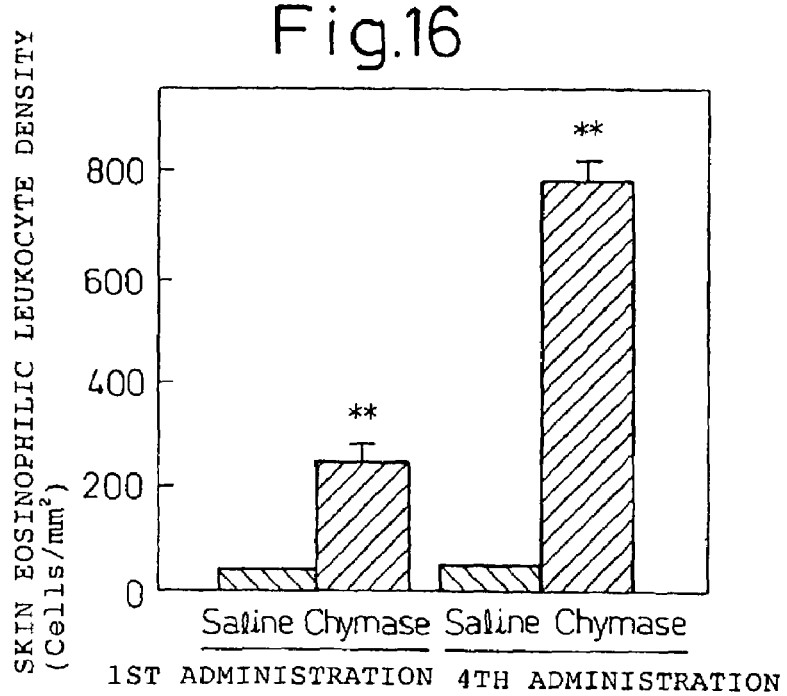
FIG. 16 is a graph showing the time-course of the number of eosinophils in the skin when human chymase was repeatedly injected intradermally to mice in Example 4.

As shown in FIG. 16, in an ear 24 hours after single administration of 2.0 μg of human chymase, there was an approximately 7.6 fold increase in the number of eosinophils compared with an ear administered saline ($p<0.01$, Student's t-test). When human chymase was administered further at 1 week intervals four times in total and the number of eosinophils was measured 1 week after each administration, the number of eosinophils further increased to about 21-fold the group administered saline ($p<0.01$, Student's t-test). These results indicate the possibility that chymase increases the number of eosinophils and that the rate of the increase is dependent on the frequency of the exposure to chymase.

Example 15

Effect of Repeated Administration of Human Chymase on Number of Mast Cells of Skin Human chymase was repeatedly administered intradermally to the ears of mice to investigate the change in the number of mast cells of the skin. Human chymase was administered repeatedly in accordance with the method described in Example 13 and the change in the mast cells of the skin was studied 1 week after administration of the chymase by the method described in Example 12 or the method of measuring the histamine content of the skin. The skin histamine content was measured by cutting off the ear, then homogenizing it in a 20 mM Tris-HCl buffer (pH 7.5), centrifuging the extract (10,000 rpm, 10 minutes), then assaying the amount of histamine in the supernatent using an ELISA kit (Medical Biological Laboratories). Further, as the control, use was made of ear tissue repeatedly administered saline.

Figure 17:
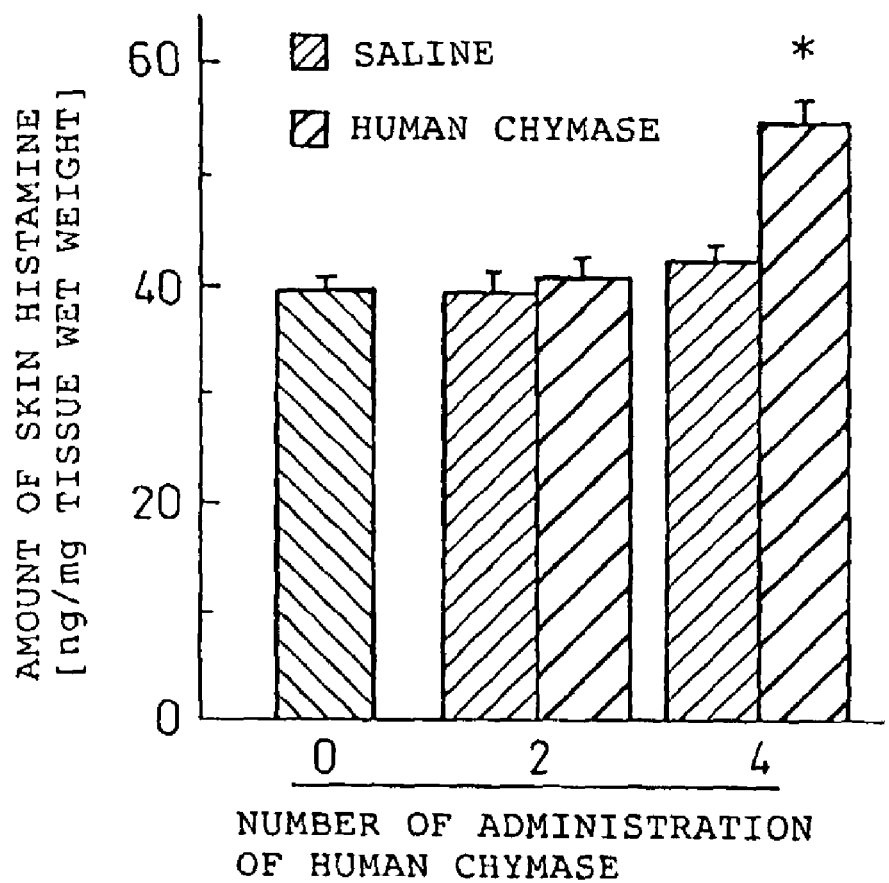
FIG. 17 is a graph showing the time-course of histamine content in the skin when human chymase was repeatedly injected intradermally to mice in Example 15.

The change in the number of mast cells of the skin was observed in accordance with the method described in Example 12, whereupon a tendency for an increase in the number of mast cells by the administration of human chymase was seen. The increase in the number of cells however was not remarkable. Thus, the histamine content of the skin, an indicator of the number of mast cells of tissue, was measured for the purpose of more objectively or quantitatively evaluating the increase in the number of mast cells of the skin. As a result, as shown in FIG. 17, the histamine content of the skin was a significantly higher than the group administered saline a week after the fourth administration of human chymase. From these results, the existence of a mechanism where the chymase derived from mast cells acts on the mast cells in a positive feedback manner is suggested.

Example 16

Effect of Administration of Human Chymase on Stem Cell Factors (SCF)

The expression of stem cell factors (SCF), known as a factor for differentiation and proliferation of mast cells (*Blood* 90, 1345, 1997), was analyzed by the immunohistochemical method for the purpose of clarifying the mechanism of action of the increase in the number of mast cells of the skin when administering human chymase. Human chymase (2.0 ag/ear) was administered to mouse ears by the method described in Example 4. The ears were harvested after 1 hour, after 6 hours, and after 24 hours and frozen tissue sections of 5 μm were prepared by an ordinary method. As a control, sections of ears of normal mice were used. In the immunohistochemical studies, anti-mouse SCF goat IgG (made by R&D Systems) was used as the primary antibody for detection by a PAP kit (DAKO Co.) Note that as a negative control, normal goat IgG (Vector Laboratories Co.) was used instead of an SCF antibody. Further, after immunostaining, nucleus was stained using Methyl Green (Wako Pure Chemicals) in accordance with an ordinary method (*Sensyokuho no Subete* (*Everything About Dyeing*), Ishiyaku Shuppan).

Figure 18A:
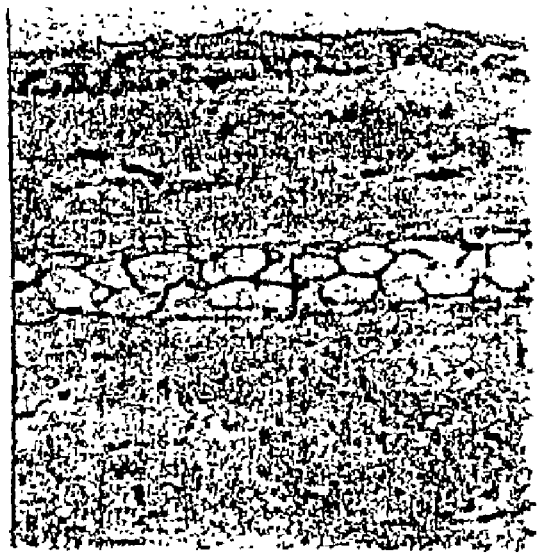
FIGS. 18A and 18B are photos showing representative photos of immunohistological analysis for SCF expression when human chymase was repeatedly injected intradermally to mice in Example 16 (FIG. 18A, normal skin.
Figure 18B:
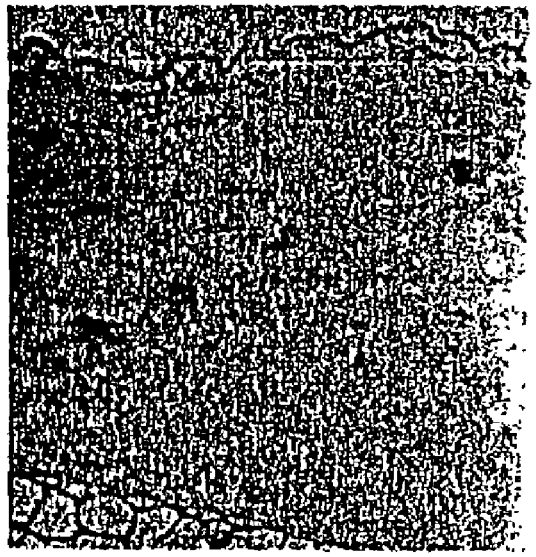

In normal mouse ears, a strong immunostaining was observed around the corneal layer of the epidermis (FIG. 18A). On the other hand, no immunostaining at all was seen when using normal goat IgG instead of anti-SCF antibody as the primary antibody. This shows that the immunostaining in the corneal layer is specific. On the other hand, in the ears of mice administered chymase, the staining around the corneal layer becomes weaker in a time-dependent manner. After 24 hours, almost no formation of color is seen in the ears (FIG. 18B).

Example 17

Effect of Human Chymase on Expression of SCF in Human Keratinocytes

The effect of human chymase on the expression of SCF in human normal keratinocytes in vitro was studied. Human normal keratinocytes were obtained from Cell Applications Co. The cultured keratinocytes were harvested by an enzyme-free cell dissociation buffer (GIBCO BRL Co.), washed three times by PBS, then adjusted to a cell concentration of $10^6/50$ μl, added with human chymase, and allowed to react at 37° C. for 10 minutes. The chymase reaction was stopped by the addition of fetal calf serum (FCS) to give a final concentration of 10%, then the cells were removed by centrifugation. The SCF in the supernatant was assayed by an ELISA kit (PeproTech Co.) The cytotoxicity of chymase to the keratinocytes was investigated using as an indicator the release of lactate dehydrogenase (LDH) using a cytotoxicity detection kit (made by Roche Molecular Biochemicals Co.)

As shown in FIG. 19, the release of SCF was promoted in a concentration-dependent manner by incubating human keratinocytes in the presence of human chymase for 10 minutes. The amount of release of SCF when incubating it in the absence of human chymase for 10 minutes was about the same as when not incubating it. On the other hand, the release of LDH in the supernatent did not change all under these conditions. It was confirmed that the release of SCF due to human chymase was not by cell damage. Above, it was shown in vitro that human chymase acts on membrane-bound SCF of human keratinocytes and causes the release of free SCF.

SCF in composed of two types of molecules of $SCF^{248}$, and $SCF^{220}$ that are generated by the differences in splicing (*Blood* 90, 1345, 1997). $SCF^{248}$ is first synthesized as a cell membrane protein, then processed by some sort of protease to become free SCF which then is released from the cells. On the other hand, $SCF^{220}$ does not have any site digested by an enzyme, so functions only as a membrane protein (*Blood* 90, 1345, 1997). Longley et al. have provided data that the SCF of the skin of healthy subjects is expressed mainly on the cell membranes of keratinocytes of the epidermis, but that in dermatitis accompanied with an increase in skin mast cells, the expression of SCF on the cells is no longer observed and that SCF is detected in the dermis and the intercellular spaces of the keratinocytes (*N. Engl. J. Med.* 328, 1302, 1993). Further, in transgenic mice made to excessively express both of $SCF^{220}$ and $SCF^{248}$, an increase in the number of skin mast cells is observed, but this phenomenon is not seen in transgenic mice made to excessively express only $SCF^{220}$ (*J. Exp. Med.* 187, 1565, 1998). These findings suggest that the patho physiological roles differ between membrane-bound type and free SCF and in particular that free SCF is closely related to the increase in number of mast cells of the skin. In fact, it is known that administration of free SCF to the human skin causes an increase in the number of mast cells of the skin (*J. Exp. Med.* 183, 2681, 1996).

Longley et al. further report that human chymase cleaves membrane binding SCF and converts it to free SCF (*Proc. Natl. Acad. Sci. USA,* 94, 9017, 1997). The findings obtained from Example 16 are completely novel findings proving the data of Longley et al. in vivo. The findings of Example 17 are initial data shown using human cells. Further, the findings of Examples 16 and 17 can be said to be data explaining the increase in skin mast cells induced by administration of chymase shown in Example 15 and the mechanism of action in suppressing the increase in skin mast cells by a chymase inhibitor shown in Example 12.

From the fact that skin reaction that is induced by administrating artificially from the outside chymase released by mast cells upon antigen stimuli is amplified along with the increase in the number of the repeated administration, (Example 13), it is clear that chymase plays an important role in dermatitis induced by repeated exposure to an antigen. Further, from the fact that a chymase inhibitor suppresses the increase in eosinophills or mast cells in skin in dermatitis induced by repeated application of hapten (Examples 11 and 12) and that the administration of chymase causes an increase in eosinophils or mast cells (Examples 14 to 15), it is clear that chymase controls the number of eosinophils or mast cells playing an important role in allergic reactions. Further, it was shown that a chymase inhibitor improves the condition of dermatitis in the dermatitis model induced by repeated application of hapten, which is a model of dermatitis induced by repeated exposure to an antigen (Examples 9 and 10).

Next, the effect of a chymase inhibitor on natural onset dermatitis (NC/Nga) mice as a second model of dermatitis induced by repeated exposure to an antigen will be shown.

Example 18

Effect of Chymase Inhibitor on Natural Onset Dermatitis NC/Nga) Mice

NC/Nga mice were bred and raised in accordance with the methods described in previous reports (*Progress in Medicine* 19, 1201, 1999). Specifically, 5-week old NC/Nga mice obtained from Charles River Japan and raised under a specific pathogen free (SPF) environment were mixed with NC/Nga mice bred by the Faculty of Applied Biological Science of Hiroshima University starting from 6 weeks of age, kept until 15 weeks of age in a normal non-SPF environment, then used for the tests. The tests were conducted under non-SPF, conventional environment. The test substance (Compound 18) was mixed with the drinking water and administered for 35 consecutive days at 150 mg/kg/day (n=7), then an evaluation was conducted in accordance with the method described in previous reports (*Progress in Medicine* 19, 1201, 1999). That is, first, 35 days after the start of administration, the five items of (1) scratching behavior, (2) edema, (3) erythema and hemorrhaging, (4) depilation and ulceration, and (5) dryness were scored as 0 to 2 and the total found to judge the outer appearance of the skin. Next, the ears and skin of the back were fixed with formalin, embedded in paraffin, and histologically analyzed by staining the ear specimens by the hematoxylin and Eosin method, Toluidine Blue method, or Congo Red method (*Stain Technol.* 56, 323, 1981) and by staining the back skin specimens by the Toluidine Blue method or Congo Red method. Sections of the ear stained with Hematoxylin and Eosin were evaluated by judging the change in tissue in four scales of 0 to 3 for three items of (1) thickness of epidermis, (2) thickness of dermis, and (3) cellular infiltration and expressing as the total score. Further, the specimens stained with Toluidine Blue and stained with Congo Red were used for counting the mast cells and eosinophils. Specifically, the eosinophils of the back skin were counted in a ×400 field of a microscope, while the other cells were counted in a total of five ×200 fields and the totals expressed.

Figure 21:
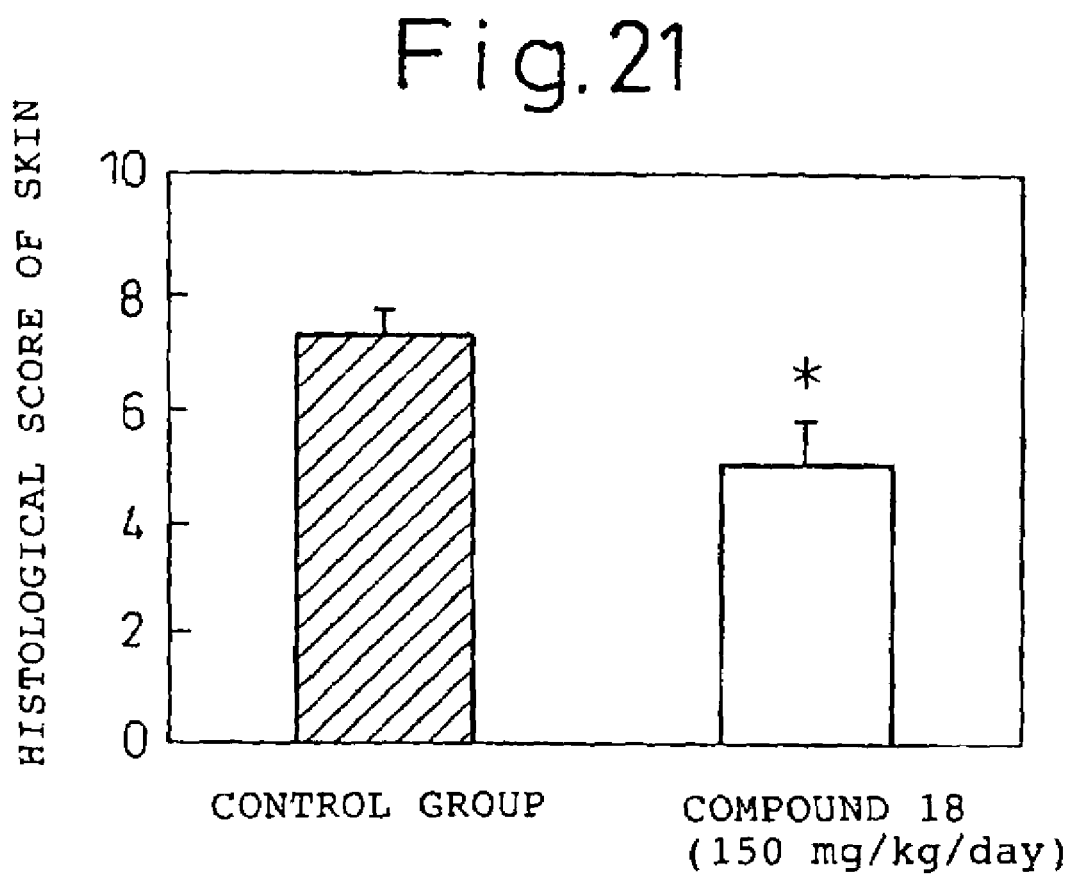
FIG. 21 is a graph showing the effect of a chymase inhibitor on histological scores in NC/Nga mice in Example 18.

As shown in FIGS. 20A and 20B, at the start of the test (15 weeks age), no difference could be seen in the scores of the skin conditions between the control group and the chymase inhibitor (Compound 18) administered group (FIG. 20A), but 35 days after administration of the chymase inhibitor, the dermatitis score decreased significantly compared with the control group (p<0.05, Mann-Whitney test) (FIG. 20B). Similarly, the histological score of the ears also decreased significantly by the administration of a chymase inhibitor (FIG. 21, p<0.05, Mann-Whitney test). On the other hand, the mast cells of the ear skin (FIG. 22A) and back skin (FIG. 22B) were counted. As a result, a significant suppressive effect was recognized by the administration of a chymase inhibitor in both specimens. Further, it was shown that the numbers of eosinophils of the ear skin (FIG. 23A) and back skin (FIG. 23B) were significantly suppressed by a chymase inhibitor.

Above, in a natural onset atopic dermatitis model where onset is considered to occur due to repeated exposure to an antigen in the air under a non-SPF environment, a chymase inhibitor improves the outer appearance of the skin and the histological change of the skin and suppresses the increase in mast cells and infiltration of eosinophils, so the usefulness of a chymase inhibitor against dermatitis induced by repeated exposure to an antigen is demonstrated.

Formulation Example 1

Production of Tablets 100.0 g of Compound 1 was mixed with 22.5 g of microcrystalline cellulose and 2.5 g of magnesium stearate and then tabletized by a single-action type tabletizing machine to produce tablets of a diameter of 9 mm and a weight of 250 mg each containing 200 mg of Compound 1.

Formulation Example 2

Production of Granules 30 g of Compound 1 was mixed well with 265 g of lactose and 5 g of magnesium stearate. The mixture was press molded, then pulverized, granulated, and sieved to obtain excellent 10% granules of 20 to 50 mesh.

Formulation Example 3

Production of Rectal Suppositoru

Vitepsol H-15 (Dynamite Nobel Co.) was warmed to melt. To this was added Compound 1 to a concentration of 12.5 mg/ml. This was homogeneously mixed, then was added in 2 ml amounts to rectal suppository mold and cooled to obtain rectal suppositories each containing 25 mg of Compound 1.

INDUSTRIAL APPLICABILITY

According to the present invention, a chymase inhibitor alleviates a biphasic skin inflammation reaction or its late-phase reaction and is effective against skin thickening of dermatitis induced by repeated application of hapten, one of the animal disease models of atopic dermatitis, and can effectively prevent and/or treat conditions of dermatitis exhibiting a biphasic inflammation reaction or dermatitis induced by repeated exposure to an antigen.

The invention claimed is:

1. A method treatment of dermatitis exhibiting a biphasic skin reaction comprising administering to a patient in need of such treatment a chymase inhibitor in an amount effective for alleviating late-phase reaction, wherein the chymase inhibitor is a quinazolidone derivative having the formula (I) or a pharmaceutically acceptable salt thereof:

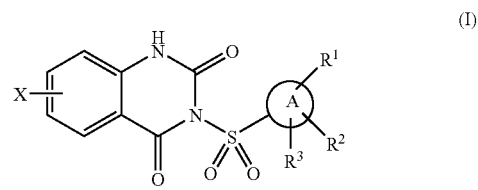

wherein the ring A represents an aryl group,
R$^1$ represents
  a hydroxyl group,
  an amino group,
  a C$_1$ to C$_4$ lower alkylamino group which is optionally substituted with a carboxylic acid group,
  a C$_7$ to C$_{10}$ lower aralkylamino group which is optionally substituted with a carboxylic acid group,
  an amino group acylated with a C$_1$ to C$_4$ lower aliphatic acid which is optionally substituted with a carboxylic acid group, an amino group acylated with an aromatic ring carboxylic acid which is optionally substituted with a carboxylic acid group,
an amino group acrylated with a heteroaromatic ring carboxylic acid which is optionally substituted with a carboxylic acid group,
an amino group sulfonylated with a $C_1$ to $C_4$ lower alkanesulfonic acid which is optionally substituted with a carboxylic acid group,
an amino group sulfonylated with an aromatic ring sulfonic acid which is optionally substituted with a carboxylic acid group,
an amino group sulfonylated with a heteroaromatic ring sulfonic acid which is optionally substituted with a carboxylic acid group,
a $C_1$ to $C_4$ lower alkyl group substituted with a carboxylic acid group, or
a $C_2$ to $C_4$ lower alkylene group which is optionally substituted with a carboxylic acid group;

$R^2$ and $R^3$ may be the same or different, and represent
a hydrogen atom,
an unsubstituted or substituted $C_1$ to $C_4$ lower alkyl group, wherein the substituent group of the $C_1$ to $C_4$ lower alkyl group is a carboxylic acid group, a halogen atom, a $C_1$ to $C_4$ lower alkoxy group, an amino group, a methylamino group, a dimethylamino group, a carboxymethyl amino group or a carboxyethylamino group,
a halogen atom,
a hydroxyl group,
a $C_1$ to $C_4$ lower alkoxyl group,
an amino group,
an unsubstituted or substituted $C_1$ to $C_4$ lower alkylamino group, wherein the substitutent group of the $C_3$ to $C_4$ lower alkylamino group is a carboxylic acid group, a halogen atom or a $C_1$ to $C_4$ lower alkoxyl group,
an unsubstituted or substituted $C_7$ to $C_{10}$ aralkylamino group, wherein the substitutent group of the $C_7$ to $C_{10}$ aralkylamino group is a carboxylic acid group, a halogen atom or a $C_1$ to $C_4$ lower alkoxyl group,
an amino group acylated with a $C_1$ to $C_4$ lower aliphatic acid which is optionally substituted with a carboxylic acid group,
an amino group acylated with an aromatic ring carboxylic acid which is optionally substituted with a carboxylic acid group,
an amino group acylated with a heteroaromatic ring carboxylic acid which is optionally substituted with a carboxylic acid group,
an amino group sulfonylated with a $C_1$ to $C_4$ lower alkanesulfonic acid which is optionally substituted with a carboxylic acid group,
an amino group sulfonylated with an aromatic ring sulfonic acid which is optionally substituted with a carboxylic acid group,
an amino group sulfonylated with a heteroaromatic ring sulfonic acid which is optionally substituted with a carboxylic acid group, or
a carboxylic acid group or
when the ring A is a benzene ring, $R^1$ and $R^2$ may form, together with the substituted benzene ring, a fused heterocyclic ring which is selected from the group consisting of a tetrahydroquinoline, a benzoxazine, a quinoxaline, a benzodioxane, a carboxytetrahydroquinoline, a carboxybenzoxazine, a carboxyquinoxaline and a carboxybenzodioxane, and $R^3$ is the same as defined above; and X represents
a hydrogen atom,
a $C^1$ to $C^4$ lower alkyl group,
a $C^1$ to $C^4$ lower alkoxyl group,
a halogen atom,
a hydroxyl group,
an amino group, or
a nitro group.

2. A method according to claim 1, wherein the dermatitis exhibiting a biphasic skin reaction is atopic dermatitis.

3. A method for alleviation of late-phase reaction of dermatitis exhibiting biphasic skin reaction comprising administering a chymase inhibitor to a patient in need of such treatment in an amount effective for alleviating late-phase reaction of dermatitis exhibiting biphasic skin reaction, wherein the chymase inhibitor is a quinazolidone derivative having the formula (I) or a pharmaceutically acceptable salt thereof:

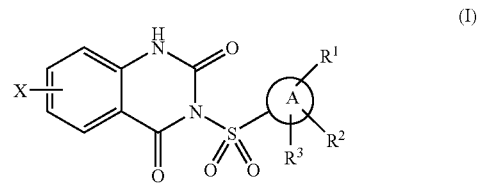

(I)

wherein the ring A represents an aryl group;
$R^1$ represents
a hydroxyl group,
an amino group,
a $C_1$ to $C_4$ lower alkylamino group which is optionally substituted with a carboxylic acid group,
a $C_7$ to $C_{10}$ lower aralkylamino group which is optionally substituted with a carboxylic acid group,
an amino group acylated with a $C_1$ to $C_4$ lower aliphatic acid which is optionally substituted with a carboxylic acid group,
an amino group acylated with an aromatic ring carboxylic acid which is optionally substituted with a carboxylic acid group,
an amino group acrylated with a heteroaromatic ring carboxylic acid which is optionally substituted with a carboxylic acid group,
an amino group sulfonylated with a $C_1$ to $C_4$ lower alkanesulfonic acid which is optionally substituted with a carboxylic acid group,
an amino group sulfonylated with an aromatic ring sulfonic acid which is optionally substituted with a carboxylic acid group,
an amino group sulfonylated with a heteroaromatic ring sulfonic acid which is optionally substituted with a carboxylic acid group,
a $C_1$ to $C_4$ lower alkyl group substituted with a carboxylic acid group, or
a $C_2$ to $C_4$ lower alkylene group which is optionally substituted with a carboxylic acid group;

$R^2$ and $R^3$ may be the same or different, and represent
a hydrogen atom,
an unsubstituted or substituted $C_1$ to $C_4$ lower alkyl group, wherein the substituent group of the $C_1$ to $C_4$ lower alkyl group is a carboxylic acid group, a halogen atom, a $C_1$ to $C_4$ lower alkoxy group, an amino group, a methylamino group, a dimethylamino group, a carboxymethylamino group, or a carboxyethylamino group, a halogen atom, a hydroxyl group, a $C_1$ to $C_4$ lower alkoxyl group, wherein the substituent group of the $C_1$ to $C_4$ lower alkyl group is a carboxylic acid group, a halogen atom, a $C_1$ to $C_4$ lower alkoxy group, an amino group, a methylamino group, a dimethylamino group, a carboxymethyl amino group or a carboxyethylamino group, an amino group, an unsubstituted or substituted $C_1$ to $C_4$ lower alkylamino group, wherein the substitutent group of the $C_1$ to $C_4$ lower alkylamino group is a carboxylic acid group, a halogen atom or a $C_1$ to $C_4$ lower alkoxyl group, an unsubstituted or substituted $C_7$ to $C_{10}$ aralkylamino group, wherein the substitutent group of the $C_7$ to $C$ aralkylamino group is a carboxylic acid group, a halogen atom or a $C_1$ to $C_4$ lower alkoxyl group, an amino group acylated with a $C_1$ to $C_4$ lower aliphatic acid which is optionally substituted with a carboxylic acid group, an amino group acylated with an aromatic ring carboxylic acid which is optionally substituted with a carboxylic acid group, an amino group acylated with a heteroaromatic ring carboxylic acid which is optionally substituted with a carboxylic acid group, an amino group sulfonylated with a $C_1$ to $C_4$ lower alkanesulfonic acid which is optionally substituted with a carboxylic acid group, an amino group sulfonylated with an aromatic ring sulfonic acid which is optionally substituted with a carboxylic acid group, an amino group sulfonylated with a heteroaromatic ring sulfonic acid which is optionally substituted with a carboxylic acid group, or a carboxylic acid group or when the ring A is a benzene ring, $R^1$ and $R^2$ may form, together with the substituted benzene ring, a fused heterocyclic ring which is selected from the group consisting of a tetrahydroquinoline, a benzoxazine, a quinoxaline, a benzodioxane, a carboxytetrahydroquinoline, a carboxybenzoxazine, a carboxyquinoxaline and a carboxybenzodioxane, and $R^3$ is the same as defined above; and X represents a hydrogen atom, a $C_1$ to $C_4$ lower alkyl group, a $C_1$ to $C_4$ lower alkoxyl group, a halogen atom, a hydroxyl group, an amino group, or a nitro group.

4. A method according to claim 3, wherein said dermatitis exhibiting a biphasic skin reaction is atopic dermatitis.

5. A method for treatment of dermatitis induced by repeated exposure to an antigen comprising administering a chymase inhibitor to a patient in need of such treatment in an amount effective for prevention or treatment of said dermatitis, wherein the chymase inhibitor is a quinazolidone derivative having the formula (I) or a pharmaceutically acceptable salt thereof:

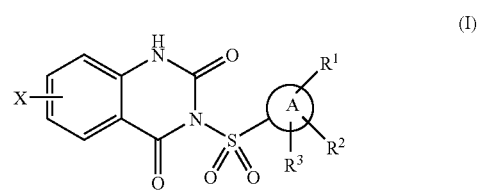

wherein the ring A represents an aryl group;

$R^1$ represents a hydroxyl group, an amino group, a $C_1$ to $C_4$ lower alkylamino group which is optionally substituted with a carboxylic acid group, a $C_7$ to $C_{10}$ lower aralkylamino group which is optionally substituted with a carboxylic acid group, an amino group acylated with a $C_1$ to $C_4$ lower aliphatic acid which is optionally substituted with a carboxylic acid group, an amino group acylated with an aromatic ring carboxylic acid which is optionally substituted with a carboxylic acid group, an amino group acrylated with a heteroaromatic ring carboxylic acid which is optionally substituted with a carboxylic acid group, an amino group sulfonylated with a $C_1$ to $C_4$ lower alkanesulfonic acid which is optionally substituted with a carboxylic acid group, an amino group sulfonylated with an aromatic ring sulfonic acid which is optionally substituted with a carboxylic acid group, an amino group sulfonylated with a heteroaromatic ring sulfonic acid which is optionally substituted with a carboxylic acid group, a $C_1$ to $C_4$ lower alkyl group substituted with a carboxylic acid group, or a $C_2$ to $C_4$ lower alkylene group which is optionally substituted with a carboxylic acid group;

$R^2$ and $R^3$ may be the same or different, and represent a hydrogen atom, an unsubstituted or substituted $C_1$ to $C_4$ lower alkyl group, wherein the substituent group of the $C_1$ and $C_4$ lower alkyl group is a carboxylic acid group, a halogen atom, a $C_1$ and $C_4$ lower alkoxyl group, an amino group, a methylamino group, a dimethylamino group, a carboxymethylamino group or a carboxyethylamino group, a halogen atom, a hydroxyl group, a $C_1$ to $C_4$ lower alkoxyl group, an amino group, an unsubstituted or substituted $C_1$ to $C_4$ lower alkylamino group, wherein the substitutent group of the $C_1$ to $C_4$ lower alkylamino group is a carboxylic acid group, a halogen atom or a $C_1$ to $C_4$ lower alkoxyl group, an unsubstituted or substituted $C_7$ to $C_{10}$ aralkylamino group, wherein the substitutent group of the $C_7$ to $C_{10}$ aralkylamino group is a carboxylic acid group, a halogen atom or a $C_1$ to $C_4$ lower alkoxyl group, an amino group acylated with a $C_1$ to $C_4$ lower aliphatic acid which is optionally substituted with a carboxylic acid group, an amino group acylated with an aromatic ring carboxylic acid which is optionally substituted with a carboxylic acid group, an amino group acylated with a heteroaromatic ring carboxylic acid which is optionally substituted with a carboxylic acid group, an amino group sulfonylated with a $C_1$ to $C_4$ lower alkanesulfonic acid which is optionally substituted with a carboxylic acid group, an amino group sulfonylated with an aromatic ring sulfonic acid which is optionally substituted with a carboxylic acid group, an amino group sulfonylated with a heteroaromatic ring sulfonic acid which is optionally substituted with a carboxylic acid group, or a carboxylic acid group or when the ring A is a benzene ring, $R^1$ and $R^2$ may form, together with the substituted benzene ring, a fused heterocyclic ring which is selected from the group consisting of a tetrahydroquinoline, a benzoxazine, a quinoxaline, a benzodioxane, a carboxytetrahydroquinoline, a carboxybenzoxazine, a carboxyquinoxaline and a carboxybenzodioxane, and $R^3$ is the same as defined above; and X represents a hydrogen atom, a $C_1$ to $C_4$ lower alkyl group, a $C_1$ to $C_4$ lower alkoxyl group, a halogen atom, a hydroxyl group, an amino group, or a nitro group.

* * * * *